(12) United States Patent
Jonai et al.

(10) Patent No.: US 10,226,529 B2
(45) Date of Patent: Mar. 12, 2019

(54) ADJUVANT FOR MUCOSAL VACCINE

(71) Applicant: OSAKA UNIVERSITY, Suita-shi, Osaka (JP)

(72) Inventors: Nao Jonai, Tokyo (JP); Yukako Fujinaga, Osaka (JP); Masahiro Yutani, Osaka (JP); Yo Sugawara, Osaka (JP); Takuhiro Matsumura, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 15/315,015

(22) PCT Filed: Jun. 2, 2015

(86) PCT No.: PCT/JP2015/065831
§ 371 (c)(1),
(2) Date: Nov. 30, 2016

(87) PCT Pub. No.: WO2015/186678
PCT Pub. Date: Dec. 10, 2015

(65) Prior Publication Data
US 2017/0196970 A1  Jul. 13, 2017

(30) Foreign Application Priority Data

Jun. 4, 2014  (JP) ................................ 2014-116241

(51) Int. Cl.

| | | |
|---|---|---|
| *A61K 39/00* | (2006.01) | |
| *A61K 39/02* | (2006.01) | |
| *A61K 39/08* | (2006.01) | |
| *A61K 39/09* | (2006.01) | |
| *A61K 39/04* | (2006.01) | |
| *A61K 39/39* | (2006.01) | |
| *A61K 39/095* | (2006.01) | |
| *A61K 39/102* | (2006.01) | |
| *A61K 39/12* | (2006.01) | |
| *A61K 39/125* | (2006.01) | |
| *A61K 39/13* | (2006.01) | |
| *A61K 39/145* | (2006.01) | |
| *A61K 39/15* | (2006.01) | |
| *A61K 39/155* | (2006.01) | |
| *A61K 39/165* | (2006.01) | |
| *A61K 39/20* | (2006.01) | |
| *A61K 39/21* | (2006.01) | |
| *A61K 39/215* | (2006.01) | |
| *A61K 39/235* | (2006.01) | |
| *A61K 39/245* | (2006.01) | |
| *A61K 39/25* | (2006.01) | |
| *A61K 39/29* | (2006.01) | |

(52) U.S. Cl.
CPC ............. *A61K 39/39* (2013.01); *A61K 39/02* (2013.01); *A61K 39/04* (2013.01); *A61K 39/08* (2013.01); *A61K 39/09* (2013.01); *A61K 39/095* (2013.01); *A61K 39/102* (2013.01); *A61K 39/12* (2013.01); *A61K 39/125* (2013.01); *A61K 39/13* (2013.01); *A61K 39/145* (2013.01); *A61K 39/15* (2013.01); *A61K 39/155* (2013.01); *A61K 39/165* (2013.01); *A61K 39/20* (2013.01); *A61K 39/21* (2013.01); *A61K 39/215* (2013.01); *A61K 39/235* (2013.01); *A61K 39/245* (2013.01); *A61K 39/25* (2013.01); *A61K 39/29* (2013.01); *A61K 2039/541* (2013.01); *A61K 2039/543* (2013.01); *A61K 2039/55516* (2013.01); *Y02A 50/386* (2018.01); *Y02A 50/39* (2018.01); *Y02A 50/466* (2018.01); *Y02A 50/472* (2018.01)

(58) Field of Classification Search
None
See application file for complete search history.

(56) References Cited

U.S. PATENT DOCUMENTS

| | | | | |
|---|---|---|---|---|
| 7,514,088 B2* | 4/2009 | Steward | ............. | A61K 38/4886 424/184.1 |
| 7,811,584 B2* | 10/2010 | Steward | ............. | A61K 38/4886 424/184.1 |
| 8,128,940 B2* | 3/2012 | Steward | ................. | C07K 14/33 424/236.1 |
| 8,273,865 B2* | 9/2012 | Steward | ............. | A61K 38/4886 424/184.1 |
| 8,440,204 B2* | 5/2013 | Johnson | ................. | A61K 39/08 424/185.1 |
| 8,548,417 B2* | 10/2013 | Tucker | .................. | H04M 3/567 455/344 |

(Continued)

FOREIGN PATENT DOCUMENTS

| | | |
|---|---|---|
| EP | 2929893 A1 | 10/2015 |
| JP | 2005-097267 A | 4/2005 |

(Continued)

OTHER PUBLICATIONS

Fujinaga et al, Toxicon 54(2009), 583-586.*

(Continued)

*Primary Examiner* — Nita M. Minnifield
(74) *Attorney, Agent, or Firm* — Foley & Lardner LLP

(57) ABSTRACT

An object of the present invention is to provide an adjuvant for a mucosal vaccine with high safety that induces a sufficient immune response in a mucosal membrane. According to the present invention, an adjuvant for a mucosal vaccine containing a protein complex composed of hemagglutinin (HA) subcomponents HA1 and HA2, and mutant subcomponent HA3 of botulinum toxin is provided.

16 Claims, 18 Drawing Sheets

Specification includes a Sequence Listing.

(56) References Cited

U.S. PATENT DOCUMENTS

| | | | | |
|---|---|---|---|---|
| 8,623,999 | B2* | 1/2014 | Steward | C07K 14/33 435/252.3 |
| 9,662,386 | B2* | 5/2017 | Fujinaga | A61K 39/145 |
| 9,822,344 | B2* | 11/2017 | Kinooka | C12N 5/0696 |
| 2006/0211619 | A1* | 9/2006 | Steward | A61K 38/4886 424/239.1 |
| 2007/0219149 | A1 | 9/2007 | Hasegawa et al. | |
| 2009/0048431 | A1* | 2/2009 | Steward | A61K 38/4886 530/350 |
| 2011/0212157 | A1* | 9/2011 | Edelson | A61K 9/1075 424/443 |
| 2013/0224266 | A1* | 8/2013 | Blais | A61K 39/145 424/400 |
| 2014/0370056 | A1* | 12/2014 | Akiyoshi | A61K 9/06 424/239.1 |
| 2015/0306214 | A1* | 10/2015 | Fujinaga | A61K 39/12 424/197.11 |
| 2016/0324960 | A1* | 11/2016 | Fujinaga | C12N 7/00 |
| 2017/0196970 | A1* | 7/2017 | Jonai | A61K 39/39 |

FOREIGN PATENT DOCUMENTS

| | | | | |
|---|---|---|---|---|
| JP | 2009-081997 A | 4/2009 | | |
| JP | 2009-132686 A | 6/2009 | | |
| JP | WO 2014087849 A1 * | 6/2014 | | A61K 39/02 |
| JP | WO 2015186678 A1 * | 12/2015 | | A61K 39/02 |
| WO | WO 2005/070455 A1 | 8/2005 | | |

OTHER PUBLICATIONS

Sugawara et al, Journal of Cell Biology, 2010, 189/4:691-700; published May 10, 2010.*
Torri et al, Toxicon 77 (2014), 114-120, available online Nov. 20, 2013.*
Fujinaga. Abstracts Toxins 2008/Toxicon 51 (2008) 1-54, abstract only.*
Sugawara et al, Abstracts Toxins 2011/Toxicon 68 (2013) 60-123, abstract only.*
Sugawara et al, Cell Adhesion and Migration 5/1:34-36, Jan./Feb. 2011.*
Lee et al, Microbiology (2005), 151, 3739-3747.*
Amatsu et al., "Crystal Structure of *Clostridium botulinum* Whole Hemagglutinin Reveals a Huge Triskelion-shaped Molecular Complex," The Journal of Biological Chemistry, Dec. 6, 2013, 288(49):35617-65325.

Fujinaga, Yukako, "Elucidation of the mechanism of the botulinum toxin complex for promoting intestinal absorption and development of a novel drug delivery system based on the mechanism," Research Papers of the Suzuken Memorial Foundation, Feb. 2011, 28:298-301, with partial English translation of indicated portions.

Fujinaga, Yukako, Report on Advanced Research Grant Implementation (Funding Program for Next Generation World-Leading Researchers) (Fiscal 2011), Research Project: Elucidation of invasion mechanisms of botulinum toxin complex in body and application of transmucosal vaccine delivery, Japan Society for the Promotion of Science, Nov. 16, 2012, with partial English translation.

Kukreja et al., "Immunological characterization of the subunits of type A botulinum neurotoxin and different components of its associated proteins," Toxicon, May 1, 2009, 53(6):616-624.

Kunisawa et al., "Drug delivery systems for the development of prospective mucosal vaccine," Drug Delivery System, 2008, 23(2):116-122, with English summary on first page reproduced for clarity.

Lee et al., "Production of anti-neurotoxin antibody is enhanced by two subcomponents, HA1 and HA3b, of *Clostridium botulinum* type B 16S toxin-haemagglutinin," Microbiology, 2005, 151:3739-3747.

Matsumura et al., "The botulinum toxin crosses the intestinal epithelial barrier via M cell," Japanese Journal of Bacteriology, 2009, 64(1):79.

Matsumura et al., "Type A HA-positive botulinum toxin complex crosses the intestinal epithelial barrier via M cell," Toxins 2012, Miami Beach, FL, USA, Dec. 5-8, 2012, posters, p. 101.

Nakajima et al., "Molecular Composition of the 16S Toxin Produced by a *Clostridium botulinum* Type D Strain, 1873," Microbiol. Immunol., 1998, 42(9):599-605.

Sato et al., "New trends in vaccine development for the prevention of mucosal infections," Experimental Medicine, Chapter 6: Use of dendritic cells for clinical applications, 2008, 28(20 extra issue):3340-3346, with English abstract.

Sugawara et al., "Botulinum hemagglutinin disrupts the intercellular epithelial barrier by directly binding E-cadherin," J. Cell. Biol., May 10, 2010, 189(4):691-700.

Suzuki et al., "The Development of Mucosal Vaccine Using Bacterial Function for Targeting Mucosal Tissues," Journal of the Pharmaceutical Society of Japan, May 2014, 134(5):629-634, with English summary on first page.

Takahashi et al., "Mechanisms for Mucosal Immunogenicity and Adjuvancy of *Eschericia coli* Labile Enterotoxin," The Journal of Infectious Diseases, 1996, 173:627-635.

Takegahara et al., "Analysis of activity of subunits constituting the botulinum HA complex for destroying the intercellular barrier of intestinal epithelial cells," Japanese Journal of Bacteriology, 2008, 63(1):111, H-8/P111, with English translation.

Xu-Amano et al., "Helper T Cell Subsets for Immunoglobulin A Responses: Oral Immunization with Tetanus Toxoid and Cholera Toxin as Adjuvant Selectively Induces Th2 Cells in Mucosa Associated Tissues," J. Exp. Med., Oct. 1993, 178:1309-1320.

Supplementary European Search Report dated Oct. 26, 2017, in EP 15803250.8.

* cited by examiner

Fig. 1

>FLAG-BHA1
MDYKDDDDKLIQNSLNDKIVTISCKANTDLFFYQVPGNGNVSLFQQTRNYLERWRIIYDSNKAAYKIKSMNIYNTNL
VLTWNAPTHNISAQQDSNADNQYWLLLKDIGNNSFIIASYKNPNLVLYADTVARNLKLSTLNNSSYIKFIIEDYVIS
DFKNFTCRISPILAGGKVVQQVSMTNLAVNLYIWNNDLNQKWTIIYNEEKAAYQFFNKILSNGVLTWIFSDGNTVRV
SSSAQNNDAQYWLINPVSDNYDRYTITNLRDKTKVLDLYGGQTADGTTIQVFNSNGGDNQIWTMSNP

>FLAG-BHA2
MDYKDDDDKLSAERTFLPNGNYNIKSIFSGSLYLSPVSGSLTFSNESSANNQKWNVEYMAENRCFKISNVAEPNKYL
SYDNFGFISLDSLSNRCYWFPIKIAVNTYIMLSLNKVNELDYAWDIYDTNENILSQPLLLLPNFDIYNSNQMFKLEK
I

>Strep-BHA3
MASWSHPQFEKGALEVLFQGPGYQYSDTIDLADGNYVVSRGDGWILSRQNQILGGSVISNGSTGIVGDLRVNDNAIP
YYYPTPSFNEEYIKNNIQTVFANFTEANQIPIGFEFSKTAPSNKNLYMYLQYTYIRYEIIKVLQHEIIERAVLYVPS
LGYVKSIEFNPGEKINKDFYFLTNDKCILNEQFLYKKILETTKNIPTNNIFNSKVSSTQRVLPYSNGLYVINKGDGY
IRTNDKDLIGTLLIEAGSSGSIIQPRLRNTTRPLFTTSNDAKFSQQYTEERLKDAFNVQLFNTSTSLFKFVEEAPSN
KNICIKAYNTYEKYELIDYQNGSIVNKAEYYLPSLGYCEVTNAPSPESEVVKTQVAEDGFIQNGPEEEIVVGVIDPS
ENIQEINTAISDNYTYNIPGIVNNNPFYILFTVNTTGIYKINAQNNLPSLKIYEAIGSGNRNFQSGNLCDDDIKAIN
YITGFDSPNAKSYLVVLLNKDKNYYIRVPQTSSNIENQIKFKREEGDLRNLMNSSVNIIDNLNSTGAHYYTRQSPDV
HDYISYEFTIPGNFNNKDTSNIRLYTSYNQGIGTLFRVTETIDGYNLINIQQNLNLLNSTKSIRLLNGAIYILKVEV
TELNNYNIKLHIDITN

Fig. 2

>AHA1-FLAG
MVIQNSLNDKIVTISCKADTNLFFYQVAGNVSLFQQTRNYLERWRLIYDSNKAAYKIKSMDIHNTNLVLTWNAPTHN
ISTQQDSNADNQYWLLLKDIGNNSFIIASYKNPNLVLYADTVARNLKLSTLNNSNYIKFIIEDYIISDLNNFTCKIS
PILDLNKVVQQVDVTNLNVNLYTWDYGRNQKWTIRYNEEKAAYQFFNTILSNGVLTWIFSNGNTVRVSSSNDQNNDA
QYWLINPVSDTDETYTITNLRDTTKALDLYGGQTANGTAIQVFNYHGDDNQKWNIRNP<u>DYKDDDDK</u>

>FLAG-AHA2
<u>MDYKDDDDKL</u>SVERTFLPNGNYNIKSIFSGSLYLNPVSKSLTFSNESSANNQKWNVEYMAENRCFKISNVAEPNKYL
SYDNFGFISLDSLSNRCYWFPIKIAVNTYIMLSLNKVNELDYAWDIYDTNENILSQPLLLLPNFDIYNSNQMFKLEK
I

>Strep-AHA3
<u>MASWSHPQFEKGALEVLFQGPGY</u>PSDTIDLADGNYVVRRGDGWILSRQNQILGGSVISNGSTGIVGDLRVNDNAIPY
YYPTPSFNEEYIKNNIQTVFTNFTEANQIPIGFEFSKTAPSNKNLYMYLQYTYIRYEIIKVLQHEIIERAVLYVPSL
GYVKSIEFNPGEKINKDFYFLTNDKCILNEQFLYKKILETTKNIPTNNIFNSKVSSTQRVLPYSNGLYVINKGDGYI
RTNDKDLIGTLLIEAGSSGSIIQPRLRNTTRPLFTTSNDTKFSQQYTEERLKDAFNVQLFNTSTSLFKFVEEAPSDK
NICIKAYNTYEKYELIDYQNGSIVNKAEYYLPSLGYCEVTNAPSPESEVVKMQVAEDGFIQNGPEEEIVVGVIDPSE
NIQEINTAISDNYTYNIPGIVNNNPFYILFTVNTTGIYKINAQNNLPSLKIYEAIGSGNRNFQSGNLCDDDIKAINY
ITGFDSFNAKSYLVVLLNKDKNYYIRVPQTSSNIENQIQFKREEGDLRNLMNSSVNIIDNLNSTGAHYYTRQSPDVH
DYISYEFTIPGNFNNKDTSNIRLYTSYNQGIGTLFRVTETIDGYNLINIQQNLHLLNNTNSIRLLNGAIYILKVEVT
ELNNYNIRLHIDITN

Fig. 3

>Strep-BHA3 L473A
MASWSHPQFEKGALEVLFQGPGYQYSDTIDLADGNYVVSRGDGWILSRQNQILGGSVISNGSTGIVGDLRVNDNAIP
YYYPTPSFNEEYIKNNIQTVFANFTEANQIPIGFEFSKTAPSNKNLYMYLQYTYIRYEIIKVLQHEIIERAVLYVPS
LGYVKSIEFNPGEKINKDFYFLTNDKCILNEQFLYKKILETTKNIPTNNIFNSKVSSTQRVLPYSNGLYVINKGDGY
IRTNDKDLIGTLLIEAGSSGSIQPRLRNTTRPLFTTSNDAKFSQQYTEERLKDAFNVQLFNTSTSLFKFVEEAPSN
KNICIKAYNTYEKYELIDYQNGSIVNKAEYYLPSLGYCEVTNAPSPESEVVKTQVAEDGFIQNGPEEEIVVGVIDPS
ENIQEINTAISDNYTYNIPGIVNNNPFYILFTVNTTGIYKINAQNNLPSLKIYEAIGSGNRNFQSGNLCDDDIKAIN
YITGFDSPNAKSYLVV[A]LNKDKNYYIRVPQTSSNIENQIKFKREEGDLRNLMNSSVNIIDNLNSTGAHYYTRQSPDV
HDYISYEFTIPGNFNNKDTSNIRLYTSYNQGIGTLFRVTETIDGYNLINIQQNLNLLNSTKSIRLLNGAIYILKVEV
TELNNYNIKLHIDITN >Strep-BHA3 M508A
MASWSHPQFEKGALEVLFQGPGYQYSDTIDLADGNYVVSRGDGWILSRQNQILGGSVISNGSTGIVGDLRVNDNAIP
YYYPTPSFNEEYIKNNIQTVFANFTEANQIPIGFEFSKTAPSNKNLYMYLQYTYIRYEIIKVLQHEIIERAVLYVPS
LGYVKSIEFNPGEKINKDFYFLTNDKCILNEQFLYKKILETTKNIPTNNIFNSKVSSTQRVLPYSNGLYVINKGDGY
IRTNDKDLIGTLLIEAGSSGSIQPRLRNTTRPLFTTSNDAKFSQQYTEERLKDAFNVQLFNTSTSLFKFVEEAPSN
KNICIKAYNTYEKYELIDYQNGSIVNKAEYYLPSLGYCEVTNAPSPESEVVKTQVAEDGFIQNGPEEEIVVGVIDPS
ENIQEINTAISDNYTYNIPGIVNNNPFYILFTVNTTGIYKINAQNNLPSLKIYEAIGSGNRNFQSGNLCDDDIKAIN
YITGFDSPNAKSYLVVLLNKDKNYYIRVPQTSSNIENQIKFKREEGDLRNL[A]NSSVNIIDNLNSTGAHYYTRQSPDV
HDYISYEFTIPGNFNNKDTSNIRLYTSYNQGIGTLFRVTETIDGYNLINIQQNLNLLNSTKSIRLLNGAIYILKVEV
TELNNYNIKLHIDITN >Strep-BHA3 F569A
MASWSHPQFEKGALEVLFQGPGYQYSDTIDLADGNYVVSRGDGWILSRQNQILGGSVISNGSTGIVGDLRVNDNAIP
YYYPTPSFNEEYIKNNIQTVFANFTEANQIPIGFEFSKTAPSNKNLYMYLQYTYIRYEIIKVLQHEIIERAVLYVPS
LGYVKSIEFNPGEKINKDFYFLTNDKCILNEQFLYKKILETTKNIPTNNIFNSKVSSTQRVLPYSNGLYVINKGDGY
IRTNDKDLIGTLLIEAGSSGSIQPRLRNTTRPLFTTSNDAKFSQQYTEERLKDAFNVQLFNTSTSLFKFVEEAPSN
KNICIKAYNTYEKYELIDYQNGSIVNKAEYYLPSLGYCEVTNAPSPESEVVKTQVAEDGFIQNGPEEEIVVGVIDPS
ENIQEINTAISDNYTYNIPGIVNNNPFYILFTVNTTGIYKINAQNNLPSLKIYEAIGSGNRNFQSGNLCDDDIKAIN
YITGFDSPNAKSYLVVLLNKDKNYYIRVPQTSSNIENQIKFKREEGDLRNLMNSSVNIIDNLNSTGAHYYTRQSPDV
HDYISYEFTIPGNFNNKDTSNIRLYTSYNQGIGTL[A]RVTETIDGYNLINIQQNLNLLNSTKSIRLLNGAIYILKVEV
TELNNYNIKLHIDITN >Strep-BHA3 K607A
MASWSHPQFEKGALEV

Fig. 4

>Strep-AHA3 L473A
MASWSHPQFEKGALEVLFQGPGYPSDTIDLADGNYVVRRGDGWILSRQNQILGGSVISNGSTGIVGDLRVNDNAIPY
YYPTPSFNEEYIKNNIQTVFTNFTEANQIPIGFEFSKTAPSNKNLYMLQYTYIRYEIIKVLQHEIIERAVLYVPSL
GYVKSIEFNPGEKINKDFYFLTNDKCILNEQFLYKKILETTKNIPTNNIFNSKVSSTQRVLPYSNGLYVINKGDGYI
RTNDKDLIGTLLIEAGSSGSIIQPRLRNTTRPLFTTSNDTKFSQQYTEERLKDAFNVQLFNTSTSLFKFVEEAPSDK
NICIKAYNTYEKYELIDYQNGSIVNKAEYYLPSLGYCEVTNAPSPESEVVKMQVAEDGFIQNGPEEEIVVGVIDPSE
NIQEINTAISDNYTYNIPGIVNNNPFYILFTVNTTGIYKINAQNNLPSLKIYEAIGSGNRNFQSGNLCDDDIKAINY
ITGFDSPNAKSYLVV[A]LNKDKNYYIRVPQTSSNIENQIQFKREEGDLRNLMNSSVNIIDNLNSTGAHYYTRQSPDVH
DYISYEFTIPGNFNNKDTSNIRLYTSYNQGIGTLFRVTETIDGYNLINIQQNLHLLNNTNSIRLLNGAIYILKVEVT
ELNNYNIRLHIDITN >Strep-AHA3 M508A
MASWSHPQFEKGALEVLFQGPGYPSDTIDLADGNYVVRRGDGWILSRQNQILGGSVISNGSTGIVGDLRVNDNAIPY
YYPTPSFNEEYIKNNIQTVFTNFTEANQIPIGFEFSKTAPSNKNLYMLQYTYIRYEIIKVLQHEIIERAVLYVPSL
GYVKSIEFNPGEKINKDFYFLTNDKCILNEQFLYKKILETTKNIPTNNIFNSKVSSTQRVLPYSNGLYVINKGDGYI
RTNDKDLIGTLLIEAGSSGSIIQPRLRNTTRPLFTTSNDTKFSQQYTEERLKDAFNVQLFNTSTSLFKFVEEAPSDK
NICIKAYNTYEKYELIDYQNGSIVNKAEYYLPSLGYCEVTNAPSPESEVVKMQVAEDGFIQNGPEEEIVVGVIDPSE
NIQEINTAISDNYTYNIPGIVNNNPFYILFTVNTTGIYKINAQNNLPSLKIYEAIGSGNRNFQSGNLCDDDIKAINY
ITGFDSPNAKSYLVVLLNKDKNYYIRVPQTSSNIENQIQFKREEGDLRNL[A]NSSVNIIDNLNSTGAHYYTRQSPDVH
DYISYEFTIPGNFNNKDTSNIRLYTSYNQGIGTLFRVTETIDGYNLINIQQNLHLLNNTNSIRLLNGAIYILKVEVT
ELNNYNIRLHIDITN >Strep-AHA3 F569A
MASWSHPQFEKGALEVLFQGPGYPSDTIDLADGNYVVRRGDGWILSRQNQILGGSVISNGSTGIVGDLRVNDNAIPY
YYPTPSFNEEYIKNNIQTVFTNFTEANQIPIGFEFSKTAPSNKNLYMLQYTYIRYEIIKVLQHEIIERAVLYVPSL
GYVKSIEFNPGEKINKDFYFLTNDKCILNEQFLYKKILETTKNIPTNNIFNSKVSSTQRVLPYSNGLYVINKGDGYI
RTNDKDLIGTLLIEAGSSGSIIQPRLRNTTRPLFTTSNDTKFSQQYTEERLKDAFNVQLFNTSTSLFKFVEEAPSDK
NICIKAYNTYEKYELIDYQNGSIVNKAEYYLPSLGYCEVTNAPSPESEVVKMQVAEDGFIQNGPEEEIVVGVIDPSE
NIQEINTAISDNYTYNIPGIVNNNPFYILFTVNTTGIYKINAQNNLPSLKIYEAIGSGNRNFQSGNLCDDDIKAINY
ITGFDSPNAKSYLVVLLNKDKNYYIRVPQTSSNIENQIQFKREEGDLRNLMNSSVNIIDNLNSTGAHYYTRQSPDVH
DYISYEFTIPGNFNNKDTSNIRLYTSYNQGIGTL[A]RVTETIDGYNLINIQQNLHLLNNTNSIRLLNGAIYILKVEVT
ELNNYNIRLHIDITN >Strep-AHA3 K607A
MASWSHPQFEKGALEVLFQGPGYPSDTIDLADGNYVVRRGDGWILSRQNQILGGSVISNGSTGIVGDLRVNDNAIPY
YYPTPSFNEEYIKNNIQTVFTNFTEANQIPIGFEFSKTAPSNKNLYMLQYTYIRYEIIKVLQHEIIERAVLYVPSL
GYVKSIEFNPGEKINKDFYFLTNDKCILNEQFLYKKILETTKNIPTNNIFNSKVSSTQRVLPYSNGLYVINKGDGYI
RTNDKDLIGTLLIEAGSSGSIIQPRLRNTTRPLFTTSNDTKFSQQYTEERLKDAFNVQLFNTSTSLFKFVEEAPSDK
NICIKAYNTYEKYELIDYQNGSIVNKAEYYLPSLGYCEVTNAPSPESEVVKMQVAEDGFIQNGPEEEIVVGVIDPSE
NIQEINTAISDNYTYNIPGIVNNNPFYILFTVNTTGIYKINAQNNLPSLKIYEAIGSGNRNFQSGNLCDDDIKAINY
ITGFDSPNAKSYLVVLLNKDKNYYIRVPQTSSNIENQIQFKREEGDLRNLMNSSVNIIDNLNSTGAHYYTRQSPDVH
DYISYEFTIPGNFNNKDTSNIRLYTSYNQGIGTLFRVTETIDGYNLINIQQNLHLLNNTNSIRLLNGAIYIL[A]VEVT
ELNNYNIRLHIDITN

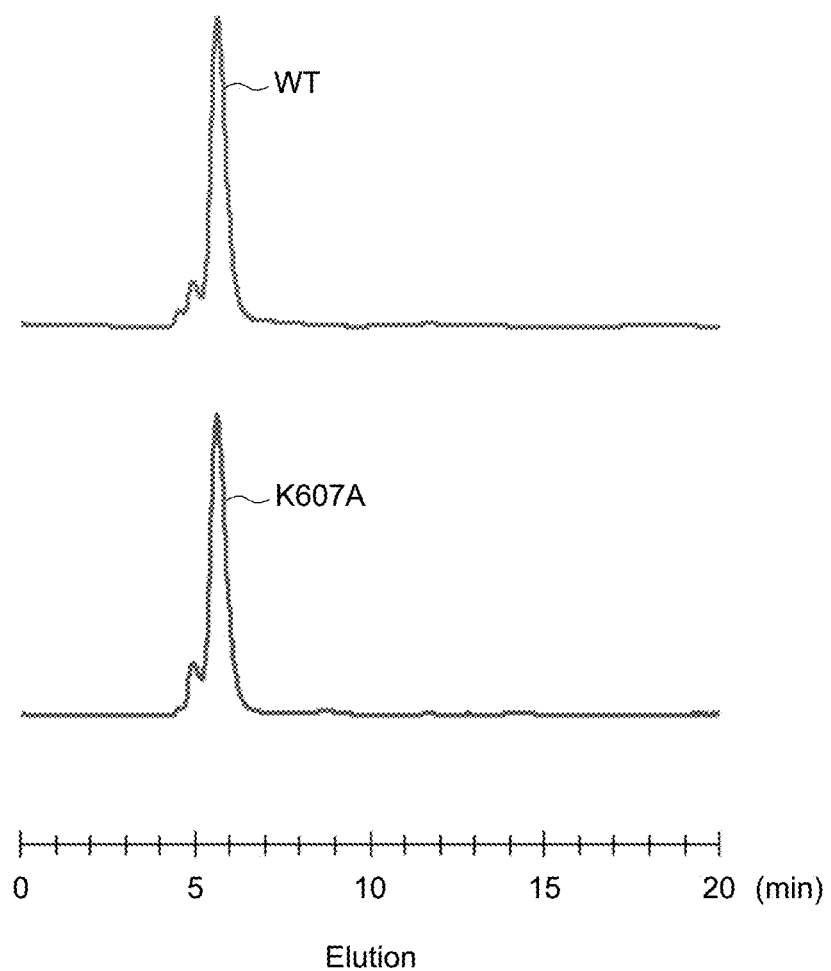

Fig. 15
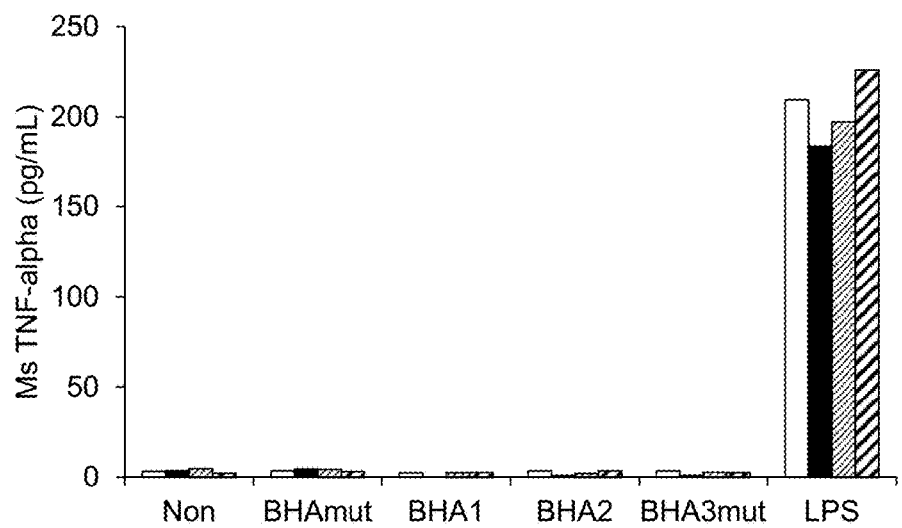
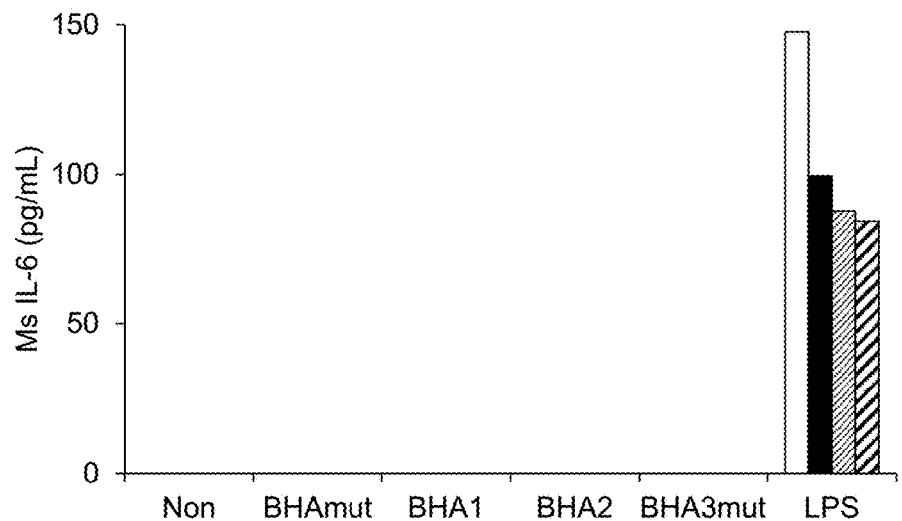

Fig. 18
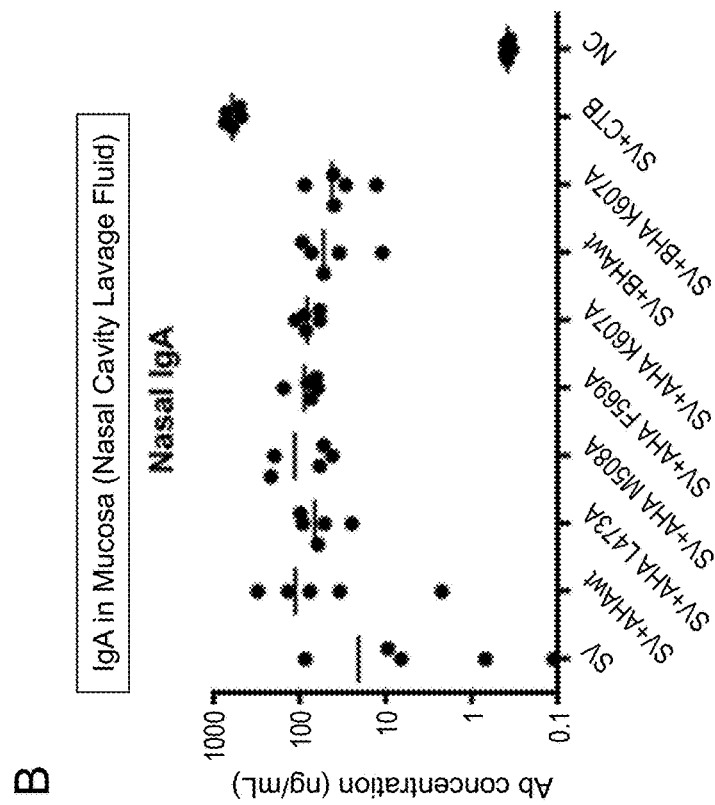
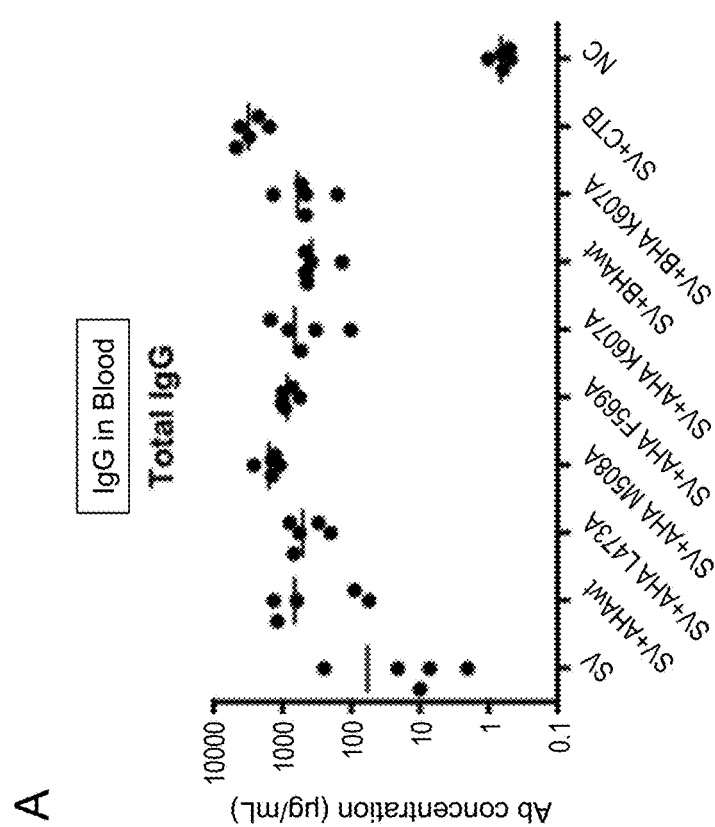

ADJUVANT FOR MUCOSAL VACCINE

CROSS-REFERENCE TO RELATED APPLICATIONS

This application is a National Stage application of PCT/JP2015/065831, filed Jun. 2, 2015, which claims priority from Japanese application JP 2014-116241, filed Jun. 4, 2014.

TECHNICAL FIELD

The present invention relates to an effective and safe adjuvant for a mucosal vaccine and a mucosal vaccine preparation containing the adjuvant and a vaccine antigen.

BACKGROUND ART

In recent years, immune mechanisms on mucosal membranes covering the respiratory apparatus, the digestive apparatus, the reproductive organs, and other organs have been gradually elucidated as the immune mechanism to protect an organism from infectious diseases such as influenza and AIDS. For example, an immune response derived from influenza virus infection is associated with an IgA antibody secreted on a mucosal membrane, an IgG antibody induced in blood to neutralize the virus, and cytotoxic T cells that lyse infected cells to interrupt virus transmission. Such a mucosal immune mechanism is an immune system present at the initial phase of the infection, and plays a key role in biophylaxis at the time of the infection or during the initial phase of the infection. Accordingly, a mucosal vaccine inducing an immune system preventing infection on a mucosal surface, which is the first barrier at portals of entry for a pathogen, is regarded as effective for various mucosal infections.

A mucosal vaccine induces production of a secretory IgA antibody in a mucosal tissue through transmucosal administration such as transnasal administration, and also induces production of an IgG antibody in a serum. Thus, the mucosal vaccine is capable of inducing immune responses in both the mucosal and systemic systems against a pathogen, and in addition, is superior to conventional injection administration in terms of operability, safety, and economic efficiency, and accordingly, is expected for clinical application as a novel vaccine, and has been developed.

On the other hand, since a mucosal vaccine for singly administering an antigen is not capable of inducing a sufficient immune response, it has been revealed that an adjuvant for a mucosal vaccine is indispensably used together in order to induce an effective immune response on the mucosal surface. Up to the present, many adjuvants for mucosal vaccines have been reported, and for example, bacterial endotoxins such as cholera toxin (CT) and heat-labile enterotoxin (LT) of enterotoxigenic E. coli, are known as representative adjuvants for activating mucosal immunity (Non-Patent Documents 1 and 2). However, it has been reported that clinical trials with LT transnasal administration caused facial nerve palsy (Bell's palsy), and hence, it is now regarded that there is a problem of safety in development of nasal adjuvants using toxins themselves such as CT and LT. Besides, MPL resulting from attenuation of the activity of endotoxin LPS, bacterial flagellar protein Flagellin (Patent Document 1), double-stranded RNA (poly(I:C)) (Patent Document 2) and the like, all of which are not toxins, have been studied as adjuvants for mucosal immunity activation, but since those candidates induce excessive inflammatory responses, they are also not satisfactory in terms of safety. In this manner, no effective and safe adjuvant for a mucosal vaccine has been put to practical use at present.

On the other hand, hemagglutinin (HA) and a nontoxic-nonhemagglutinin (NTNH) component bind to botulinum neurotoxin (NTX) produced by botulinum causing food poisoning, so as to form a large neurotoxin complex (progenitor toxin (PTX)) having a molecular weight of 300,000, 500,000, or 900,000. When botulism is caused, botulinum toxin blocks neuron transmission and leads to death, but taking advantage of the activity thereof, it is used as an effective neurotransmission inhibitor for medical purposes. For example, a botulinum toxin type A (BOTOX) complex is known to be used for treatment of blepharospasm, hemi-facial spasm, spasmodic torticollis and heterotropia, and reduction of wrinkles. Among the neurotoxin complexes described above, non-toxic hemagglutinin (HA) is known to have functions of disrupting the barrier function of epithelial cells on the basolateral membrane side and transporting botulinum neurotoxins and macromolecules. When NTX and an albumin antigen are subcutaneously administered to a mouse in combination with HA, antigen-specific production of an antibody in blood is enhanced through IL-6 production (Non-Patent Document 3). While Patent Documents 3 and 4 describe the adjuvant activity of an HA subcomponent (HA1 or HA3) and use of a nucleic acid as a carrier for intracellular introduction, no protein complex composed of HA subcomponents (HA1, HA2 and HA3) is not discussed. The present inventors previously reported that HA acts on M cells in the epithelial cell layer of the Peyer's patch (M cells on the Peyer's patch), and that HA assists migration and entrance of a neurotoxin complex from the M cells to the basolateral side via transcytosis (Non-Patent Document 4). While the function of the neurotoxin complex (the HA to which a toxin component has been bound) to cross the intestinal epithelial barrier was investigated in the study described above, interaction of toxin-free HA with M cells and an adjuvant effect for delivering a vaccine for a mucosal infection have not yet been discussed. Besides, Non-Patent Document 5 describes M cell orientation of an HA complex, and Non-Patent Documents 6 and 7 describe involvement of HA2-HA3 in E-cadherin binding, but the function of the HA complex as a mucosal vaccine adjuvant is not discussed in any of these.

PRIOR ART DOCUMENTS

Patent Documents

Patent Document 1: WO 2005/070455
Patent Document 2: JP Patent Publication (Kokai) No. 2005-97267 A
Patent Document 3: JP Patent Publication (Kokai) No. 2009-132686 A
Patent Document 4: JP Patent Publication (Kohyo) No. 2009-81997 A Non-Patent Documents Non-Patent Document 1: J. Xu-Amano et al., J. Exp. Med., 178, 1309 (1993)
Non-Patent Document 2: I. Takahashi et al., J. Infect. Dis. 173, 627 (1996)
Non-Patent Document 3: J. Lee et al., Microbiology, 151, 3739 (2005)
Non-Patent Document 4: Takuhiro Matsumura et al., Japanese Journal of Bacteriology 64 (1) 79 (2009)

Non-Patent Document 5: Matsumura T, Sugawara Y, Yutani M, Fujinaga Y, Type A HA-positive botulinum toxin complex crosses the intestinal epithelial barrier via M cell, Toxins 2012, Miami Beach, USA, 5-8 Dec. 2012

Non-Patent Document 6: J Cell Biol. 2010 May 10; 189(4): 691-700

Non-Patent Document 7: J Biol Chem. 2013 Dec. 6; 288 (49): 35617-25

SUMMARY OF THE INVENTION

Problems to be Solved by the Invention

Accordingly, an object of the present invention is to provide an adjuvant for a mucosal vaccine inducing a sufficient immune response in a mucosal membrane and having high safety.

Means for Solving the Problem

The present inventors focused on hemagglutinin (HA), that is, a non-toxic component of botulinum toxin, and mice were transnasally administered, in combination with an influenza HA antigen, with a wild-type botulinum type B HA (wild-type BHA) complex composed of HA subcomponents (HA1, HA2 and HA3), a mutant botulinum type B HA (mutant BHA) complex obtained by causing mutation in HA3, a wild-type botulinum type A HA (wild-type AHA) complex, and a mutant botulinum type A HA (mutant AHA) complex obtained by causing mutation in HA3. As a result, it was confirmed that production of an IgG antibody in a serum and production of a secretory IgA antibody on a mucosal membrane were accelerated by the administration of all of these complexes, that both the mucosal immunity and the systemic immunity were induced, and that the administration does not affect innate immunity (such as production of IL-6) caused by CpG or LPS stimulation, and thus, they discovered that the aforementioned protein complexes are effective as a non-inflammatory adjuvant for a mucosal vaccine. Furthermore, since the mutant BHA and the mutant AHA do not affect intercellular adhesion forming a mucosal barrier differently from the wild-type BHA and the wild-type AHA, there is no possibility of a foreign matter such as a molecule that induces inflammation entering a deep part of a body through an intercellular space otherwise formed when the intercellular adhesion is disrupted, and hence these are safer adjutants for a mucosal vaccine. Thus, the present invention was accomplished.

The present invention encompasses the following:

(1) An adjuvant comprising a protein complex composed of hemagglutinin (HA) subcomponents HA1, HA2 and HA3 of botulinum toxin, wherein the subcomponent HA1 is:

(a) a protein which comprises a sequence of amino acids at positions 7 to 294 of the amino acid sequence shown in SEQ ID NO: 1; or (b) a protein which comprises an amino acid sequence including a deletion, substitution or addition of one to several amino acids, with respect to a sequence of amino acids at positions 7 to 294 of the amino acid sequence shown in SEQ ID NO: 1, and has equivalent activity to the protein (a), the subcomponent HA2 is:

(c) a protein which comprises a sequence of amino acids at positions 2 to 146 of the amino acid sequence shown in SEQ ID NO: 2; or (d) a protein which comprises an amino acid sequence including a deletion, substitution or addition of one to several amino acids, with respect to a sequence of amino acids at positions 2 to 146 of the amino acid sequence shown in SEQ ID NO: 2, and has equivalent activity to the protein (c), and the subcomponent HA3 is:

(e) a protein which comprises an amino acid sequence including a substitution of at least one or more amino acids among leucine at position 473, methionine at position 508, phenylalanine at position 569, and lysine at position 607 with other amino acid(s), with respect to a sequence of amino acids at positions 19 to 626 of the amino acid sequence shown in SEQ ID NO: 3; or (f) a protein which comprises an amino acid sequence including a deletion, substitution, or addition of one to several amino acids at position(s) other than the amino acids at positions 473, 508, 569, and 607, with respect to the amino acid sequence of the protein (e), and has equivalent activity to the protein (e).

(2) An adjuvant comprising a protein complex composed of hemagglutinin (HA) subcomponents HA1, HA2 and HA3 of botulinum toxin, wherein the subcomponent HA1 is:

(g) a protein which comprises a sequence of amino acids at positions 6 to 293 of the amino acid sequence shown in SEQ ID NO: 15; or (h) a protein which comprises an amino acid sequence including a deletion, substitution or addition of one to several amino acids, with respect to a sequence of amino acids at positions 6 to 293 of the amino acid sequence shown in SEQ ID NO: 15, and has equivalent activity to the protein (g), the subcomponent HA2 is:

(i) a protein which comprises a sequence of amino acids at positions 2 to 146 of the amino acid sequence shown in SEQ ID NO: 16; or (j) a protein which comprises an amino acid sequence including a deletion, substitution or addition of one to several amino acids, with respect to a sequence of amino acids at positions 2 to 146 of the amino acid sequence shown in SEQ ID NO: 16, and has equivalent activity to the protein (i), and the subcomponent HA3 is:

(k) a protein which comprises an amino acid sequence including a substitution of at least one or more amino acids among leucine at position 473, methionine at position 508, phenylalanine at position 569, and lysine at position 607 with other amino acid(s), with respect to a sequence of amino acids at positions 20 to 626 of the amino acid sequence shown in SEQ ID NO: 17; or (l) a protein which comprises an amino acid sequence including a deletion, substitution, or addition of one to several amino acids at position(s) other than the amino acids at positions 473, 508, 569, and 607, with respect to the amino acid sequence of the protein (k), and has equivalent activity to the protein (k).

(3) The adjuvant according to (1) or (2), wherein the subcomponent HA3 is a protein which comprises an amino acid sequence including a substitution of any one of leucine at position 473, methionine at position 508, phenylalanine at 569, and lysine at position 607 with another amino acid, with respect to the amino acid sequence shown in SEQ ID NO: 3 or SEQ ID NO: 17.

(4) The adjuvant according to (3), wherein the another amino acid is alanine.

(5) The adjuvant according to any one of (1) to (4), to be used simultaneously with a vaccine antigen or before or after administering a vaccine antigen.
(6) The adjuvant according to (5), wherein the vaccine antigen is a subunit antigen or an inactivated antigen.
(7) The adjuvant according to (5) or (6), wherein the vaccine antigen is derived from a pathogen causing a mucosal infection.
(8) The adjuvant according to (7), wherein the pathogen causing the mucosal infection is a virus or a bacterium.
(9) The adjuvant according to (8), wherein the virus is influenza virus, human immunodeficiency virus (HIV), chickenpox virus, measles virus, rubella virus, mumps virus, poliovirus, rotavirus, norovirus, adenovirus, herpes virus, RS virus, dengue virus, Japanese encephalitis virus, severe acute respiratory syndrome (SARS) virus, cytomegalovirus, Epstein-Barr (EB) virus, or hepatitis virus (type A, type B or type C).
(10) The adjuvant according to (8), wherein the bacterium is *Bordetella pertussis, Neisseria meningitidis, Haemophilus influenzae* Type b, *Diplococcus pneumoniae, Mycobacterium tuberculosis, Clostridium tetani* or *Vibrio cholerae*.
(11) The adjuvant according to any one of (1) to (10), to be transmucosally administered.
(12) The adjuvant according to claim (11), wherein transmucosal administration is intranasal administration.
(13) A mucosal vaccine preparation comprising a vaccine antigen and the adjuvant according to any one of (1) to (12).

Effects of the Invention

When an adjuvant of the present invention is administered to a mucosal membrane in a nasal cavity or the like in combination with an antigen derived from a pathogen causing a mucosal infection, such as an influenza virus, production of an IgG antibody in a serum and production of a secretory IgA antibody on the mucosal membrane are accelerated, and antigen-specific systemic and mucosal immune responses are enhanced. Accordingly, the adjuvant of the present invention is useful as an adjuvant for a mucosal vaccine against diseases of the respiratory apparatus or the digestive apparatus. In addition, the adjuvant of the present invention uses subcomponents of hemagglutinin (HA), which is a non-toxic botulinum toxin component, does not affect innate immunity, and is not liable to cause inflammations after the mucosal administration, and in addition, since it does not affect E-cadherin intercellular adhesion forming a mucosal barrier, there is no possibility of a foreign matter such as an inflammation inducing molecule entering a deep part of a body through an intercellular space otherwise formed when the intercellular adhesion is disrupted, and therefore, it is extremely highly safe.

This application claims the benefit of priority of the prior Japanese Patent Application No. 2014-116241, filed on Jun. 4, 2014, the entire contents of which are incorporated herein by reference.

BRIEF DESCRIPTION OF THE DRAWINGS

FIG. 1 illustrates an amino acid sequence of recombinant botulinum type B HA1-3 used to prepare a wild-type botulinum type B HA (BHA) complex in Example 1. Each underlined region corresponds to a vector-derived amino acid sequence (including FLAG tag sequence: SEQ ID NO: 7; and Strep tag sequence: SEQ ID NO: 8).
FIG. 2 illustrates an amino acid sequence of recombinant botulinum type A HA1-3 used to prepare a wild-type botulinum type A HA (AHA) complex in Example 1. Each underlined region corresponds to a vector-derived amino acid sequence (including FLAG tag sequence: SEQ ID NO: 21 and SEQ ID NO: 7; and Strep tag sequence: SEQ ID NO: 22).
FIG. 3 illustrates an amino acid sequence of recombinant botulinum type B HA3 used to prepare mutant (L473A, M508A, F569A and K607A) botulinum type B HA (BHA) complexes in Example 1. Each underlined region corresponds to a vector-derived amino acid sequence (including Strep tag sequence: SEQ ID NO: 8), and each amino acid surrounded with a square corresponds to an amino acid that is mutated (subjected to amino acid substitution).
FIG. 4 illustrates an amino acid sequence of recombinant botulinum type A HA3 used to prepare mutant (L473A, M508A, F569A and K607A) botulinum type A HA (AHA) complexes in Example 1. Each underlined region corresponds to a vector-derived amino acid sequence (including Strep tag sequence: SEQ ID NO: 22), and each amino acid surrounded with a square corresponds to an amino acid that is mutated (subjected to amino acid substitution).
FIG. 5 illustrates purification of a wild-type BHA complex and a mutant (K607A) BHA complex via gel filtration column chromatography.
FIG. 15 illustrates the activation of innate immunity (TNF-α/IL-6 production) caused by the mutant (K607A) BHA complex and its subcomponents.

FIG. 18 illustrates measurement results, obtained by ELISA, for production amounts of influenza-antigen-specific IgG (A) in blood and influenza-antigen-specific IgA (B) in a nasal cavity lavage fluid (SV: a group administered with influenza split vaccine alone; SV+AHAwt: a group administered with influenza split vaccine and the wild-type AHA complex; SV+AHA L473A: a group administered with influenza split vaccine and the mutant (L473A) AHA complex; SV+AHA M508A: a group administered with influenza split vaccine and the mutant (M508A) AHA complex; SV+AHA F569A: a group administered with influenza split vaccine and the mutant (F569A) AHA complex; SV+AHA K607A: a group administered with influenza split vaccine and the mutant (K607A) AHA complex; SV+BHAwt: a group administered with influenza split vaccine and the wild-type BHA complex; SV+BHA K607A: a group administered with influenza split vaccine and the mutant (K607A) BHA complex; SV+CTB: a group administered with influenza split vaccine and cholera toxin B subunit; NC: a non-administered group).

EMBODIMENT FOR CARRYING OUT THE INVENTION

Figure 6:
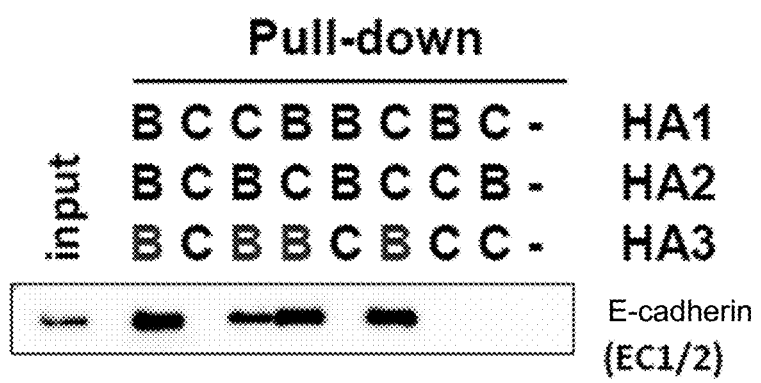
FIG. 6 illustrates the result of identification of subcomponents significant for interaction between the BHA complex and E-cadherin.

An adjuvant for a mucosal vaccine of the present invention (hereafter simply referred to as the "adjuvant") is a protein complex composed of HA1, HA2 and HA3, which are hemagglutinin (HA) subcomponents of botulinum toxin. The term "adjuvant" used herein refers to a substance that is administered for purpose of enhancing the immunogenicity of a vaccine antigen.

Botulinum toxins are classified into type A to type G in accordance with the different antigenicities of toxins produced by botulinum (*Clostridium botulinum*), and a botulinum toxin complex used for the adjuvant of the present invention is preferably of type A or type B.

The HA1, the HA2 and the HA3 composing the protein complex contained in the adjuvant of the present invention are preferably, respectively, a protein which comprises a sequence of amino acids at positions 7 to 294 of the amino acid sequence shown in SEQ ID NO: 1, a protein which comprises a sequence of amino acids at positions 2 to 146 of the amino acid sequence shown in SEQ ID NO: 2, and a protein which comprises an amino acid sequence including a substitution of at least one or more amino acids among leucine at position 473, methionine at position 508, phenylalanine at position 569, and lysine at position 607 with other amino acid(s), with respect to a sequence of amino acids at positions 19 to 626 of the amino acid sequence shown in SEQ ID NO: 3; or, respectively, a protein which comprises a sequence of amino acids at positions 6 to 293 of the amino acid sequence shown in SEQ ID NO: 15, a protein which comprises a sequence of amino acids at positions 2 to 146 of the amino acid sequence shown in SEQ ID NO: 16, and a protein which comprises an amino acid sequence including a substitution of at least one or more amino acids among leucine at position 473, methionine at position 508, phenylalanine at position 569, and lysine at position 607 with other amino acid(s), with respect to a sequence of amino acids at positions 20 to 626 of the amino acid sequence shown in SEQ ID NO: 17; or more preferably, respectively, a protein which consists of a sequence of amino acids at positions 7 to 294 of the amino acid sequence shown in SEQ ID NO: 1, a protein which consists of a sequence of amino acids at positions 2 to 146 of the amino acid sequence shown in SEQ ID NO: 2, and a protein which consists of an amino acid sequence including a substitution of at least one or more amino acids among leucine at position 473, methionine at position 508, phenylalanine at position 569, and lysine at position 607 with other amino acid(s), with respect to a sequence of amino acids at positions 19 to 626 of the amino acid sequence shown in SEQ ID NO: 3; or, respectively, a protein which consists of a sequence of amino acids at positions 6 to 293 of the amino acid sequence shown in SEQ ID NO: 15, a protein which consists of a sequence of amino acids at positions 2 to 146 of the amino acid sequence shown in SEQ ID NO: 16, and a protein which consists of an amino acid sequence including a substitution of at least one or more amino acids among leucine at position 473, methionine at position 508, phenylalanine at position 569, and lysine at position 607 with other amino acid(s), with respect to a sequence of amino acids at positions 20 to 626 of the amino acid sequence shown in SEQ ID NO: 17. In the present invention, the amino acids at the specific positions in the amino acid sequence shown in SEQ ID NO: 3 or SEQ ID NO: 17 may be substituted at least one of, at arbitrary two or three of, or at all of positions 473, 508, 569 and 607.

The HA1, the HA2 and the HA3 composing the protein complex contained in the adjuvant of the present invention are preferably, respectively, a protein which comprises a sequence of amino acids at positions 7 to 294 of the amino acid sequence shown in SEQ ID NO: 1, a protein which comprises a sequence of amino acids at positions 2 to 146 of the amino acid sequence shown in SEQ ID NO: 2, and a protein which comprises an amino acid sequence including a substitution of any one of amino acids among leucine at position 473, methionine at position 508, phenylalanine at position 569, and lysine at position 607 with another amino acid, with respect to a sequence of amino acids at positions 19 to 626 of the amino acid sequence shown in SEQ ID NO: 3; or, respectively, a protein which comprises a sequence of amino acids at positions 6 to 293 of the amino acid sequence shown in SEQ ID NO: 15, a protein which comprises a sequence of amino acids at positions 2 to 146 of the amino acid sequence shown in SEQ ID NO: 16, and a protein which comprises an amino acid sequence including a substitution of any one of amino acids among leucine at position 473, methionine at position 508, phenylalanine at position 569, and lysine at position 607 with another amino acid, with respect to a sequence of amino acids at positions 20 to 626 of the amino acid sequence shown in SEQ ID NO: 17; or more preferably, respectively, a protein which consists of a sequence of amino acids at positions 7 to 294 of the amino acid sequence shown in SEQ ID NO: 1, a protein which consists of a sequence of amino acids at positions 2 to 146 of the amino acid sequence shown in SEQ ID NO: 2, and a protein which consists of an amino acid sequence including a substitution of any one of amino acids among leucine at position 473, methionine at position 508, phenylalanine at position 569, and lysine at position 607 with another amino acid, with respect to a sequence of amino acids at positions 19 to 626 of the amino acid sequence shown in SEQ ID NO: 3; or, respectively, a protein which consists of a sequence of amino acids at positions 6 to 293 of the amino acid sequence shown in SEQ ID NO: 15, a protein which consists of a sequence of amino acids at positions 2 to 146 of the amino acid sequence shown in SEQ ID NO: 16, and a protein which consists of an amino acid sequence including a substitution of any one of amino acids among leucine at position 473, methionine at position 508, phenylalanine at position 569, and lysine at position 607 with another amino acid, with respect to a sequence of amino acids at positions 20 to 626 of the amino acid sequence shown in SEQ ID NO: 17.

Here, the amino acid substitution is not especially limited as long as it does not affect intercellular adhesion and has mucosal adjuvant activity. For example, in order to reduce the influence on the intercellular adhesion of a wild-type botulinum type B HA or type A HA, conservative amino acid substitution meaning that an amino acid at a specific position is substituted by an amino acid similar in the structural, electrical, polarity or hydrophobic properties is not employed but substitution of amino acids different in these properties can be employed.

In the amino acid sequence shown in SEQ ID NO: 3 or SEQ ID NO: 17, an amino acid used for substitution of leucine at position 473, methionine at position 508, phenylalanine at 569 or lysine at position 607 is preferably alanine. Accordingly, particularly preferable examples of the protein complex contained in the adjuvant of the present invention include: a protein which comprises a sequence of amino acids at positions 7 to 294 of the amino acid sequence shown in SEQ ID NO: 1, a protein which comprises a sequence of amino acids at positions 2 to 146 of the amino acid sequence shown in SEQ ID NO: 2, and a protein which comprises an amino acid sequence including a substitution of leucine at position 473 with alanine, with respect to a sequence of amino acids at positions 19 to 626 of the amino acid sequence shown in SEQ ID NO: 3; a protein which comprises a sequence of amino acids at positions 7 to 294 of the amino acid sequence shown in SEQ ID NO: 1, a protein which comprises a sequence of amino acids at positions 2 to 146 of the amino acid sequence shown in SEQ ID NO: 2, and a protein which comprises an amino acid sequence including a substitution of methionine at position 508 with alanine, with respect to a sequence of amino acids at positions 19 to 626 of the amino acid sequence shown in SEQ ID NO: 3; a protein which comprises a sequence of amino acids at positions 7 to 294 of the amino acid sequence shown in SEQ ID NO: 1, a protein which comprises a sequence of amino acids at positions 2 to 146 of the amino acid sequence shown in SEQ ID NO: 2, and a protein which comprises an amino acid sequence including a substitution of phenylalanine at position 569 with alanine, with respect to an sequence of amino acids at positions 19 to 626 of the amino acid sequence shown in SEQ ID NO: 3; a protein which comprises a sequence of amino acids at positions 7 to 294 of the amino acid sequence shown in SEQ ID NO: 1, a protein which comprises a sequence of amino acids at positions 2 to 146 of the amino acid sequence shown in SEQ ID NO: 2, and a protein which comprises an amino acid sequence including a substitution of lysine at position 607 with alanine, with respect to a sequence of amino acids at positions 19 to 626 of the amino acid sequence shown in SEQ ID NO: 3.

Other preferable examples of the protein complex contained in the adjuvant of the present invention include: a protein which comprises a sequence of amino acids at positions 6 to 293 of the amino acid sequence shown in SEQ ID NO: 15, a protein which comprises a sequence of amino acids at positions 2 to 146 of the amino acid sequence shown in SEQ ID NO: 16, and a protein which comprises an amino acid sequence including a substitution of leucine at position 473 with alanine, with respect to a sequence of amino acids at positions 20 to 626 of the amino acid sequence shown in SEQ ID NO: 17; a protein which comprises a sequence of amino acids at positions 6 to 293 of the amino acid sequence shown in SEQ ID NO: 15, a protein which comprises a sequence of amino acids at positions 2 to 146 of the amino acid sequence shown in SEQ ID NO: 16, and a protein which comprises an amino acid sequence including a substitution of methionine at position 508 with alanine, with respect to a sequence of amino acids at positions 20 to 626 of the amino acid sequence shown in SEQ ID NO: 17; a protein which comprises a sequence of amino acids at positions 6 to 293 of the amino acid sequence shown in SEQ ID NO: 15, a protein which comprises a sequence of amino acids at positions 2 to 146 of the amino acid sequence shown in SEQ ID NO: 16, and a protein which comprises an amino acid sequence including a substitution of phenylalanine at position 569 with alanine, with respect to a sequence of amino acids at positions 20 to 626 of the amino acid sequence shown in SEQ ID NO: 17; a protein which comprises a sequence of amino acids at positions 6 to 293 of the amino acid sequence shown in SEQ ID NO: 15, a protein which comprises a sequence of amino acids at positions 2 to 146 of the amino acid sequence shown in SEQ ID NO: 16, and a protein which comprises an amino acid sequence including a substitution of lysine at position 607 with alanine, with respect to a sequence of amino acids at positions 20 to 626 of the amino acid sequence shown in SEQ ID NO: 17.

Most preferable examples of the protein complex contained in the adjuvant of the present invention include:
a protein which consists of a sequence of amino acids at positions 7 to 294 of the amino acid sequence shown in SEQ ID NO: 1, a protein which consists of a sequence of amino acids at positions 2 to 146 of the amino acid sequence shown in SEQ ID NO: 2, and a protein which consists of an amino acid sequence including a substitution of leucine at position 473 with alanine, with respect to a sequence of amino acids at positions 19 to 626 of the amino acid sequence shown in SEQ ID NO: 3; a protein which consists of a sequence of amino acids at positions 7 to 294 of the amino acid sequence shown in SEQ ID NO: 1, a protein which consists of a sequence of amino acids at positions 2 to 146 of the amino acid sequence shown in SEQ ID NO: 2, and a protein which consists of an amino acid sequence including a substitution of methionine at position 508 with alanine, with respect to a sequence of amino acids at positions 19 to 626 of the amino acid sequence shown in SEQ ID NO: 3; a protein which consists of a sequence of amino acids at positions 7 to 294 of the amino acid sequence shown in SEQ ID NO: 1, a protein which consists of a sequence of amino acids at positions 2 to 146 of the amino acid sequence shown in SEQ ID NO: 2, and a protein which consists of an amino acid sequence including a substitution of phenylalanine at position 569 with alanine, with respect to a sequence of amino acids at positions 19 to 626 of the amino acid sequence shown in SEQ ID NO: 3; a protein which consists of a sequence of amino acids at positions 7 to 294 of the amino acid sequence shown in SEQ ID NO: 1, a protein which consists of a sequence of amino acids at positions 2 to 146 of the amino acid sequence shown in SEQ ID NO: 2, and a protein which consists of an amino acid sequence including a substitution of lysine at position 607 with alanine, with respect to a sequence of amino acids at positions 19 to 626 of the amino acid sequence shown in SEQ ID NO: 3.

Other most preferable examples of the protein complex contained in the adjuvant of the present invention include: a protein which consists of a sequence of amino acids at positions 6 to 293 of the amino acid sequence shown in SEQ ID NO: 15, a protein which consists of a sequence of amino acids at positions 2 to 146 of the amino acid sequence shown in SEQ ID NO: 16, and a protein which consists of an amino acid sequence including a substitution of leucine at position 473 with alanine, with respect to a sequence of amino acids at positions 20 to 626 of the amino acid sequence shown in SEQ ID NO: 17; a protein which consists of a sequence of amino acids at positions 6 to 293 of the amino acid sequence shown in SEQ ID NO: 15, a protein which consists of a sequence of amino acids at positions 2 to 146 of the amino acid sequence shown in SEQ ID NO: 16, and a protein which consists of an amino acid sequence including a substitution of methionine at position 508 with alanine, with respect to a sequence of amino acids at positions 20 to 626 of the amino acid sequence shown in SEQ ID NO: 17; a protein which consists of a sequence of amino acids at positions 6 to 293 of the amino acid sequence shown in SEQ ID NO: 15, a protein which consists of a sequence of amino acids at positions 2 to 146 of the amino acid sequence shown in SEQ ID NO: 16, and a protein which consists of an amino acid sequence including a substitution of phenylalanine at position 569 with alanine, with respect to a sequence of amino acids at positions 20 to 626 of the amino acid sequence shown in SEQ ID NO: 17; a protein which consists of a sequence of amino acids at positions 6 to 293 of the amino acid sequence shown in SEQ ID NO: 15, a protein which consists of a sequence of amino acids at positions 2 to 146 of the amino acid sequence shown in SEQ ID NO: 16, and a protein which consists of an amino acid sequence including a substitution of lysine at position 607 with alanine, with respect to a sequence of amino acids at positions 20 to 626 of the amino acid sequence shown in SEQ ID NO: 17.

Herein, the amino acid substitution is sometimes expressed, assuming that the N-terminal of an amino acid sequence of interest corresponds to the 1st position, by putting a position number of a wild type amino acid residue on the left side and putting a position number of an amino acid residue to be used for modification on the right side of a position number of an amino acid to be substituted. For example, in the amino acid sequence shown in SEQ ID NO: 3, if lysine at position 607 (K) is substituted with alanine (A), the resultant sequence is expressed as BHA3 K607A or K607A.

Besides, proteins homologous to the six proteins composing the protein complexes, that is, a protein which comprises a sequence of amino acids at positions 7 to 294 of the amino acid sequence shown in SEQ ID NO: 1, a protein which comprises a sequence of amino acids at positions 2 to 146 of the amino acid sequence shown in SEQ ID NO: 2, a protein which comprises an amino acid sequence including a substitution of at least one or more amino acids among leucine at position 473, methionine at position 508, phenylalanine at position 569, and lysine at position 607 with other amino acid(s), with respect to a sequence of amino acids at positions 19 to 626 of the amino acid sequence shown in SEQ ID NO: 3, a protein which comprises a sequence of amino acids at positions 6 to 293 of the amino acid sequence shown in SEQ ID NO: 15, a protein which comprises a sequence of amino acids at positions 2 to 146 of the amino acid sequence shown in SEQ ID NO: 16, and a protein which comprises an amino acid sequence including a substitution of at least one or more amino acids among leucine at position 473, methionine at position 508, phenylalanine at position 569, and lysine at position 607 with other amino acid(s), with respect to a sequence of amino acids at positions 20 to 626 of the amino acid sequence shown in SEQ ID NO: 17, may be used as long as the homologous proteins respectively have equivalent activities. Hereinafter, the amino acid sequence in which at least one or more of positions of 473, 508, 569, and 607 of the amino acid sequence shown in SEQ ID NO: 3 is substituted with other amino acid(s) will be designated as the "modified amino acid sequence of SEQ ID NO: 3", and the amino acid sequence in which at least one or more of positions of 473, 508, 569, and 607 of the amino acid sequence shown in SEQ ID NO: 17 is substituted with other amino acid(s) will be designated as the "modified amino acid sequence of SEQ ID NO: 17".

Here, the term "having equivalent activity" means that a protein complex composed of the homologous proteins has mucosal adjuvant activity equivalent to or has mucosal adjuvant activity, without affecting the intercellular adhesion, equivalent to that of the protein complex composed of a protein which comprises a sequence of amino acids at positions 7 to 294 of the amino acid sequence shown in SEQ ID NO: 1, a protein which comprises a sequence of amino acids at positions 2 to 146 of the amino acid sequence shown in SEQ ID NO: 2, and a protein which comprises an amino acid sequence including a substitution of at least one or more amino acids among leucine at position 473, methionine at position 508, phenylalanine at position 569, and lysine at position 607 with other amino acid(s), with respect to a sequence of amino acids at positions 19 to 626 of the amino acid sequence shown in SEQ ID NO: 3; or a protein which comprises a sequence of amino acids at positions 6 to 293 of the amino acid sequence shown in SEQ ID NO: 15, a protein which comprises a sequence of amino acids at positions 2 to 146 of the amino acid sequence shown in SEQ ID NO: 16, and a protein which comprises an amino acid sequence including a substitution of at least one or more amino acids among leucine at position 473, methionine at position 508, phenylalanine at position 569, and lysine at position 607 with other amino acid(s), with respect to a sequence of amino acids at positions 20 to 626 of the amino acid sequence shown in SEQ ID NO: 17.

The term "mucosal adjuvant activity" refers to activity that enhances, when the adjuvant is administered transmucosally in combination with a vaccine antigen, production of an antibody specific to the antigen in both the mucosal and systemic systems. Preferably, it refers to activity that slightly affects the innate immunity, and enhances the production of the antibody specific to the antigen in both the mucosal and systemic systems, and more preferably, it refers to activity that does not affect the innate immunity, and enhances the production of the antibody specific to the antigen in both the mucosal and systemic systems. Examples of such homologous proteins encompass a protein which consists of an amino acid sequence including a deletion, substitution or addition of one to several amino acids, with respect to a sequence of amino acids at positions 7 to 294 of the amino acid sequence shown in SEQ ID NO: 1, with respect to a sequence of amino acids at positions 2 to 146 of the amino acid sequence shown in SEQ ID NO: 2, or at positions other than the amino acids at position 473, at position 508, at position 569, and at position 607, with respect to the modified acid sequence of SEQ ID NO: 3, or a protein which consists of an amino acid sequence including a deletion, substitution or addition of one to several amino acids, with respect to a sequence of amino acids at positions 6 to 293 of the amino acid sequence shown in SEQ ID NO: 15, with respect to a sequence of amino acids at positions 2 to 146 of the amino acid sequence shown in SEQ ID NO: 16, or at positions other than the amino acids at position 473, at position 508, at position 569, and at position 607, with respect to the modified acid sequence of SEQ ID NO: 17. Here, the range of "one to several" refers to the number of amino acids that can be deleted, substituted or added by a known method for producing a mutant protein, such as site-directed mutagenesis, and as long as the activity described above is retained, the number is not limited, but is 1 to 30, 1 to 25, 1 to 20, 1 to 15, or 1 to 12, preferably 1 to 10, 1 to 9, 1 to 8, 1 to 7 or 1 to 6, and more preferably 1 to 5, 1 to 4, 1 to 3 or 1 to 2. The "substitution" is not especially limited as long as the resultant has the equivalent activity, and is, for example, the conservative amino acid substitution. The conservative amino acid substitution means substitution of amino acids similar to each other in, for example, the structural, the electrical, the polarity or the hydrophobic properties. Such properties can be classified in accordance with, for example, similarity in the amino acid side chain, and can be classified into the following groups: An amino acid group having an acidic side chain (aspartic acid and glutamic acid), an amino acid group having a basic side chain (lysine, arginine and histidine), an amino acid group having a nonpolar side chain (alanine, valine, leucine, isoleucine, proline, phenylalanine, methionine and tryptophan), an amino acid group having a side chain with no charging polarity (glycine, asparagine, glutamine, cysteine, serine, threonine and tyrosine), an amino acid group having a hydrophobic side chain (alanine, valine, leucine, isoleucine, proline, phenylalanine and methionine), an amino acid group having a branched side chain (threonine, valine, leucine and isoleucine), an amino acid group having an aromatic side chain (tyrosine, tryptophan, phenylalanine and histidine), an amino acid group having a hydroxymethylene group (serine and threonine), a group having an amide-containing side chain (asparagine and glutamine) and the like.

Besides, each of the following eight groups includes amino acids regarded to be conservatively mutually replaceable in this technical field (for example, see Creighton, Proteins 1984).

1) alanine and glycine;
2) aspartic acid and glutamic acid;
3) asparagine and glutamine;
4) arginine and lysine;
5) isoleucine, leucine, methionine and valine;
6) phenylalanine, tyrosine and tryptophan;
7) serine and threonine; and
8) cysteine and methionine.

Besides, a homologous protein may be a protein which comprises an amino acid sequence having 90% or more sequence identity to a sequence of amino acids at positions 7 to 294 of the amino acid sequence shown in SEQ ID NO: 1, a sequence of amino acids at positions 2 to 146 of the amino acid sequence shown in SEQ ID NO: 2, or the modified amino acid sequence of SEQ ID NO: 3, or a protein which comprises an amino acid sequence having 90% or more sequence identity to a sequence of amino acids at positions 6 to 293 of the amino acid sequence shown in SEQ ID NO: 15, a sequence of amino acids at positions 2 to 146 of the amino acid sequence shown in SEQ ID NO: 16, or the modified amino acid sequence of SEQ ID NO: 17, and is preferably a protein which consists of an amino acid sequence having 90% or more sequence identity to a sequence of amino acids at positions 7 to 294 of the amino acid sequence shown in SEQ ID NO: 1, a sequence of amino acids at positions 2 to 146 of the amino acid sequence shown in SEQ ID NO: 2, or the modified amino acid sequence of SEQ ID NO: 3, or a protein which consists of an amino acid sequence having 90% or more sequence identity to a sequence of amino acids at positions 6 to 293 of the amino acid sequence shown in SEQ ID NO: 15, a sequence of amino acids at positions 2 to 146 of the amino acid sequence shown in SEQ ID NO: 16, or the modified amino acid sequence of SEQ ID NO: 17. Here, the term "90% or more sequence identity" refers to sequence identity of preferably 95% or more, more preferably 97% or more, and most preferably 98% or more. The sequence identity of an amino acid sequence can be determined through a FASTA search or BLAST search method.

A method for producing the adjuvant of the present invention is not especially limited. Each of the aforementioned protein complexes may be derived from nature, or alternatively, proteins composing the protein complex may be produced by genetic recombination, so as to use the resultant proteins for forming the complex. If it is produced by the genetic recombination, genes respectively encoding the proteins may be used in a known method. Specifically, wild-type HA1, HA2 and HA3 can be produced by constructing expression vectors containing genes respectively encoding the amino acid sequences shown in SEQ ID NOs: 1, 2 and 3 (whose nucleotide sequences are shown in SEQ ID NOs: 4, 5 and 6, respectively), or genes respectively encoding the amino acid sequences shown in SEQ ID Nos: 15, 16 and 17 (whose nucleotide sequences are shown in SEQ ID Nos: 18, 19 and 20), introducing the expression vectors into adequate host cells, and culturing the host cells. Alternatively, as for a mutant HA3 having the amino acid substitution at the specific position in the amino acid sequence shown in SEQ ID NO: 3 or SEQ ID NO: 17, a desired point mutant sequence can be produced by site-directed mutagenesis employing both PCR using a complementary primer pair and a treatment using DpnI restriction enzyme (Gene 1994 Dec. 30; 151(1-2): 119-23).

For example, if a mutant HA3 in which lysine (K) in position 607 in the amino acid sequence shown in SEQ ID NO: 3 is substituted with alanine (A) is to be produced, the production is performed by amplifying, by the PCR, an expression plasmid encoding wild-type HA3 by using a complementary primer pair in which "aaa" (a codon encoding lysine) is changed to "get" (a codon encoding alanine). Alternatively, the HA1, the HA2 and the HA3 can be produced by chemical synthesis performed on the basis of their amino acid sequences.

Homologous proteins of the HA1, the HA2 and the HA3 can be also produced by a well-known recombinant DNA method by, for example, using gene encoding the homologous proteins obtained by subjecting genes respectively encoding the amino acid sequences shown in SEQ ID NOs: 1, 2 and 3 or SEQ ID Nos: 15, 16 and 17 to the site-directed mutagenesis. The production of these proteins can be easily carried out specifically with reference to a basic literature such as Molecular Cloning 2nd Ed., Cold Spring Harbor Laboratory Press, 1989.

The thus produced HA1, HA2 and HA3 proteins may be incubated in a solvent such as a phosphate buffer for 2 to 8 hours, preferably 3 to 5 hours, and more preferably 3 hours at 25° C. to 40° C., and preferably 37° C., so as to compose the complex. Alternatively, a fusion protein may be prepared from the HA1, HA2 and HA3 proteins. As a method for producing a fusion protein, a known method in which DNA fragments respectively encoding the HA1, HA2 and HA3 proteins are bound to be in-frame with one another, the resultant is introduced into an adequate expression vector, and the resultant is transcribed and translated with the aid of an adequate host so as to express a protein may be employed.

In general, the adjuvant of the present invention is administered to an organism simultaneously with a vaccine antigen, or may be administered before the administration of a vaccine antigen or after the administration of an antigen. If the adjuvant is administered simultaneously with a vaccine antigen, the adjuvant may be administered substantially simultaneously with the vaccine, and for example, the adjuvant and the vaccine antigen may be administered to the target at exactly the same time, or may be continuously administered within a given period of time (preferably within several minutes).

The vaccine antigen is preferably an inactivated antigen or a subunit antigen. The inactivated antigen refers to an antigen of a pathogen (such as a virus or a bacterium) deprived of infectivity, and examples thereof include virions, that is, complete virus particles, incomplete virus particles, virion-constituting particles, virus nonstructural proteins, antigens to prevent infections, and neutralizing epitopes. Examples of a treatment for the inactivation include physical treatments (with x-rays, heat, ultrasound and the like) and chemical treatments (with formalin, mercury, alcohol, chlorine and the like). The term "subunit vaccine" refers to a vaccine containing merely a specific antigen (an antigen to prevent an infection) as an effective vaccine component among various types of antigens contained in inactivated vaccines. An example of a subunit vaccine against, for example, the influenza virus is a vaccine containing merely hemagglutinin (HA) and neuraminidase (NA) that are purified surface antigens.

The vaccine antigen is not especially limited, provided that the vaccine antigen is capable of inducing a mucosal immune response together with the adjuvant of the present invention, and the antigen is typically derived from a pathogen causing a mucosal infection. The pathogen causing a mucosal infection may be a virus or a bacterium. Examples of the virus include, but are not limited to, influenza virus, human immunodeficiency virus (HIV), chickenpox virus, measles virus, rubella virus, mumps virus, poliovirus, rotavirus, norovirus, adenovirus, herpes virus, RS virus, dengue virus, Japanese encephalitis virus, severe acute respiratory syndrome (SARS) virus, cytomegalovirus, Epstein-Barr (EB) virus and hepatitis virus (type A, type B, or type C). Examples of the bacterium include, but are not limited to, *Bordetella pertussis, Neisseria meningitidis, Haemophilus influenzae* Type b, *Diplococcus pneumoniae, Mycobacterium tuberculosis, Clostridium tetani* and *Vibrio cholerae*. Such antigens derived from pathogens may be derived from nature or artificially prepared via gene recombination or other techniques.

The vaccine antigen includes an allergen used for hyposensitization therapy.

Accordingly, the adjuvant of the present invention can be used also as an adjuvant for an allergen vaccine. An allergen vaccine refers to a vaccine that blocks the function of IgE causing an allergy by producing IgG antibody against an allergen or increases allergen-specific type 1 helper T cells (Th1 cells) in vivo by administering the allergen to an organism, whereby decreasing type 2 helper T cells (Th2 cells) involved in allergy symptoms, and the allergen vaccine is capable of suppressing allergy symptoms via hyposensitization. The type of allergen is not especially limited, and examples include food allergens (such as casein, lactalbumin, lactoglobulin, ovomucoid, ovalbumin and conalbumin), house dust allergens (such as mite allergens), pollen allergens (such as cedar pollen allergens, ragweed allergens and cocksfoot grass allergens), and allergens of animal body hair.

The adjuvant of the present invention is administered transmucosally in combination with the mucosal vaccine antigen. The term "being administered transmucosally" refers to an administration form through a mucosal membrane. Examples of the mucosal membrane include inner walls of hollow organs that lead to the exterior, such as the digestive apparatus, the respiratory apparatus and the urogenital apparatus, and specific examples include the nasal cavity, oral cavity, pharynx, alveolus, air tube, intestinal tract, and vagina, among which the nasal cavity is preferable. Accordingly, examples of the transmucosal administration form include intranasal, intraoral, intra-alveolar, intratracheal, intravaginal, and intrarectal administration, among which the intranasal administration is preferable. The transmucosal administration of the adjuvant and the mucosal vaccine can be performed in an adequate manner in accordance with the site of administration. In the case of transnasal or oral administration, for example, a method of spraying, adding dropwise or applying them to the nasal cavity or oral cavity can be employed. Intra-alveolar administration can be carried out by a method involving the use of an inhaler or a sprayer, or a method of administering a preparation using an aerosolizing agent.

The amount of the adjuvant of the present invention to be administered varies in accordance with the age and the body weight of a subject, the disease type, the route of administration, the administration form, and other conditions, and the adjuvant of the present invention can be administered, simultaneously with a vaccine antigen, in an amount per dosage per adult human of, for example, 10 μg to 100 mg, and preferably 1 μg to 10 mg in employing the oral administration, and 0.1 μg to 100 mg, and preferably 1 μg to 10 mg in employing the transnasal administration. A subject of administration can be adequately determined in accordance with the type of the vaccine antigen used in combination with the adjuvant, and examples thereof include, in addition to a human, non-human mammals, birds, and crustaceans.

A person skilled in the art can easily determine the frequency of administration of the adjuvant of the present invention in combination with a vaccine antigen to a subject by taking, for example, the age, the body weight, the medical history, the clinical course of the subject, the disease type, and other factors into consideration. As in the case of general vaccine preparations, the administration may be carried out at an adequate time before the onset of the disease at the frequency of, in general, one to several instances per day for merely one day, or several times at intervals of one to several weeks. The administration is preferably carried out while observing progress, and booster immunization is preferably carried out at intervals of at least about a week. The intervals of the booster immunization are preferably at least about two weeks. By providing the booster immunization, a more effective infection-protective effect can be expected.

In order to administer the adjuvant of the present invention simultaneously with a vaccine antigen, the adjuvant may be mixed with the vaccine antigen together with a pharmaceutically acceptable carrier suitable for the dosage form, so as to produce a vaccine preparation by any of various known formulation methods.

The amount of the adjuvant to be incorporated into the vaccine preparation can be adequately determined in accordance with the type of vaccine antigen to be mixed. The content of the adjuvant in the preparation is not especially limited, provided that a sufficient antigen immune response can be induced via the transmucosal administration, and such an amount is generally 0.1% to 90% by weight, preferably 0.5% to 80% by weight, and more preferably 1% to 50% by weight based on the entire amount of the preparation.

The dosage form of the mucosal vaccine preparation of the present invention is not especially limited, provided that the mucosal vaccine preparation can be administered transmucosally, and examples thereof include a liquid preparation, a suspension, a spray, and a powder. Various additives that are generally used for a vaccine preparation, such as a solubilizer, an anticoagulant, a viscosity modifier, a pH adjuster, an isotonizing agent, an emulsifier, an antioxidant, a filler, a surfactant, a diluent, a preservative, a stabilizer, a desiccating agent and a moisturizing agent, can be added, if necessary, to the mucosal vaccine preparation of the present invention.

The vaccine preparation of the present invention can be in a liquid form or a dried form, and can be provided in a state where it is contained in a hermetically sealed vial bottle, a syringe, an atomizer, or a sealed ampule.

EXAMPLES

The present invention will now be described in greater detail with reference to examples, but the present invention is not limited thereto. Data obtained in the examples were statistically processed by Student's t-test.

(Example 1) Preparation of Botulinum Type B HA (BHA) Complex and Type A HA (AHA) Complex A. Preparation of Wild-type Botulinum Type B HA (wild-type BHA) Complex and Wild-type Botulinum Type A HA (wild-type AHA) Complex (1) Preparation of Plasmid Genes respectively encoding proteins of the botulinum type B HA subcomponents (BHA1, BHA2 and BHA3) (BHA1: a protein consisting of amino acids in positions 7 to 294 of the amino acid sequence of SEQ ID NO: 1; BHA2: a protein consisting of amino acids in positions 2 to 146 of the amino acid sequence of SEQ ID NO: 2; and BHA3: a protein consisting of amino acids in positions 19 to 626 of the amino acid sequence of SEQ ID NO: 3), and genes respectively encoding proteins of the botulinum type A HA subcomponents (AHA1, AHA2 and AHA3) (AHA1: a protein consisting of amino acids in positions 6 to 293 of the amino acid sequence of SEQ ID NO: 15; AHA2: a protein consisting of amino acids in positions 2 to 146 of the amino acid sequence of SEQ ID NO: 16; and AHA3: a protein consisting of amino acids in positions 20 to 626 of the amino acid sequence of SEQ ID NO: 17) were amplified by the PCR from genomic DNA of the *Clostridium botulinum* B-Okra strain as a template respectively using the following primers.

(Primers for BHA1 Amplification)
BHA1 forward primer:
(SEQ ID NO: 9)
cactataagcttatccaaaattcattaaatg BHA1 reverse primer:
(SEQ ID NO: 10)
gttgataggtaccttatgggttactcatag (Primers for BHA2 Amplification)
BHA2 forward primer:
(SEQ ID NO: 11)
tgaataagctttcagctgaaagaactttc BHA2 reverse primer:
(SEQ ID NO: 12)
cactttggtaccttatattttttcaagtttga (Primers for BHA3 Amplification)
BHA3 forward primer:
(SEQ ID NO: 13)
gaaaaagggtaccaatatagtgatactattg BHA3 reverse primer:
(SEQ ID NO: 14)
cgtgtcgacttaattagtaatatctatatgc (Primers for AHA1 Amplification)
AHA1 forward primer:
(SEQ ID NO: 23)
catgccatggtaatccaaaattcattaaa AHA1 reverse primer:
(SEQ ID NO: 24)
cgggatccttacttgtcatcgtcatccttgtagtctgggttacgaatatt ccatttc (Primers for AHA2 Amplification)
AHA2 forward primer:
(SEQ ID NO: 25)
tgaataagctttcagttgaaagaactttctac AHA2 reverse primer:
(SEQ ID NO: 26)
attggtaccttatattttacaagtttgaac (Primers for AHA3 Amplification)
AHA3 forward primer:
(SEQ ID NO: 27)
aaagttaggtaccctagtgatactattgatttag AHA3 reverse primer:
(SEQ ID NO: 28)
cgtgtcgacttaattagtaatatctatatgc The amplified DNA fragments of the BHA1 and the BHA2 were each inserted into the HindIII-SalI site of pT7-FLAG-1 (Sigma), that of the BHA3 was inserted into the KpnI-SalI site of pET52b(+) (Novagen) (pET-BHA3), that of the AHA1 was inserted into the NcoI-BamHI site of pET25b(+), that of the AHA2 was inserted into the HindIII-KpnI site of pT7-FLAG-1, and that of the AHA3 was inserted into the KpnI-SalI site of pET52b(+).

(2) Protein Expression

The thus prepared plasmids were separately transformed into *E. coli* Rosetta2 (DE3) strains (Novagen). Protein expression was induced using Overnight Express Autoinduction System 1 (Novagen). The protein expression was induced at 30° C. for 36 hours for the BHA1 and the BHA3, and at 18° C. for 40 hours for the BHA2. The protein expression was induced at 30° C. for 36 hours for the AHA1 and the AHA3, and at 18° C. for 40 hours for the AHA2. The *E. coli* strains were collected by centrifugation and stored at −80° C.

(3) Protein Purification and Complex Preparation

The BHA1 and the BHA2 were purified using Anti-FLAG M2 agarose (Sigma). The BHA3 was purified using Strep- Trap HP (GE Healthcare). The amino acid sequences of the purified recombinant proteins FLAG-BHA1, FLAG-BHA2, and Strep-BHA3 are illustrated in FIG. 1. The AHA1 and the AHA2 were purified using Anti-FLAG M2 agarose (Sigma). The AHA3 was purified using StrepTrap HP (GE Healthcare). The amino acid sequences of the purified recombinant proteins AHA1-FLAG, FLAG-AHA2, and Strep-AHA3 are illustrated in FIG. 2. The purified recombinant proteins were respectively mixed at a ratio of BHA1:BHA2:BHA3 of 4:4:1 by mole and at a ratio of AHA1:AHA2:AHA3 of 4:4:1 by mole, and the resultants were incubated at 37° C. for 3 hours, followed by purification with StrepTrap HP, resulting in obtaining a BHA complex (BHA).

B. Preparation of Mutant Botulinum Type B HA (mutant BHA) Complex and Mutant Botulinum Type A HA (mutant AHA) Complex Plasmids for expressing E-cadherin binding deletion mutants of the BHA3 (BHA3 L473A, BHA3 M508A, BHA3 F569A and BHA3 K607A) were obtained through mutation by the PCR using pET-BHA3 as a template. Subsequently, four mutant BHA complexes were obtained in the same manner as described in (2) and (3) above. The amino acid sequences of Strep-BHA3 mutants (L473A, M508A, F569A and K607A) are illustrated in FIG. 3. Also as E-cadherin binding deletion mutants of the AHA3 (AHA3 L473A, AHA3 M508A, AHA3 F569A and AHA3 K607A), four mutant AHA complexes were obtained by a similar method. The amino acid sequences of Strep-AHA3 mutants (L473A, M508A, F569A and K607A) are illustrated in FIG. 4.

C. Gel Filtration Chromatography of Botulinum Type B HA (BHA) Complex and Botulinum Type A HA (AHA) Complex The wild-type BHA complex and the wild-type AHA complex prepared in A. above and the mutant BHA complexes and the mutant AHA complexes prepared in B. above were separated using Superdex 200 10/300 GL (GE Healthcare). In this test, N-terminal FLAG tag HA1, N-terminal FLAG tag HA2, and N-terminal Strep tag HA3 were respectively used for the HA1, the HA2 and the HA3 composing the BHA complex (BHA), and C-terminal FLAG tag HA1, N-terminal FLAG tag HA2 and N-terminal Strep tab HA3 were respectively used for the HA1, the HA2 and the HA3 composing the AHA complex (AHA). Results obtained in the wild-type complex (BHA) and the mutant (K607A) BHA complex are illustrated in FIG. 5.

(Example 2) Study of Subcomponent Significant for Interaction Between BHA Complex and E-Cadherin The botulinum HA complex of serum type B (BHA) has a property of disrupting intercellular adhesion by binding to E-cadherin of a mouse or a human. On the other hand, a botulinum HA of serum type C (CHA) has no E-cadherin binding activity. Therefore, in order to identify a subcomponent significant for the interaction between the BHA complex and E-cadherin, chimeric botulinum HA complexes were prepared with different combinations of subcomponents of the BHA and the CHA, and the interaction with E-cadherin was analyzed by a pull-down assay. In the pull-down assay, each chimeric botulinum HA was adsorbed onto StrepTactin superflow agarose (Novagen), the resultant was reacted with a full length protein of E-cadherin purified from an *E. coli* expression system (EC1/2) or E-cadherin purified using HEK293 cell expression system, and the thus coprecipitated protein was analyzed by Western blotting using an anti-E-cadherin antibody (ECCD-2, Takara). The results are illustrated in FIG. 6. As illustrated in FIG. 6, if the botulinum HA3 subcomponents were of the serum type B, the complex was bound to E-cadherin. In other words, it was suggested that the BHA3 subcomponents are significant for the binding to E-cadherin.

Figure 7:
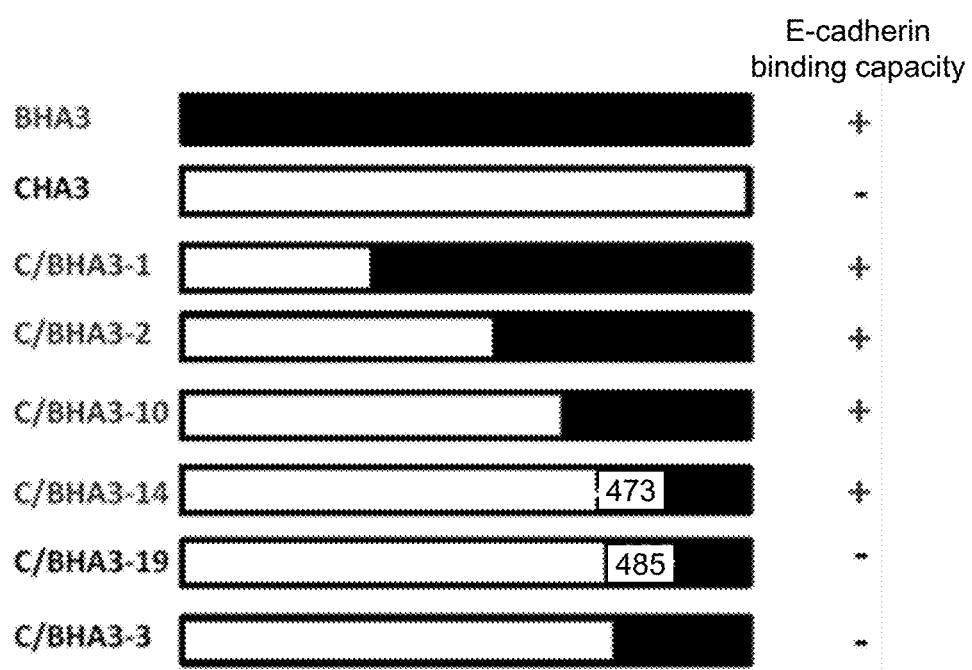
FIG. 7 illustrates the result of identification of a region in BHA3 significant for the interaction with E-cadherin obtained through a pull-down assay using a chimeric botulinum HA3 subcomponent.

(Example 3) Identification of BHA3 Region Significant for Interaction with E-Cadherin In order to examine which region of the BHA3 was significant for the binding to E-cadherin, chimeric botulinum HA3 subcomponents were prepared using the botulinum type C HA3 subcomponents (CHA3) and the botulinum type B HA3 subcomponents (BHA3), and the interaction with E-cadherin was analyzed by a pull-down assay. The results are illustrated in FIG. 7. As illustrated in FIG. 7, a chimeric botulinum HA complex in which a region following position 473 of the BHA3 was fused had E-cadherin binding capacity, but a chimeric botulinum HA complex in which a region following the 485th position of the BHA3 was fused did not have E-cadherin binding capacity. This result suggested that a region from the amino acid at position 473 to the C-terminal of the BHA3 was significant for the interaction with E-cadherin.

Figure 8:
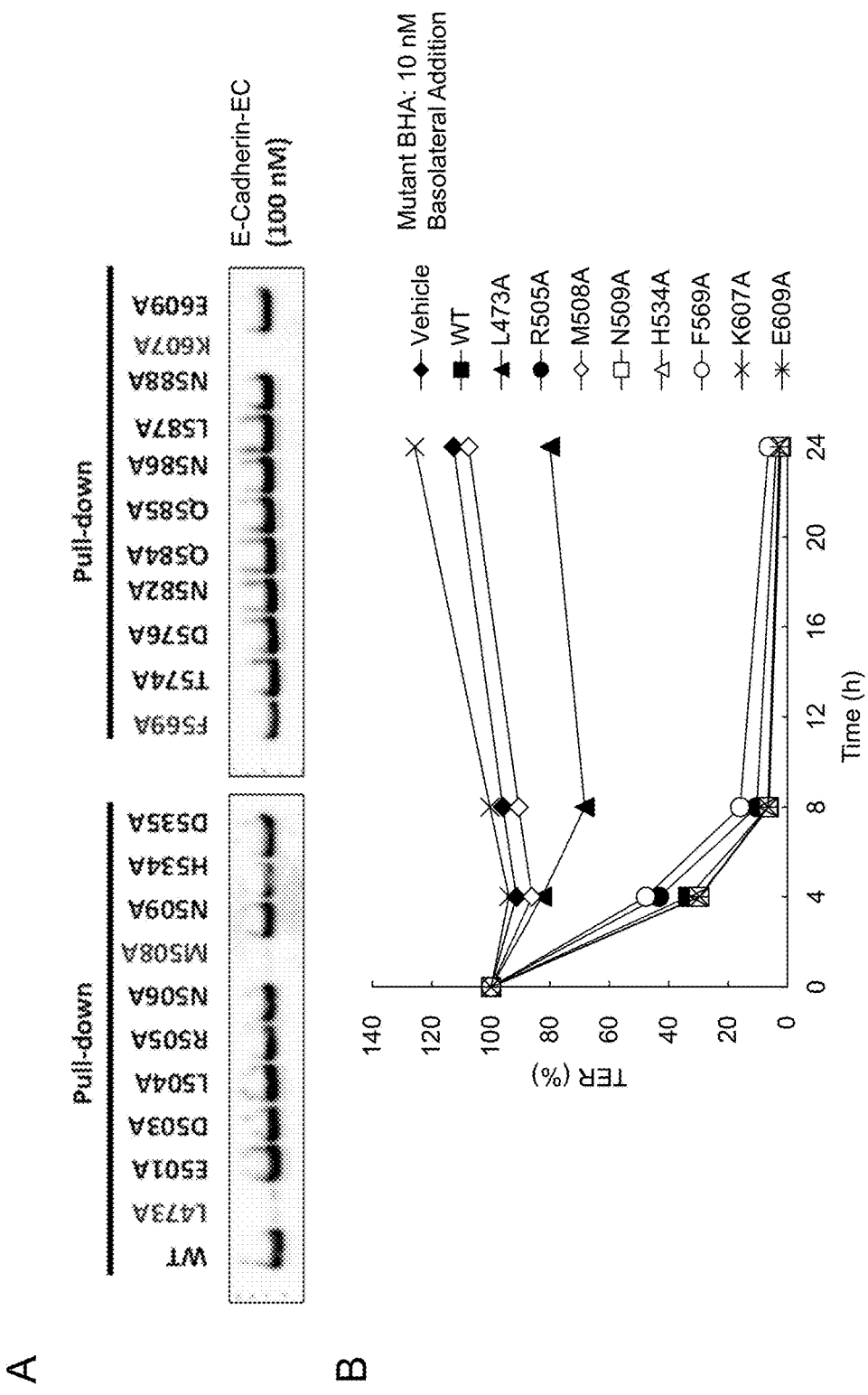
FIG. 8 illustrates the result of identification of an amino acid of the BHA3 significant for the interaction with E-cadherin obtained through a pull-down assay (A) and a TER assay (B) using a mutant BHA complex.

(Example 4) Identification of Amino Acid of BHA3 Significant for Interaction with E-Cadherin It was studied which amino acid among those contained in the region from the amino acid at position 473 to the C-terminal of the botulinum type B HA3 subcomponent (BHA3) was significant for the interaction with E-cadherin. Amino acids different from those contained in the botulinum type C HA (CHA) were selected from the sequence alignment, and BHA3 point mutants in which the selected amino acids were changed to alanine were prepared in the same manner as described in Example 1 (L473A, E501A, D503A, L504A, R505A, N506A, M508A, N509A, H534A, D535A, F569A, T574A, D576A, N582A, Q584A, Q585A, N586A, L587A, N588A, K607A and E609A), and their interactions with E-cadherin were analyzed by a pull-down assay. The results are illustrated in FIG. 8A. As illustrated in FIG. 8A, it was revealed that the E-cadherin binding capacity was attenuated in the mutants L473A, M508A, F569A and K607A. In particular, the E-cadherin binding capacity was presumed to be dramatically lowered in the mutants L473A, M508A and K607A.

Next, in order to examine the influence of the BHA mutants analyzed in FIG. 8A on the cell-cell junction, a transepithelial electrical resistance (TER) assay was performed using Caco-2 cells derived from a human colon cancer. A cell insert was set on a 24-well cell culture plate (transwell plate), and the Caco-2 cells were seeded in the insert. The formation of the intercellular adhesion of the Caco-2 cells was evaluated by measuring a TER value, After the TER value became 2,000 $\Omega \cdot cm^2$ or more, the wild-type BHA complex or each of the mutant BHA complexes (BHA3 point mutants: L473A, R505A, M508A, N509A, H534A, F569A, K607A and E609A) was added to the basolateral side (10 nM), and change of the TER value occurring after the addition was observed over time. The results are illustrated in FIG. 8B. As illustrated in FIG. 8B, the TER value was remarkably decreased in the WT complex 8 hours after the addition, but the TER value was little decreased in the K607A mutant complex and the M508A mutant complex. It was also found that the intercellular adhesion disrupting ability was attenuated in the L473A mutant complex. On the other hand, the TER value decrease was slightly smaller in the F569A, which suggests that this may be an amino acid involved in the interaction with E-cadherin. These results suggested that the L473, M508, F569 and K607 might be amino acids significant for the interaction between the BHA complex and E-cadherin.

Figure 9:
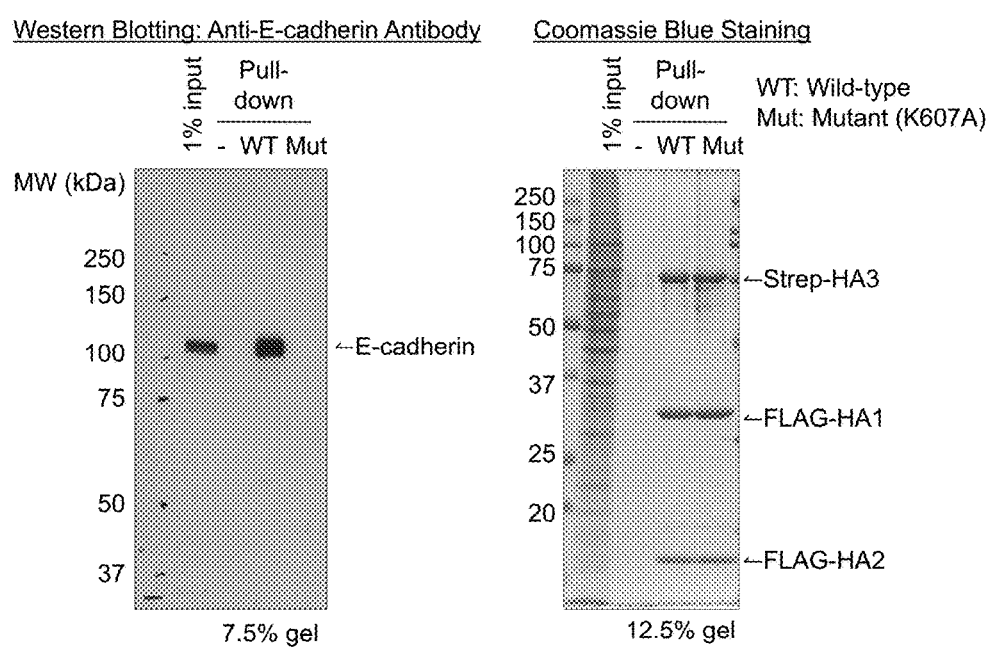
FIG. 9 illustrates the result of a pull-down assay using a wild-type BHA complex and a mutant (K607A) BHA complex.

(Example 5) Interaction Between Wild-Type BHA Complex or Mutant (K607A) BHA Complex and E-Cadherin The interaction between a BHA complex and E-cadherin, that is, a constituent element of the intercellular adhesion, was analyzed by a pull-down assay and Western blotting by mixing a 1% Triton X-100 extraction of Caco-2 cells derived from a human colon cancer and a resin on which a HA complex was immobilized. The results are illustrated in FIG. 9. As illustrated in FIG. 9, it was confirmed that the wild-type BHA complex is directly bound to E-cadherin of the Caco-2 cells. On the other hand, it was revealed that the mutant (K607A) BHA complex is not bound to E-cadherin of the Caco-2 cells.

Figure 10:
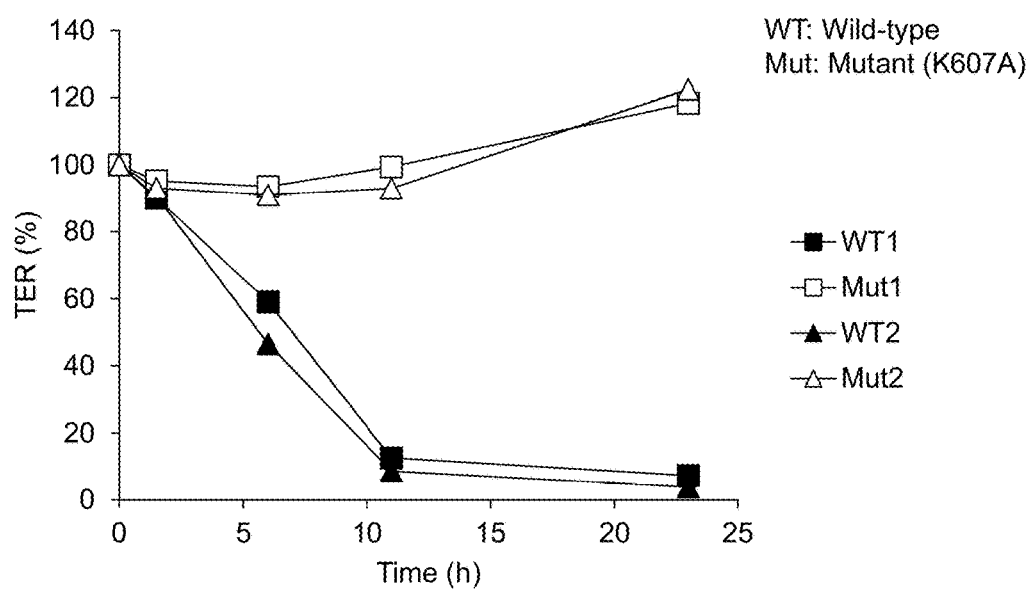
FIG. 10 illustrates the result of evaluation of intercellular adhesion inhibition, using Caco-2 cells, of the wild-type BHA complex and the mutant (K607A) BHA complex (added to an apical side).

(Example 6) Study on Influence of Mutant (K607A) BHA Complex on Intercellular Adhesion The influence of the mutant (K607A) BHA complex on the intercellular adhesion was evaluated by performing a high dose treatment (1 µM) in a TER assay using Caco-2 cells. The results are illustrated in FIG. 10. As illustrated in FIG. 10, in a culture well in which Caco-2 cells were treated with a wild-type BHA complex (WT) from the apical side, the TER value was greatly decreased within 12 hours after the treatment. On the other hand, in treating a mutant BHA complex (Mut), the TER value was not changed even after 24 hours, and substantially the same results were obtained in two dependent examinations.

Figure 11:
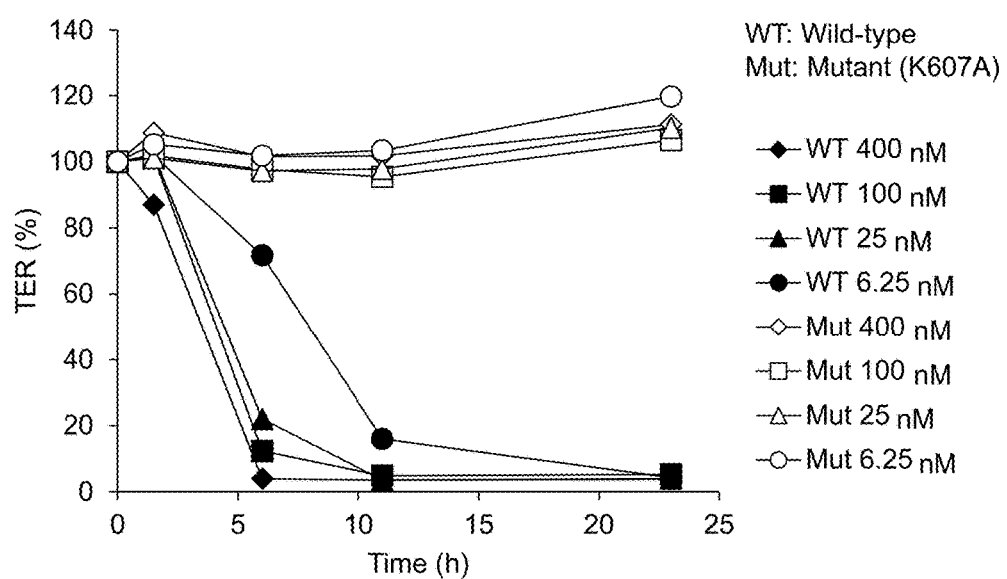
FIG. 11 illustrates the result of evaluation of the intercellular adhesion inhibition, using Caco-2 cells, of the wild-type BHA complex and the mutant (K607A) BHA complex (added to a basolateral side).

Besides, as illustrated in FIG. 11, if Caco-2 cells were treated from the basolateral side, the TER value was greatly decreased within 12 hours after a treatment with a wild-type BHA complex (WT) in a low concentration of 6.25 nM, but the TER value was not changed at all in a treatment with a mutant BHA complex (Mut) even in a high concentration of 400 nM. These results reveal that the wild-type BHA complex strongly inhibits the intercellular adhesion of Caco-2 cells but the mutant (K607A) BHA complex had a property that it does not affect the intercellular adhesion at all.

Figure 12:
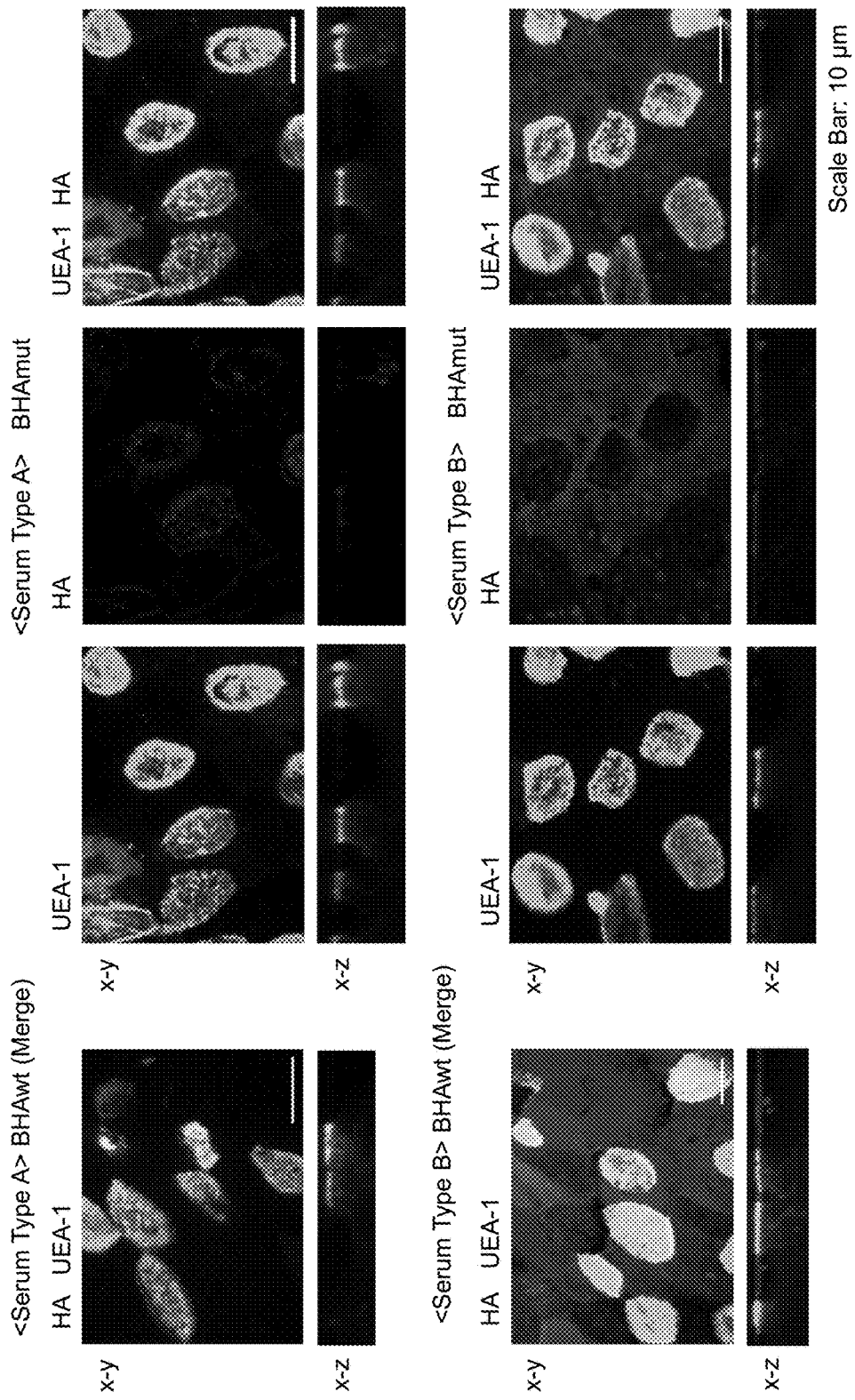
FIG. 12 illustrates M cell orientation of a wild-type HA complex and a mutant (K607A) HA complex (microphotographs obtained by observing localization of the HA complex in follicle-associated epithelium (FAE)) (UEA-1: image of M cells stained with FITC-labeled UEA-1; HA: stained image of the HA complex).

(Example 7) M Cell Orientation of Wild-Type HA Complex or Mutant (K607A) HA Complex Wild-type HA complexes (of type A and type B) were produced by conjugating, with the HA1 and the HA3, botulinum type A and type B HA2 having been labeled with Alexa 568. Similarly, Mutant HA complexes (of type A and type B) were produced by conjugating, with the HA1 and the HA3 (having K607A mutation), botulinum type A and type B HA2 having been labeled with Alexa 568. Each of these wild-type HA complexes and mutant HA complexes in an amount of 600 nM was injected into a ligated mouse intestinal tract, so as to observe localization of the HA complex after 2 hours with a confocal microscope. M cells were stained with FITC-labeled UEA-1. The results are illustrated in FIG. 12. As illustrated in FIG. 12, binding to and transcytosis through the M cells were observed in the wild-type HA complex. Besides, it was revealed that the mutant (K607A) HA complex has high M cell orientation similarly to the wild-type HA complex.

Figure 13:
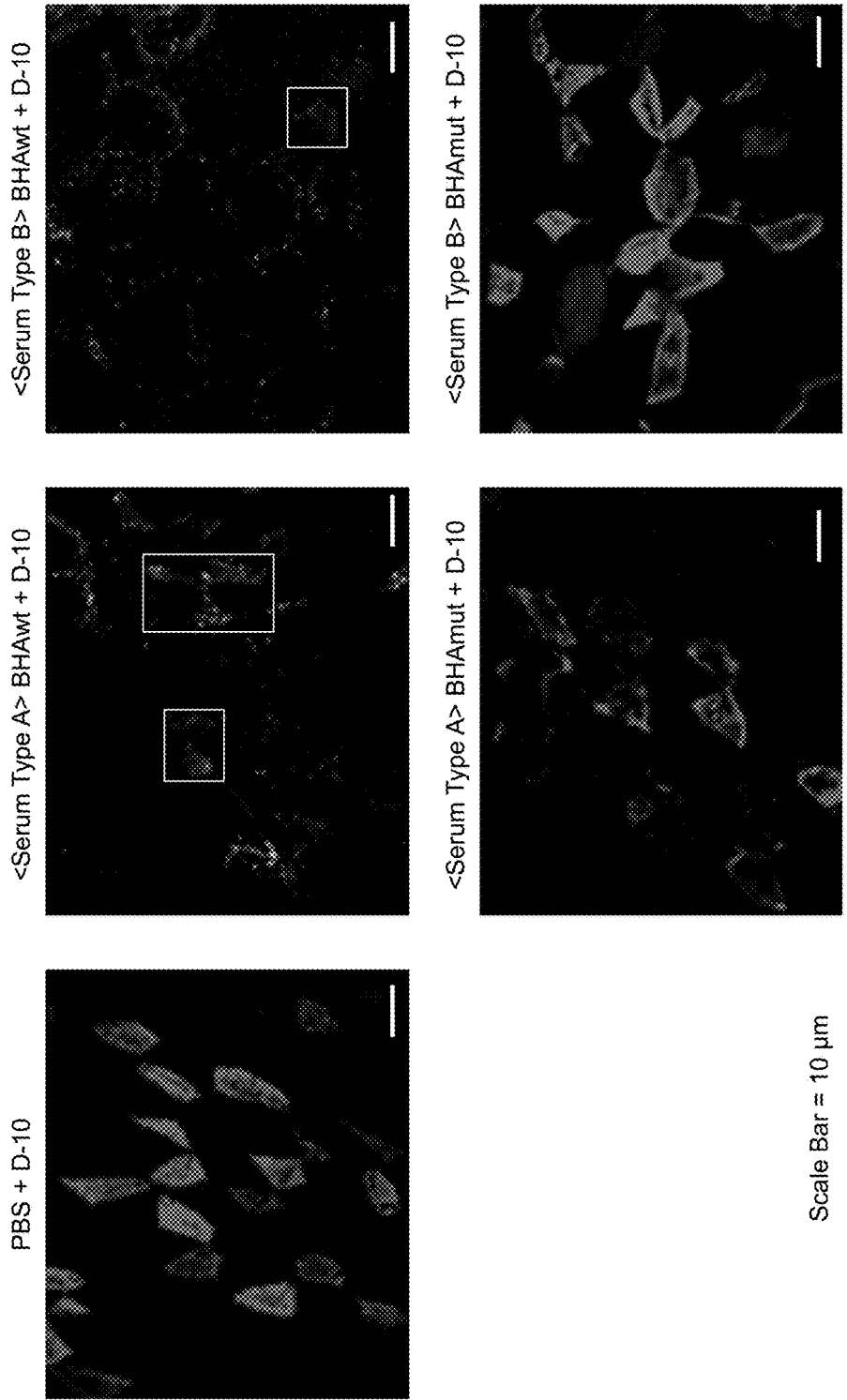
FIG. 13 illustrates the result of evaluation, depending on the form of M cells and dextran remaining between cells, of intercellular adhesion disrupting ability of a wild-type HA complex and a mutant (K607A) HA complex on an epithelial layer of a mucosal tissue (D-10: FITC-labeled dextran (10K)).

(Example 8) Study of Intercellular Adhesion Disrupting Ability on Epithelial Layer of Mucosal Tissue of Wild-Type HA Complex or Mutant (K607A) HA Complex In order to study the influence on the intercellular adhesion of a mouse mucosal epithelial tissue of a wild-type HA complex (of type A or type B) or a mutant (K607A) HA complex (of type A or type B), a mixture of 5 µM of each HA complex and 2 mg/mL FITC-labeled dextran (10 K) was injected into a ligated mouse intestinal tract, so as to observe dextran having entered intercellular spaces after 2 hours with a confocal microscope. M cells were stained with Rhodamine-labeled UEA-1. The results are illustrated in FIG. 13. As illustrated in FIG. 13, dextran was found to remain (as green dots; portions illustrated as white dots in the drawing) in the epithelial layer of the intestinal tract treated with the wild-type HA complex (HAwt) of both the serum type A and type B. Besides, morphological abnormalities of UEA-1 positive cells were found in the HAwt (which correspond to portions each surrounded with a white frame in the drawing). On the other hand, no dextran was found to remain in using the mutant (K607A) HA complex (HAmut), and the morphology of UEA-1 positive cells was normal. These results suggest that the HAwt disrupts the intercellular adhesion in the vicinity of the UEA-1 positive cells present on the epithelial layer of the ligated intestinal tract, but that the HAmut is a candidate of a safe mucosal adjuvant not affecting the intercellular adhesion of the mucosal epithelium.

(Example 9) Evaluation of Ability of Wild-Type BHA Complex and Mutant (K607A) BHA Complex Adjuvants to Activate Innate Immunity The amounts of IL-6 cytokine production resulting from treatments respectively with the wild-type BHA complex and mutant (K607A) BHA complex adjuvants were measured using untreated mouse splenocytes, so as to evaluate the abilities of the BHA complex adjuvants to activate innate immunity.

Figure 14:
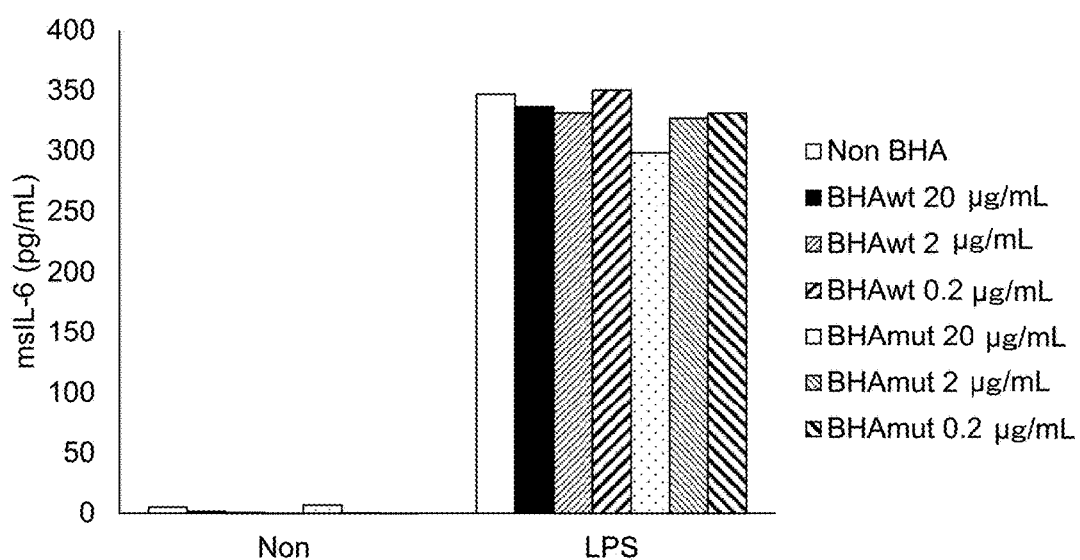
FIG. 14 illustrates activation of innate immunity (IL-6 production) caused by the wild-type BHA complex and the mutant (K607A) BHA complex.
Figure 16:
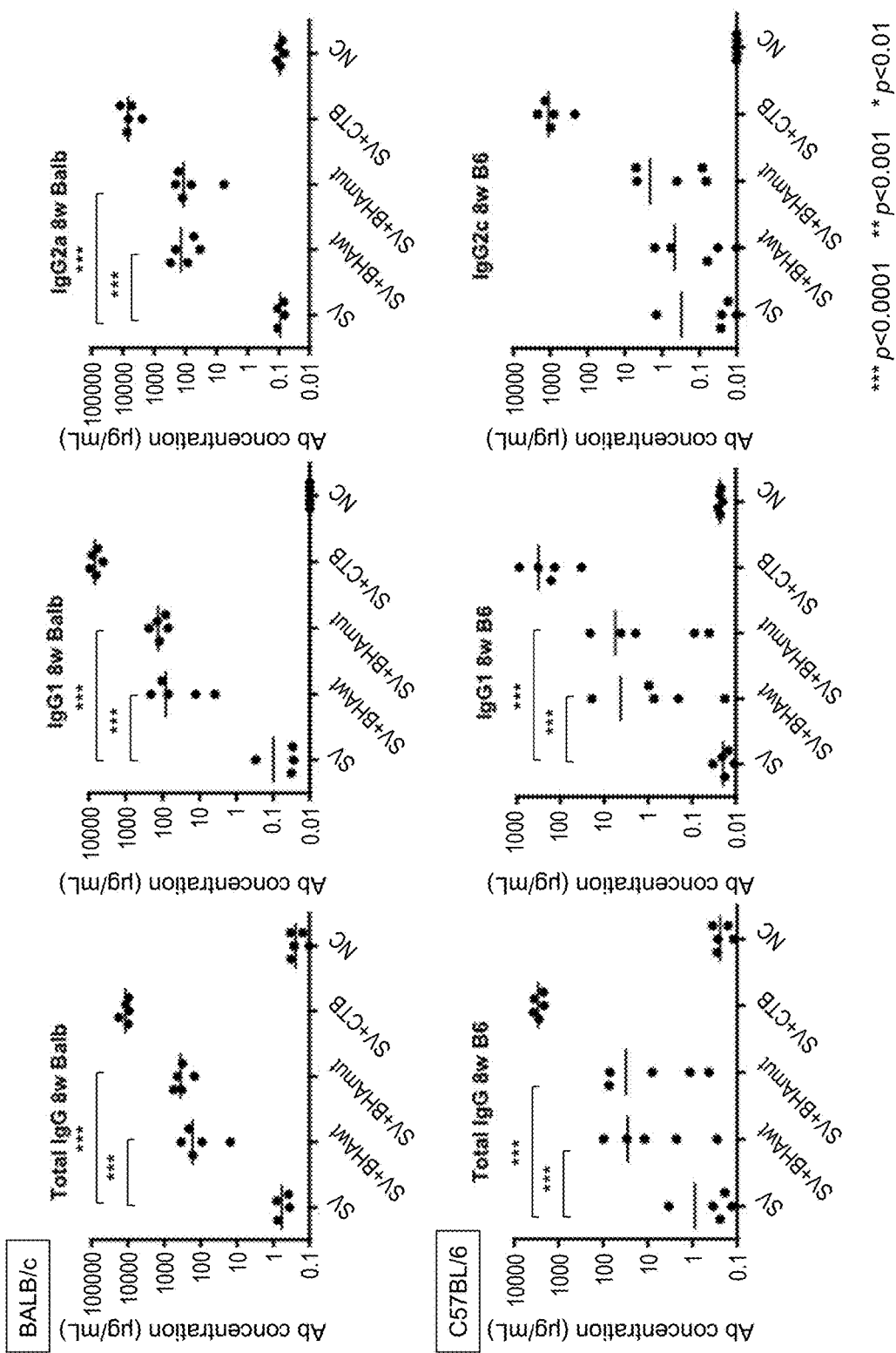
FIG. 16 illustrates measurement results, obtained by ELISA, for a production amount of influenza-antigen-specific IgG in blood (SV: a group administered with influenza split vaccine alone; SV+BHAwt: a group administered with influenza split vaccine and the wild-type BHA complex; SV+BHAmut: a group administered with influenza split vaccine and the mutant (K607A) BHA complex; SV+CTB: a group administered with influenza split vaccine and cholera toxin B subunit; NC: a non-administered group, * p<0.0001,  p<0.001, * p<0.01).
Figure 17:
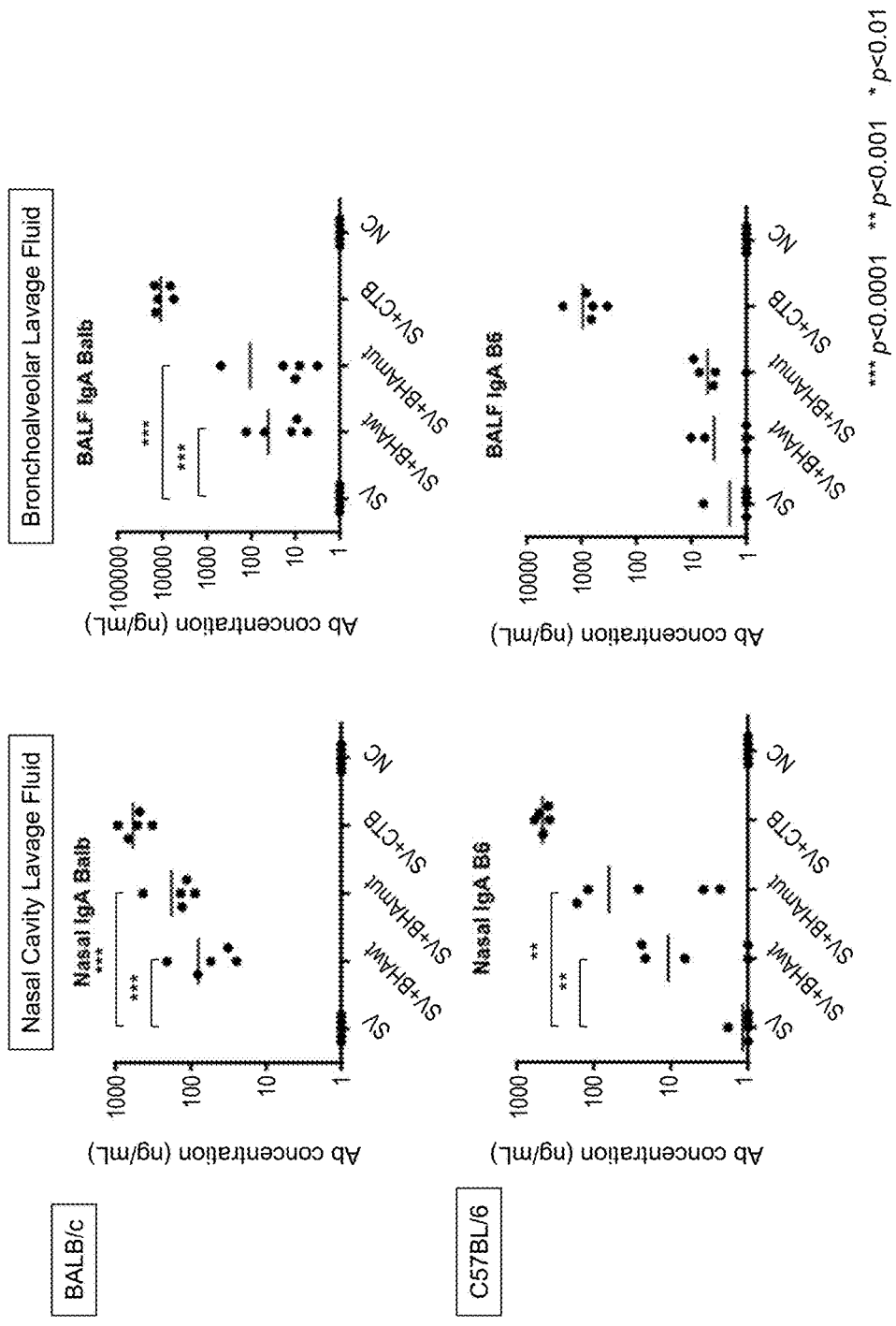
FIG. 17 illustrates measurement results, obtained by ELISA, for production amounts of influenza-antigen-specific IgA in a nasal cavity lavage fluid and in a bronchoalveolar lavage fluid (SV: a group administered with influenza split vaccine alone; SV+BHAwt: a group administered with influenza split vaccine and the wild-type BHA complex; SV+BHAmut: a group administered with influenza split vaccine and the mutant (K607A) BHA complex; SV+CTB: a group administered with influenza split vaccine and cholera toxin B subunit; NC: a non-administered group, * p<0.0001,  p<0.001, * p<0.01).

Splenocytes were sampled from untreated mice raised under SPF conditions (C57BL/6, 6-week-old, female, purchased from CLEA Japan, Inc.) and seeded onto a 96-well plate at a cell density of $1 \times 10^6$ cells/well. Thereafter, the BHA complex (BHA) was serially diluted from 20 µg/ml (20 µg/ml, 2 µg/ml, 0.2 µg/ml), and the splenocytes were stimulated. The splenocytes were co-stimulated with the BHA complex adjuvant in combination with a TLR ligand of LPS (1 µg/ml). A culture supernatant was recovered 24 hours after the start of the stimulation and the amount of cytokine (IL-6) in the culture supernatant was measured (R&D systems). The results are illustrated in FIG. 14. As illustrated in FIG. 14, the production of IL-6 caused by the BHA complex adjuvant alone was below the detection limit in both cases using the wild-type BHA complex (BHAwt) and the mutant (K607A) BHA complex (BHAmut). Since the BHA complex adjuvant does not affect the IL-6 production through the LPS stimulation in both cases using the wild-type BHA complex (BHAwt) and the mutant (K607A) BHA complex (BHAmut), it was regarded that the BHA complex adjuvant would not enhance or suppress signals to activate any other innate immunity.

Besides, the amounts of TNF-alpha and IL-6 production were measured in using the mutant (K607A) BHA complex adjuvant (BHAmut) and its subcomponents (BHA1, BHA2 and BHA3mut). The results are illustrated in FIG. 15. As illustrated in FIG. 15, the production of TNF-alpha and IL-6 was below the detection limit even if splenocytes were treated with any of the BHA complex or the BHA subcomponents in a 100-fold concentration (100 µg/mL, 33 µg/mL, 11 µg/mL and 3.7 µg/mL) of LPS (1 µg/mL, 0.33 µg/mL, 0.11 µg/mL and 0.037 µg/mL). These results suggest that both the wild-type and the mutant BHA complex adjuvants are non-inflammatory adjuvants that do not affect signals to activate innate immunity.

(Example 10) Effects as Transnasal Adjuvant of Wild-Type and Mutant BHA Complexes Using Influenza HA Antigen An influenza split vaccine was used as an antigen to evaluate adjuvant effects of the BHA complexes.

(1) Experimental Animals and Materials

BALB/c mice and C57BL/6 mice (6-week-old, female) were purchased from CLEA Japan, Inc. Mice were raised under SPF conditions.

A mouse-adapted A/Puerto Rico/8/34 (H1N1) split vaccine (hereafter referred to as the "split vaccine") received from Kitasato Daiichi Sankyo Vaccine Co., Ltd. was used as a vaccine antigen. During the experiment, the antigen was refrigerated at 4° C. in the dark.

The wild-type BHA complex (BHAwt) adjuvant and the mutant BHA complex (BHAmut: K607A) adjuvant prepared in Example 1 were used as the adjuvants. An endotoxin content was set with a content of 0.5 EU/mL or lower regarded as the standard for purification. The BHA adjuvant was cryopreserved at −80° C., and thawed immediately before use to be used for immunization. A cholera toxin adjuvant (CTB) was prepared by mixing 1 μg of cholera toxin B subunit (Catalog No. 033-20611, Wako Pure Chemical Industries, Ltd.) and 1 ng of cholera toxin (Catalog No. 033-20621, Wako Pure Chemical Industries, Ltd.) for each mouse. The cholera toxin adjuvant was cryopreserved at −80° C., and thawed immediately before use to be used for immunization.

(2) Test Method

A vaccine preparation for each mouse was prepared by adding PBS(−) to a mixture of 1 μg of the split vaccine antigen with 20 μg of the BHA complex (BHA) adjuvant or with 1.001 μg of the cholera toxin mixed (CTB) adjuvant to attain an amount of 12 μL. Each vaccine preparation was administered to a 6-week-old mouse through both nasal cavities in amount of 6 μL each. The administration was carried out four times in total at intervals of 2 weeks (day 0, day 14, day 28, and day 42). Immediately before booster immunizations were provided on day 14, day 28, and day 42, the mouse was anesthetized using Ketalar (Daiichi Sankyo Company, Limited)/Selactar (Bayer), and a blood sample was obtained from the orbital venous plexus. The sampled blood was allowed to stand still at 4° C. overnight, and serum separation was carried out using a tabletop refrigerated centrifuge (9,100 g, 10 minutes, 4° C.). The thus obtained serum specimen was cryopreserved at −20° C. In order to evaluate the adjuvant effect of the BHA complex, IgG (total IgG, IgG1, IG2a, and IG2c) in the serum specimen was measured.

The mouse was anesthetized using Ketalar/Selactar 56 days after the start of the immunization, exsanguinated via cardiopuncture, and euthanized. Immediately after the euthanasia, a nasal cavity lavage fluid and a bronchoalveolar lavage fluid were respectively sampled. Thereafter, the nasal cavity lavage fluid and the bronchoalveolar lavage fluid were stored on ice or refrigerated until an ELISA assay.

The ELISA assay was carried out in the following manner. The split vaccine antigen was coated on a plate at a concentration of 1 μg/mL (4° C., overnight), and blocking was carried out with 1% BSA/PBST (Tween 20: 0.05%) by allowing the plate to stand still at room temperature for 2 hours. The serum sample was serially diluted using 1% BSA/PBST (Tween 20: 0.05%). As a secondary antibody, an HRP-labeled antibody in accordance with the subclass was used. OD was measured using a plate reader after coloring, and the amount of influenza-antigen-specific antibody production was measured. Each of the nasal cavity lavage fluid and the bronchoalveolar lavage fluid was serially diluted using 1% BSA/PBST (Tween 20: 0.05%), and in order to evaluate the effect of the BHA complex adjuvant to potentiate the antigen-specific mucosal immunity, the amount of influenza-antigen-specific mucosal IgA production was measured.

(3) Test Results

FIG. 16 illustrates the results of measurement of influenza-antigen-specific IgG in blood (56 days after the start of the immunization). As illustrated in FIG. 16, the reaction of the antigen-specific antibody in blood was induced at a significantly higher level in groups subjected to the immunization with the wild-type BHA complex (BHAwt) adjuvant or the mutant BHA complex (BHAmut: K607A) adjuvant in combination with the influenza antigens than in a group subjected to the immunization with the influenza antigen alone. Such a phenomenon was observed in all the evaluated IgG subclasses.

FIG. 17 illustrates the results of measurement of the amounts of secretory IgA production in the nasal cavity lavage fluid and in the bronchoalveolar lavage fluid. As illustrated in FIG. 17, the amount of antigen-specific IgA production was high in the groups subjected to the immunization with the wild-type BHA complex (BHAwt) adjuvant or the mutant BHA complex (BAHmut: K607A) adjuvant in combination with the influenza antigen. In contrast, secretory IgA production was not substantially observed in the group of mice subjected to the immunization with the influenza antigen alone. These results proved that the BHA complex is effective as a novel non-inflammatory mucosal adjuvant.

(Example 11) Effects as Transnasal Adjuvant of Wild-Type and Mutant AHA Complexes or Wild-Type and Mutant BHA Complexes Using Influenza HA Antigen An influenza split vaccine was used as an antigen to evaluate the adjuvant effects of the BHA complexes.

(1) Experimental Animals and Materials

BALB/c mice (6-week-old, female) were purchased from CLEA Japan, Inc. Mice were raised under SPF conditions.

A mouse-adapted A/Puerto Rico/8/34 (H1N1) split vaccine (hereafter referred to as the "split vaccine") received from Kitasato Daiichi Sankyo Vaccine Co., Ltd. was used as a vaccine antigen. During the experiment, the antigen was refrigerated at 4° C. in the dark.

The wild-type AHA complex (AHAwt) adjuvant, the wild-type BHA complex (BHAwt) adjuvant, the mutant AHA complex (AHA L473A, AHA M508A, AHA F569A and AHA K607A) adjuvants, the mutant BHA complex (BHA K607A) adjuvant prepared in Example 1 were used as the adjuvants. An endotoxin content was set with a content of 0.5 EU/mL or lower regarded as the standard for purification. The adjuvants were cryopreserved at −80° C., and thawed immediately before use to be used for immunization. A cholera toxin adjuvant (CTB) was prepared by mixing 1 µg of cholera toxin B subunit (Catalog No. 033-20611, Wako Pure Chemical Industries, Ltd.) and 1 ng of cholera toxin (Catalog No. 033-20621, Wako Pure Chemical Industries, Ltd.) for each mouse. The cholera toxin adjuvant was cryopreserved at −80° C., and thawed immediately before use to be used for immunization.

(2) Test Method

A vaccine preparation for each mouse was prepared by adding PBS(−) to a mixture of 1 µg of the split vaccine antigen with 20 µg of the AHA complex (AHA) adjuvant, 20 µg of the BHA complex (BHA) adjuvant or with 1.001 µg of the cholera toxin mixed (CTB) adjuvant to attain an amount of 12 µL. Each vaccine preparation was administered to a 6-week-old mouse through both nasal cavities in amount of 6 µL each. The administration was carried out three times in total at intervals of 2 weeks (day 0, day 14 and day 28). The mouse was anesthetized using Ketalar/Selactar 42 days after the start of the immunization, exsanguinated via cardiopuncture, and euthanized. The thus obtained blood was allowed to stand still at 4° C. overnight, and serum separation was carried out using a tabletop refrigerated centrifuge (9,100 g, 10 minutes, 4° C.). The thus obtained serum specimen was cryopreserved at −20° C. In order to evaluate the adjuvant effect of the AHA complex or the BHA complex, IgG (total IgG) in the serum specimen was measured. After the euthanasia, a nasal cavity lavage fluid was sampled. The sampled nasal cavity lavage fluid was stored on ice or refrigerated until an ELISA assay.

The ELISA assay was carried out in the following manner. The split vaccine antigen was coated on a plate at a concentration of 1 µg/mL (4° C., overnight), and blocking was carried out with 1% BSA/PBST (Tween 20: 0.05%) by allowing the plate to stand still at room temperature for 2 hours. The serum sample was serially diluted using 1% BSA/PBST (Tween 20: 0.05%). As a secondary antibody, an HRP-labeled antibody in accordance with the subclass was used. OD was measured using a plate reader after coloring, and the amount of influenza-antigen-specific antibody production was measured. The nasal cavity lavage fluid was serially diluted using 1% BSA/PBST (Tween 20: 0.05%), and in order to evaluate the effect of the AHA complex or the BHA complex adjuvant to potentiate the antigen-specific mucosal immunity, the amount of influenza-antigen-specific mucosal IgA production was measured.

(3) Test Results

FIG. 18A illustrates the results of measurement of influenza-antigen-specific IgG in blood. As illustrated in FIG. 18A, the reaction of the antigen-specific antibody in blood was induced at a higher level in groups subjected to the immunization with the wild-type AHA complex (AHAwt) adjuvant, the wild-type BHA complex (BHAwt) adjuvant, the mutant AHA complex (AHA L473A, AHA M508A, AHA F569A or AHA K607A) adjuvant or the mutant BHA complex (BHA K607A) adjuvant in combination with the influenza antigen than in a group subjected to the immunization with the influenza antigen alone. Besides, the potentiating activity for the antigen-specific antibody in blood was equivalent among the wild-type AHA complex adjuvant, the wild-type BHA complex adjuvant, the mutant AHA complex adjuvant and the mutant BHA complex adjuvant.

FIG. 18B illustrates the results of measurement of the amounts of secretory IgA production in the nasal cavity lavage fluid. As illustrated in FIG. 18B, the amount of the antigen-specific mucosal IgA production was high in the groups subjected to the immunization with the wild-type AHA complex (AHAwt) adjuvant, the wild-type BHA complex (BHAwt) adjuvant, the mutant AHA complex (AHA L473A, AHA M508A, AHA F569A or AHA K607A) adjuvant, or the mutant BHA complex (BAH K607A) adjuvant in combination with the influenza antigen than in a group subjected to the immunization with the influenza antigen alone. Besides, the potentiating activity for the antigen-specific mucosal IgA antibody was equivalent among the wild-type AHA complex adjuvant, the wild-type BHA complex adjuvant, the mutant AHA complex adjuvant and the mutant BHA complex adjuvant. These results suggest that the mucosal adjuvant activity is equivalent among the wild-type AHA complex adjuvant, the wild-type BHA complex adjuvant, the mutant AHA complex adjuvant and the mutant BHA complex adjuvant, and is not affected by a difference in the mutation introduction site.

INDUSTRIAL APPLICABILITY

The present invention is applicable in the field of production of a mucosal adjuvant and a mucosal vaccine preparation containing the same.

All publications, patents, and patent applications cited herein are incorporated herein by reference in their entirety.

The invention claimed is:

1. A mucosal vaccine preparation comprising (i) a vaccine antigen and (ii) an adjuvant for simultaneous or sequential administration with the vaccine antigen, wherein the adjuvant comprises a protein complex composed of hemagglutinin (HA) subcomponents HA1, HA2 and HA3 of botulinum toxin, wherein the subcomponent HA1 is:

a protein which comprises an amino acid sequence of positions 7 to 294 of SEQ ID NO: 1;

wherein the subcomponent HA2 is:

a protein which comprises an amino acid sequence of positions 2 to 146 of SEQ ID NO: 2; and wherein the subcomponent HA3 is:

a protein which comprises an amino acid sequence of positions 19 to 626 of SEQ ID NO: 3 and includes a substitution of at least one or more amino acids among leucine at position 473, methionine at position 508, phenylalanine at position 569, and lysine at position 607 with another amino acid, with respect to the amino acid sequence shown in SEQ ID NO: 3.

2. A mucosal vaccine preparation comprising (i) a vaccine antigen and (ii) an adjuvant for simultaneous or sequential administration with the vaccine antigen, wherein the adjuvant comprises a protein complex composed of hemagglutinin (HA) subcomponents HA1, HA2 and HA3 of botulinum toxin, wherein the subcomponent HA1 is:

a protein which comprises an amino acid sequence of positions 6 to 293 of in SEQ ID NO: 15;

wherein the subcomponent HA2 is:

a protein which comprises an amino acid sequence of positions 2 to 146 of SEQ ID NO: 16; and wherein the subcomponent HA3 is:

a protein which comprises an amino acid sequence of positions 20 to 626 of SEQ ID NO: 17 and includes a substitution of at least one or more amino acids among leucine at position 473, methionine at position 508, phenylalanine at position 569, and lysine at position 607 with another amino acid, with respect to the amino acid sequence shown in SEQ ID NO: 17.

3. The mucosal vaccine preparation according to claim 1, wherein the another amino acid is alanine.

4. The mucosal vaccine preparation according to claim 1, wherein the vaccine antigen is a subunit antigen or an inactivated antigen.

5. The mucosal vaccine preparation according to claim 1, wherein the vaccine antigen is derived from a pathogen causing a mucosal infection.

6. The mucosal vaccine preparation according to claim 5, wherein the pathogen causing the mucosal infection is a virus.

7. The mucosal vaccine preparation according to claim 6, wherein the virus is influenza virus, human immunodeficiency virus (HIV), chickenpox virus, measles virus, rubella virus, mumps virus, poliovirus, rotavirus, norovirus, adenovirus, herpes virus, RS virus, dengue virus, Japanese encephalitis virus, severe acute respiratory syndrome (SARS) virus, cytomegalovirus, Epstein-Barr (EB) virus, or hepatitis virus (type A, type B or type C).

8. The mucosal vaccine preparation according to claim 1, formulated for transmucosal administration.

9. The mucosal vaccine preparation according to claim 8, wherein the transmucosal administration is intranasal administration.

10. The mucosal vaccine preparation according to claim 2, wherein the another amino acid is alanine.

11. The mucosal vaccine preparation according to claim 2, wherein the vaccine antigen is a subunit antigen or an inactivated antigen.

12. The mucosal vaccine preparation according to claim 2, wherein the vaccine antigen is derived from a pathogen causing a mucosal infection.

13. The mucosal vaccine preparation-according to claim 12, wherein the pathogen causing the mucosal infection is a virus.

14. The mucosal vaccine preparation-according to claim 13, wherein the virus is influenza virus, human immunodeficiency virus (HIV), chickenpox virus, measles virus, rubella virus, mumps virus, poliovirus, rotavirus, norovirus, adenovirus, herpes virus, RS virus, dengue virus, Japanese encephalitis virus, severe acute respiratory syndrome (SARS) virus, cytomegalovirus, Epstein-Barr (EB) virus, or hepatitis virus (type A, type B or type C).

15. The mucosal vaccine preparation according to claim 2, formulated for transmucosal administration.

16. The mucosal vaccine preparation according to claim 15, wherein the transmucosal administration is intranasal administration.

* * * * *

SEQUENCE LISTING

```
<160> NUMBER OF SEQ ID NOS: 28

<210> SEQ ID NO 1
<211> LENGTH: 294
<212> TYPE: PRT
<213> ORGANISM: Clostridium botulinum

<400> SEQUENCE: 1

Met Glu His Tyr Ser Thr Ile Gln Asn Ser Leu Asn Asp Lys Ile Val
1               5                   10                  15

Thr Ile Ser Cys Lys Ala Asn Thr Asp Leu Phe Phe Tyr Gln Val Pro
            20                  25                  30

Gly Asn Gly Asn Val Ser Leu Phe Gln Gln Thr Arg Asn Tyr Leu Glu
        35                  40                  45
```

```
Arg Trp Arg Ile Ile Tyr Asp Ser Asn Lys Ala Ala Tyr Lys Ile Lys
            50                  55                  60

Ser Met Asn Ile Tyr Asn Thr Asn Leu Val Leu Thr Trp Asn Ala Pro
 65                  70                  75                  80

Thr His Asn Ile Ser Ala Gln Gln Asp Ser Asn Ala Asp Asn Gln Tyr
                    85                  90                  95

Trp Leu Leu Leu Lys Asp Ile Gly Asn Asn Ser Phe Ile Ile Ala Ser
                100                 105                 110

Tyr Lys Asn Pro Asn Leu Val Leu Tyr Ala Asp Thr Val Ala Arg Asn
                115                 120                 125

Leu Lys Leu Ser Thr Leu Asn Asn Ser Ser Tyr Ile Lys Phe Ile Ile
130                 135                 140

Glu Asp Tyr Val Ile Ser Asp Phe Lys Asn Phe Thr Cys Arg Ile Ser
145                 150                 155                 160

Pro Ile Leu Ala Gly Gly Lys Val Val Gln Gln Val Ser Met Thr Asn
                165                 170                 175

Leu Ala Val Asn Leu Tyr Ile Trp Asn Asn Asp Leu Asn Gln Lys Trp
                180                 185                 190

Thr Ile Ile Tyr Asn Glu Glu Lys Ala Ala Tyr Gln Phe Phe Asn Lys
                195                 200                 205

Ile Leu Ser Asn Gly Val Leu Thr Trp Ile Phe Ser Asp Gly Asn Thr
210                 215                 220

Val Arg Val Ser Ser Ser Ala Gln Asn Asn Asp Ala Gln Tyr Trp Leu
225                 230                 235                 240

Ile Asn Pro Val Ser Asp Asn Tyr Asp Arg Tyr Thr Ile Thr Asn Leu
                245                 250                 255

Arg Asp Lys Thr Lys Val Leu Asp Leu Tyr Gly Gly Gln Thr Ala Asp
                260                 265                 270

Gly Thr Thr Ile Gln Val Phe Asn Ser Asn Gly Gly Asp Asn Gln Ile
                275                 280                 285

Trp Thr Met Ser Asn Pro
                290

<210> SEQ ID NO 2
<211> LENGTH: 146
<212> TYPE: PRT
<213> ORGANISM: Clostridium botulinum

<400> SEQUENCE: 2

Met Ser Ala Glu Arg Thr Phe Leu Pro Asn Gly Asn Tyr Asn Ile Lys
 1               5                  10                  15

Ser Ile Phe Ser Gly Ser Leu Tyr Leu Ser Pro Val Ser Gly Ser Leu
                20                  25                  30

Thr Phe Ser Asn Glu Ser Ser Ala Asn Asn Gln Lys Trp Asn Val Glu
                35                  40                  45

Tyr Met Ala Glu Asn Arg Cys Phe Lys Ile Ser Asn Val Ala Glu Pro
            50                  55                  60

Asn Lys Tyr Leu Ser Tyr Asp Asn Phe Gly Phe Ile Ser Leu Asp Ser
 65                  70                  75                  80

Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Asp Tyr Ala Trp
                100                 105                 110

Asp Ile Tyr Asp Thr Asn Glu Asn Ile Leu Ser Gln Pro Leu Leu Leu
                115                 120                 125
```

Leu Pro Asn Phe Asp Ile Tyr Asn Ser Asn Gln Met Phe Lys Leu Glu
130                 135                 140

Lys Ile
145

<210> SEQ ID NO 3
<211> LENGTH: 626
<212> TYPE: PRT
<213> ORGANISM: Clostridium botulinum

<400> SEQUENCE: 3

Met Asn Ser Ser Ile Lys Lys Ile Tyr Asn His Ile Gln Glu Lys Val
1               5                   10                  15

Ile Asn Tyr Ser Asp Thr Ile Asp Leu Ala Asp Gly Asn Tyr Val Val
            20                  25                  30

Ser Arg Gly Asp Gly Trp Ile Leu Ser Arg Gln Asn Gln Ile Leu Gly
        35                  40                  45

Gly Ser Val Ile Ser Asn Gly Ser Thr Gly Ile Val Gly Asp Leu Arg
50                  55                  60

Val Asn Asp Asn Ala Ile Pro Tyr Tyr Pro Thr Pro Ser Phe Asn
65                  70                  75                  80

Glu Glu Tyr Ile Lys Asn Asn Ile Gln Thr Val Phe Ala Asn Phe Thr
                85                  90                  95

Glu Ala Asn Gln Ile Pro Ile Gly Phe Glu Phe Ser Lys Thr Ala Pro
            100                 105                 110

Ser Asn Lys Asn Leu Tyr Met Tyr Leu Gln Tyr Thr Tyr Ile Arg Tyr
        115                 120                 125

Glu Ile Ile Lys Val Leu Gln His Glu Ile Ile Glu Arg Ala Val Leu
130                 135                 140

Tyr Val Pro Ser Leu Gly Tyr Val Lys Ser Ile Glu Phe Asn Pro Gly
145                 150                 155                 160

Glu Lys Ile Asn Lys Asp Phe Tyr Phe Leu Thr Asn Asp Lys Cys Ile
                165                 170                 175

Leu Asn Glu Gln Phe Leu Tyr Lys Lys Ile Leu Glu Thr Thr Lys Asn
            180                 185                 190

Ile Pro Thr Asn Asn Ile Phe Asn Ser Lys Val Ser Ser Thr Gln Arg
        195                 200                 205

Val Leu Pro Tyr Ser Asn Gly Leu Tyr Val Ile Asn Lys Gly Asp Gly
210                 215                 220

Tyr Ile Arg Thr Asn Asp Lys Asp Leu Ile Gly Thr Leu Leu Ile Glu
225                 230                 235                 240

Ala Gly Ser Ser Gly Ser Ile Ile Gln Pro Arg Leu Arg Asn Thr Thr
                245                 250                 255

Arg Pro Leu Phe Thr Thr Ser Asn Asp Ala Lys Phe Ser Gln Gln Tyr
            260                 265                 270

Thr Glu Glu Arg Leu Lys Asp Ala Phe Asn Val Gln Leu Phe Asn Thr
        275                 280                 285

Ser Thr Ser Leu Phe Lys Phe Val Glu Glu Ala Pro Ser Asn Lys Asn
290                 295                 300

Ile Cys Ile Lys Ala Tyr Asn Thr Tyr Glu Lys Tyr Glu Leu Ile Asp
305                 310                 315                 320

Tyr Gln Asn Gly Ser Ile Val Asn Lys Ala Glu Tyr Tyr Leu Pro Ser
                325                 330                 335

Leu Gly Tyr Cys Glu Val Thr Asn Ala Pro Ser Pro Glu Ser Glu Val

```
                340                 345                 350
Val Lys Thr Gln Val Ala Glu Asp Gly Phe Ile Gln Asn Gly Pro Glu
            355                 360                 365

Glu Glu Ile Val Val Gly Val Ile Asp Pro Ser Glu Asn Ile Gln Glu
        370                 375                 380

Ile Asn Thr Ala Ile Ser Asp Asn Tyr Thr Tyr Asn Ile Pro Gly Ile
385                 390                 395                 400

Val Asn Asn Asn Pro Phe Tyr Ile Leu Phe Thr Val Asn Thr Thr Gly
                405                 410                 415

Ile Tyr Lys Ile Asn Ala Gln Asn Asn Leu Pro Ser Leu Lys Ile Tyr
            420                 425                 430

Glu Ala Ile Gly Ser Gly Asn Arg Asn Phe Gln Ser Gly Asn Leu Cys
        435                 440                 445

Asp Asp Asp Ile Lys Ala Ile Asn Tyr Ile Thr Gly Phe Asp Ser Pro
            450                 455                 460

Asn Ala Lys Ser Tyr Leu Val Val Leu Leu Asn Lys Asp Lys Asn Tyr
465                 470                 475                 480

Tyr Ile Arg Val Pro Gln Thr Ser Ser Asn Ile Glu Asn Gln Ile Lys
                485                 490                 495

Phe Lys Arg Glu Gly Asp Leu Arg Asn Leu Met Asn Ser Ser Val
            500                 505                 510

Asn Ile Ile Asp Asn Leu Asn Ser Thr Gly Ala His Tyr Tyr Thr Arg
            515                 520                 525

Gln Ser Pro Asp Val His Asp Tyr Ile Ser Tyr Glu Phe Thr Ile Pro
        530                 535                 540

Gly Asn Phe Asn Asn Lys Asp Thr Ser Asn Ile Arg Leu Tyr Thr Ser
545                 550                 555                 560

Tyr Asn Gln Gly Ile Gly Thr Leu Phe Arg Val Thr Glu Thr Ile Asp
                565                 570                 575

Gly Tyr Asn Leu Ile Asn Ile Gln Gln Asn Leu Asn Leu Leu Asn Ser
            580                 585                 590

Thr Lys Ser Ile Arg Leu Leu Asn Gly Ala Ile Tyr Ile Leu Lys Val
        595                 600                 605

Glu Val Thr Glu Leu Asn Asn Tyr Asn Ile Lys Leu His Ile Asp Ile
    610                 615                 620

Thr Asn
625

<210> SEQ ID NO 4
<211> LENGTH: 885
<212> TYPE: DNA
<213> ORGANISM: Clostridium botulinum
<220> FEATURE:
<221> NAME/KEY: CDS
<222> LOCATION: (1)..(885)

<400> SEQUENCE: 4 atg gaa cac tat tca aca atc caa aat tca tta aat gac aaa atc gtt      48
Met Glu His Tyr Ser Thr Ile Gln Asn Ser Leu Asn Asp Lys Ile Val
1               5                  10                  15 acc atc tcc tgt aag gct aat aca gat tta ttt ttt tat caa gtt ccc      96
Thr Ile Ser Cys Lys Ala Asn Thr Asp Leu Phe Phe Tyr Gln Val Pro
                20                  25                  30 ggt aac ggt aac gtt agc tta ttt caa caa act aga aat tac ctt gaa     144
Gly Asn Gly Asn Val Ser Leu Phe Gln Gln Thr Arg Asn Tyr Leu Glu
            35                  40                  45
```

-continued

| | | | | | | | | | | | | | | | | |
|---|---|---|---|---|---|---|---|---|---|---|---|---|---|---|---|---|
| aga | tgg | aga | att | ata | tat | gat | tct | aat | aaa | gct | gct | tat | aaa | ata | aaa | 192 |
| Arg | Trp | Arg | Ile | Ile | Tyr | Asp | Ser | Asn | Lys | Ala | Ala | Tyr | Lys | Ile | Lys | |
| | 50 | | | | 55 | | | | 60 | | | | | | | |
| agt | atg | aat | atc | tat | aat | act | aat | tta | gtt | tta | aca | tgg | aat | gca | cca | 240 |
| Ser | Met | Asn | Ile | Tyr | Asn | Thr | Asn | Leu | Val | Leu | Thr | Trp | Asn | Ala | Pro | |
| 65 | | | | | 70 | | | | | 75 | | | | | 80 | |
| aca | cat | aat | ata | tca | gcg | caa | caa | gat | tca | aat | gca | gat | aat | caa | tat | 288 |
| Thr | His | Asn | Ile | Ser | Ala | Gln | Gln | Asp | Ser | Asn | Ala | Asp | Asn | Gln | Tyr | |
| | | | | 85 | | | | | 90 | | | | | 95 | | |
| tgg | tta | tta | tta | aaa | gac | att | ggt | aac | aat | tca | ttt | att | att | gca | agt | 336 |
| Trp | Leu | Leu | Leu | Lys | Asp | Ile | Gly | Asn | Asn | Ser | Phe | Ile | Ile | Ala | Ser | |
| | | | 100 | | | | | 105 | | | | | 110 | | | |
| tat | aaa | aac | cct | aac | tta | gta | tta | tat | gct | gat | acc | gta | gct | cgt | aat | 384 |
| Tyr | Lys | Asn | Pro | Asn | Leu | Val | Leu | Tyr | Ala | Asp | Thr | Val | Ala | Arg | Asn | |
| | | | 115 | | | | | 120 | | | | | 125 | | | |
| ttg | aag | ctt | agc | aca | ctt | aat | aat | tca | agt | tat | ata | aaa | ttt | atc | ata | 432 |
| Leu | Lys | Leu | Ser | Thr | Leu | Asn | Asn | Ser | Ser | Tyr | Ile | Lys | Phe | Ile | Ile | |
| | 130 | | | | | 135 | | | | | 140 | | | | | |
| gaa | gat | tat | gta | ata | tca | gat | ttt | aaa | aat | ttc | aca | tgt | aga | ata | agt | 480 |
| Glu | Asp | Tyr | Val | Ile | Ser | Asp | Phe | Lys | Asn | Phe | Thr | Cys | Arg | Ile | Ser | |
| 145 | | | | | 150 | | | | | 155 | | | | | 160 | |
| cca | ata | tta | gcc | ggt | ggt | aaa | gtt | gta | caa | caa | gtg | tct | atg | aca | aat | 528 |
| Pro | Ile | Leu | Ala | Gly | Gly | Lys | Val | Val | Gln | Gln | Val | Ser | Met | Thr | Asn | |
| | | | | 165 | | | | | 170 | | | | | 175 | | |
| cta | gct | gtt | aat | tta | tat | att | tgg | aac | aat | gat | ctc | aat | caa | aaa | tgg | 576 |
| Leu | Ala | Val | Asn | Leu | Tyr | Ile | Trp | Asn | Asn | Asp | Leu | Asn | Gln | Lys | Trp | |
| | | | 180 | | | | | 185 | | | | | 190 | | | |
| aca | att | ata | tat | aat | gaa | gaa | aaa | gca | gca | tac | cag | ttt | ttt | aat | aaa | 624 |
| Thr | Ile | Ile | Tyr | Asn | Glu | Glu | Lys | Ala | Ala | Tyr | Gln | Phe | Phe | Asn | Lys | |
| | | | 195 | | | | | 200 | | | | | 205 | | | |
| ata | ctt | tca | aac | gga | gtt | cta | aca | tgg | att | ttt | tca | gat | ggt | aat | act | 672 |
| Ile | Leu | Ser | Asn | Gly | Val | Leu | Thr | Trp | Ile | Phe | Ser | Asp | Gly | Asn | Thr | |
| | 210 | | | | | 215 | | | | | 220 | | | | | |
| gta | aga | gtt | tct | tct | agt | gcg | caa | aac | aat | gat | gcc | caa | tat | tgg | ctt | 720 |
| Val | Arg | Val | Ser | Ser | Ser | Ala | Gln | Asn | Asn | Asp | Ala | Gln | Tyr | Trp | Leu | |
| 225 | | | | | 230 | | | | | 235 | | | | | 240 | |
| ata | aat | cct | gtt | tca | gat | aat | tat | gac | aga | tat | aca | att | act | aat | cta | 768 |
| Ile | Asn | Pro | Val | Ser | Asp | Asn | Tyr | Asp | Arg | Tyr | Thr | Ile | Thr | Asn | Leu | |
| | | | | 245 | | | | | 250 | | | | | 255 | | |
| cgc | gat | aaa | act | aaa | gtt | cta | gat | tta | tat | ggc | ggc | caa | aca | gca | gac | 816 |
| Arg | Asp | Lys | Thr | Lys | Val | Leu | Asp | Leu | Tyr | Gly | Gly | Gln | Thr | Ala | Asp | |
| | | | 260 | | | | | 265 | | | | | 270 | | | |
| gga | act | act | att | caa | gta | ttt | aat | tct | aat | gga | ggt | gat | aat | cag | ata | 864 |
| Gly | Thr | Thr | Ile | Gln | Val | Phe | Asn | Ser | Asn | Gly | Gly | Asp | Asn | Gln | Ile | |
| | | 275 | | | | | 280 | | | | | 285 | | | | |
| tgg | act | atg | agt | aac | cca | taa | | | | | | | | | | 885 |
| Trp | Thr | Met | Ser | Asn | Pro | | | | | | | | | | | |
| | 290 | | | | | | | | | | | | | | | |

<210> SEQ ID NO 5
<211> LENGTH: 441
<212> TYPE: DNA
<213> ORGANISM: Clostridium botulinum
<220> FEATURE:
<221> NAME/KEY: CDS
<222> LOCATION: (1)..(441)

<400> SEQUENCE: 5

| | | | | | | | | | | | | | | | | |
|---|---|---|---|---|---|---|---|---|---|---|---|---|---|---|---|---|
| atg | tca | gct | gaa | aga | act | ttt | cta | cct | aat | ggt | aat | tac | aat | ata | aaa | 48 |
| Met | Ser | Ala | Glu | Arg | Thr | Phe | Leu | Pro | Asn | Gly | Asn | Tyr | Asn | Ile | Lys | |
| 1 | | | | 5 | | | | | 10 | | | | | 15 | | |

-continued

```
tct atc ttt tct ggt tct tta tat tta agt cct gta tca gga tca tta    96
Ser Ile Phe Ser Gly Ser Leu Tyr Leu Ser Pro Val Ser Gly Ser Leu
        20                  25                  30 aca ttt tca aat gaa tct tct gca aat aat caa aaa tgg aat gta gaa   144
Thr Phe Ser Asn Glu Ser Ser Ala Asn Asn Gln Lys Trp Asn Val Glu
            35                  40                  45 tat atg gct gaa aat aga tgc ttt aaa atc tct aat gta gca gaa cca   192
Tyr Met Ala Glu Asn Arg Cys Phe Lys Ile Ser Asn Val Ala Glu Pro
 50                  55                  60 aat aag tat tta agt tac gat aac ttt gga ttt att tct tta gat tca   240
Asn Lys Tyr Leu Ser Tyr Asp Asn Phe Gly Phe Ile Ser Leu Asp Ser
 65                  70                  75                  80 tta tct aat aga tgc tac tgg ttt cct att aaa atc gct gta aat act   288
Leu Ser Asn Arg Cys Tyr Trp Phe Pro Ile Lys Ile Ala Val Asn Thr
                 85                  90                  95 tat att atg tta agt tta aat aaa gtg aat gaa tta gat tat gcc tgg   336
Tyr Ile Met Leu Ser Leu Asn Lys Val Asn Glu Leu Asp Tyr Ala Trp
            100                 105                 110 gac att tat gat act aat gaa aat att tta agt cag cca cta ctc cta   384
Asp Ile Tyr Asp Thr Asn Glu Asn Ile Leu Ser Gln Pro Leu Leu Leu
        115                 120                 125 cta cct aat ttt gat ata tac aat tca aat caa atg ttc aaa ctt gaa   432
Leu Pro Asn Phe Asp Ile Tyr Asn Ser Asn Gln Met Phe Lys Leu Glu
130                 135                 140 aaa ata taa                                                        441
Lys Ile
145

<210> SEQ ID NO 6
<211> LENGTH: 1881
<212> TYPE: DNA
<213> ORGANISM: Clostridium botulinum
<220> FEATURE:
<221> NAME/KEY: CDS
<222> LOCATION: (1)..(1881)

<400> SEQUENCE: 6 atg aat tca tct ata aaa aaa att tat aat cat ata caa gaa aaa gtt    48
Met Asn Ser Ser Ile Lys Lys Ile Tyr Asn His Ile Gln Glu Lys Val
1               5                   10                  15 ata aac tat agt gat act att gat tta gct gat ggt aat tat gta gtt    96
Ile Asn Tyr Ser Asp Thr Ile Asp Leu Ala Asp Gly Asn Tyr Val Val
            20                  25                  30 agc aga ggg gat gga tgg ata tta tct aga caa aat caa ata cta ggt   144
Ser Arg Gly Asp Gly Trp Ile Leu Ser Arg Gln Asn Gln Ile Leu Gly
        35                  40                  45 gga agt gta att agt aat gga tca aca gga ata gtt ggg gac cta cgt   192
Gly Ser Val Ile Ser Asn Gly Ser Thr Gly Ile Val Gly Asp Leu Arg
 50                  55                  60 gta aat gat aat gcg ata cca tat tat tat cca aca cca tcc ttc aat   240
Val Asn Asp Asn Ala Ile Pro Tyr Tyr Tyr Pro Thr Pro Ser Phe Asn
 65                  70                  75                  80 gaa gaa tat ata aaa aat aat ata caa act gta ttt gct aac ttt act   288
Glu Glu Tyr Ile Lys Asn Asn Ile Gln Thr Val Phe Ala Asn Phe Thr
                 85                  90                  95 gaa gct aat caa att cca ata gga ttt gaa ttt agt aaa acc gct ccc   336
Glu Ala Asn Gln Ile Pro Ile Gly Phe Glu Phe Ser Lys Thr Ala Pro
            100                 105                 110 tca aat aaa aac tta tat atg tat tta caa tat acc tac att aga tat   384
Ser Asn Lys Asn Leu Tyr Met Tyr Leu Gln Tyr Thr Tyr Ile Arg Tyr
        115                 120                 125
```

-continued

| | | |
|---|---|---|
| gaa ata ata aaa gtc ttg caa cat gaa att ata gaa aga gca gtt tta<br>Glu Ile Ile Lys Val Leu Gln His Glu Ile Ile Glu Arg Ala Val Leu<br>130 135 140 | 432 | |
| tat gtt cca tct ctt gga tat gtt aag tct ata gaa ttt aat cca ggg<br>Tyr Val Pro Ser Leu Gly Tyr Val Lys Ser Ile Glu Phe Asn Pro Gly<br>145 150 155 160 | 480 | |
| gaa aaa ata aat aaa gat ttt tac ttt tta act aat gat aag tgc att<br>Glu Lys Ile Asn Lys Asp Phe Tyr Phe Leu Thr Asn Asp Lys Cys Ile<br>165 170 175 | 528 | |
| tta aat gaa caa ttc cta tat aaa aaa att tta gaa act act aaa aat<br>Leu Asn Glu Gln Phe Leu Tyr Lys Lys Ile Leu Glu Thr Thr Lys Asn<br>180 185 190 | 576 | |
| ata cca act aac aat att ttt aat tct aaa gtt agt agc aca caa cga<br>Ile Pro Thr Asn Asn Ile Phe Asn Ser Lys Val Ser Ser Thr Gln Arg<br>195 200 205 | 624 | |
| gta ttg cct tat agt aat gga cta tat gtt att aat aag ggt gat gga<br>Val Leu Pro Tyr Ser Asn Gly Leu Tyr Val Ile Asn Lys Gly Asp Gly<br>210 215 220 | 672 | |
| tat ata aga aca aat gat aaa gat ttg ata ggt aca tta tta atc gaa<br>Tyr Ile Arg Thr Asn Asp Lys Asp Leu Ile Gly Thr Leu Leu Ile Glu<br>225 230 235 240 | 720 | |
| gca ggt tca tca gga agt att ata caa cct cga tta aga aat aca act<br>Ala Gly Ser Ser Gly Ser Ile Ile Gln Pro Arg Leu Arg Asn Thr Thr<br>245 250 255 | 768 | |
| agg cca tta ttc acc aca agt aat gat gca aaa ttc tca caa caa tat<br>Arg Pro Leu Phe Thr Thr Ser Asn Asp Ala Lys Phe Ser Gln Gln Tyr<br>260 265 270 | 816 | |
| act gaa gaa aga ctt aaa gac gct ttc aat gta caa tta ttt aat aca<br>Thr Glu Glu Arg Leu Lys Asp Ala Phe Asn Val Gln Leu Phe Asn Thr<br>275 280 285 | 864 | |
| tca aca tcg tta ttt aaa ttt gta gaa gaa gct cct tca aat aaa aat<br>Ser Thr Ser Leu Phe Lys Phe Val Glu Glu Ala Pro Ser Asn Lys Asn<br>290 295 300 | 912 | |
| ata tgc ata aag gct tat aat acc tat gaa aag tat gaa tta ata gac<br>Ile Cys Ile Lys Ala Tyr Asn Thr Tyr Glu Lys Tyr Glu Leu Ile Asp<br>305 310 315 320 | 960 | |
| tat caa aat gga agt att gtt aat aaa gct gag tat tac ctt cct tcc<br>Tyr Gln Asn Gly Ser Ile Val Asn Lys Ala Glu Tyr Tyr Leu Pro Ser<br>325 330 335 | 1008 | |
| tta gga tat tgt gaa gta act aat gct cct tca cct gaa tct gaa gta<br>Leu Gly Tyr Cys Glu Val Thr Asn Ala Pro Ser Pro Glu Ser Glu Val<br>340 345 350 | 1056 | |
| gtt aaa acg caa gtg gct gaa gat gga ttt ata cag aat ggc ccc gag<br>Val Lys Thr Gln Val Ala Glu Asp Gly Phe Ile Gln Asn Gly Pro Glu<br>355 360 365 | 1104 | |
| gaa gaa atc gta gta ggt gtc ata gac cca tct gaa aat ata caa gaa<br>Glu Glu Ile Val Val Gly Val Ile Asp Pro Ser Glu Asn Ile Gln Glu<br>370 375 380 | 1152 | |
| ata aat act gct att tca gat aat tac aca tat aac att ccg ggt att<br>Ile Asn Thr Ala Ile Ser Asp Asn Tyr Thr Tyr Asn Ile Pro Gly Ile<br>385 390 395 400 | 1200 | |
| gta aat aat aat cca ttt tat ata tta ttt aca gta aat act aca gga<br>Val Asn Asn Asn Pro Phe Tyr Ile Leu Phe Thr Val Asn Thr Thr Gly<br>405 410 415 | 1248 | |
| att tat aaa att aat gct caa aat aat cta cca tca tta aaa ata tat<br>Ile Tyr Lys Ile Asn Ala Gln Asn Asn Leu Pro Ser Leu Lys Ile Tyr<br>420 425 430 | 1296 | |
| gaa gcg ata ggt tct ggt aat aga aat ttc caa tct ggg aat tta tgt<br>Glu Ala Ile Gly Ser Gly Asn Arg Asn Phe Gln Ser Gly Asn Leu Cys<br>435 440 445 | 1344 | |

```
gat gat gat att aaa gca ata aat tat att act ggg ttt gac agt cct    1392
Asp Asp Asp Ile Lys Ala Ile Asn Tyr Ile Thr Gly Phe Asp Ser Pro
        450                 455                 460 aat gct aaa agt tat tta gtt gtt ttg ctt aat aag gat aaa aat tac    1440
Asn Ala Lys Ser Tyr Leu Val Val Leu Leu Asn Lys Asp Lys Asn Tyr
465                 470                 475                 480 tac att aga gta cca caa act tct tct aat ata gaa aat caa ata aaa    1488
Tyr Ile Arg Val Pro Gln Thr Ser Ser Asn Ile Glu Asn Gln Ile Lys
                485                 490                 495 ttc aag aga gaa gaa ggg gat ctc cga aat tta atg aat tct tca gtt    1536
Phe Lys Arg Glu Glu Gly Asp Leu Arg Asn Leu Met Asn Ser Ser Val
            500                 505                 510 aat ata ata gat aat ctt aat tca aca ggt gca cat tac tat aca aga    1584
Asn Ile Ile Asp Asn Leu Asn Ser Thr Gly Ala His Tyr Tyr Thr Arg
        515                 520                 525 caa agc cct gat gtc cat gac tat att tca tat gaa ttt aca ata cct    1632
Gln Ser Pro Asp Val His Asp Tyr Ile Ser Tyr Glu Phe Thr Ile Pro
530                 535                 540 ggt aac ttt aat aat aaa gat aca tct aac att agg ctt tat act agt    1680
Gly Asn Phe Asn Asn Lys Asp Thr Ser Asn Ile Arg Leu Tyr Thr Ser
545                 550                 555                 560 tat aac caa gga ata ggt act tta ttt aga gtc act gaa act att gac    1728
Tyr Asn Gln Gly Ile Gly Thr Leu Phe Arg Val Thr Glu Thr Ile Asp
                565                 570                 575 ggc tat aat tta att aat ata caa caa aat tta aat ctc tta aat agt    1776
Gly Tyr Asn Leu Ile Asn Ile Gln Gln Asn Leu Asn Leu Leu Asn Ser
            580                 585                 590 acc aag tca ata cgt tta tta aat ggt gca att tat ata tta aaa gta    1824
Thr Lys Ser Ile Arg Leu Leu Asn Gly Ala Ile Tyr Ile Leu Lys Val
        595                 600                 605 gaa gtt aca gaa tta aat aac tat aat ata aaa ttg cat ata gat att    1872
Glu Val Thr Glu Leu Asn Asn Tyr Asn Ile Lys Leu His Ile Asp Ile
610                 615                 620 act aat taa                                                        1881
Thr Asn
625

<210> SEQ ID NO 7
<211> LENGTH: 9
<212> TYPE: PRT
<213> ORGANISM: Artificial
<220> FEATURE:
<223> OTHER INFORMATION: synthetic peptide

<400> SEQUENCE: 7

Asp Tyr Lys Asp Asp Asp Asp Lys Leu
1               5

<210> SEQ ID NO 8
<211> LENGTH: 23
<212> TYPE: PRT
<213> ORGANISM: Artificial
<220> FEATURE:
<223> OTHER INFORMATION: synthetic peptide

<400> SEQUENCE: 8

Ala Ser Trp Ser His Pro Gln Phe Glu Lys Gly Ala Leu Glu Val Leu
1               5                   10                  15

Phe Gln Gly Pro Gly Tyr Gln
            20
```

```
<210> SEQ ID NO 9
<211> LENGTH: 31
<212> TYPE: DNA
<213> ORGANISM: Artificial
<220> FEATURE:
<223> OTHER INFORMATION: primer

<400> SEQUENCE: 9
cactataagc ttatccaaaa ttcattaaat g                              31

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
gttgataggt accttatggg ttactcatag                                30

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
tgaataagct ttcagctgaa agaacttttc                                30

<210> SEQ ID NO 12
<211> LENGTH: 32
<212> TYPE: DNA
<213> ORGANISM: Artificial
<220> FEATURE:
<223> OTHER INFORMATION: primer

<400> SEQUENCE: 12
cactttggta ccttatattt tttcaagttt ga                             32

<210> SEQ ID NO 13
<211> LENGTH: 31
<212> TYPE: DNA
<213> ORGANISM: Artificial
<220> FEATURE:
<223> OTHER INFORMATION: primer

<400> SEQUENCE: 13
gaaaaagggt accaatatag tgatactatt g                              31

<210> SEQ ID NO 14
<211> LENGTH: 31
<212> TYPE: DNA
<213> ORGANISM: Artificial
<220> FEATURE:
<223> OTHER INFORMATION: primer

<400> SEQUENCE: 14
cgtgtcgact taattagtaa tatctatatg c                              31

<210> SEQ ID NO 15
<211> LENGTH: 293
<212> TYPE: PRT
<213> ORGANISM: Clostridium botulinum

<400> SEQUENCE: 15
```

Met Glu His Tyr Ser Val Ile Gln Asn Ser Leu Asn Asp Lys Ile Val
1               5                   10                  15

Thr Ile Ser Cys Lys Ala Asp Thr Asn Leu Phe Phe Tyr Gln Val Ala
            20                  25                  30

Gly Asn Val Ser Leu Phe Gln Gln Thr Arg Asn Tyr Leu Glu Arg Trp
            35                  40                  45

Arg Leu Ile Tyr Asp Ser Asn Lys Ala Ala Tyr Lys Ile Lys Ser Met
50                  55                  60

Asp Ile His Asn Thr Asn Leu Val Leu Thr Trp Asn Ala Pro Thr His
65                  70                  75                  80

Asn Ile Ser Thr Gln Gln Asp Ser Asn Ala Asp Asn Gln Tyr Trp Leu
            85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
            115                 120                 125

Leu Ser Thr Leu Asn Asn Ser Asn Tyr Ile Lys Phe Ile Ile Glu Asp
            130                 135                 140

Tyr Ile Ile Ser Asp Leu Asn Asn Phe Thr Cys Lys Ile Ser Pro Ile
145                 150                 155                 160

Leu Asp Leu Asn Lys Val Val Gln Gln Val Asp Val Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
195                 200                 205

Ser Asn Gly Val Leu Thr Trp Ile Phe Ser Asn Gly Asn Thr Val Arg
210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
            245                 250                 255

Asp Thr Thr Lys Ala Leu Asp Leu Tyr Gly Gly Gln Thr Ala Asn Gly
            260                 265                 270

Thr Ala Ile Gln Val Phe Asn Tyr His Gly Asp Asp Asn Gln Lys Trp
            275                 280                 285

Asn Ile Arg Asn Pro
            290

<210> SEQ ID NO 16
<211> LENGTH: 146
<212> TYPE: PRT
<213> ORGANISM: Clostridium botulinum

<400> SEQUENCE: 16

Met Ser Val Glu Arg Thr Phe Leu Pro Asn Gly Asn Tyr Asn Ile Lys
1               5                   10                  15

Ser Ile Phe Ser Gly Ser Leu Tyr Leu Asn Pro Val Ser Lys Ser Leu
            20                  25                  30

Thr Phe Ser Asn Glu Ser Ser Ala Asn Asn Gln Lys Trp Asn Val Glu
            35                  40                  45

Tyr Met Ala Glu Asn Arg Cys Phe Lys Ile Ser Asn Val Ala Glu Pro
50                  55                  60

Asn Lys Tyr Leu Ser Tyr Asp Asn Phe Gly Phe Ile Ser Leu Asp Ser
65                  70                  75                  80

```
Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Asp Tyr Ala Trp
            100                 105                 110

Asp Ile Tyr Asp Thr Asn Glu Asn Ile Leu Ser Gln Pro Leu Leu Leu
        115                 120                 125

Leu Pro Asn Phe Asp Ile Tyr Asn Ser Asn Gln Met Phe Lys Leu Glu
130                 135                 140

Lys Ile
145

<210> SEQ ID NO 17
<211> LENGTH: 626
<212> TYPE: PRT
<213> ORGANISM: Clostridium botulinum

<400> SEQUENCE: 17

Met Asn Ser Ser Ile Lys Lys Ile Tyr Asn Asp Ile Gln Glu Lys Val
1               5                   10                  15

Ile Asn Tyr Ser Asp Thr Ile Asp Leu Ala Asp Gly Asn Tyr Val Val
            20                  25                  30

Arg Arg Gly Asp Gly Trp Ile Leu Ser Arg Gln Asn Gln Ile Leu Gly
        35                  40                  45

Gly Ser Val Ile Ser Asn Gly Ser Thr Gly Ile Val Gly Asp Leu Arg
    50                  55                  60

Val Asn Asp Asn Ala Ile Pro Tyr Tyr Pro Thr Pro Ser Phe Asn
65                  70                  75                  80

Glu Glu Tyr Ile Lys Asn Asn Ile Gln Thr Val Phe Thr Asn Phe Thr
                85                  90                  95

Glu Ala Asn Gln Ile Pro Ile Gly Phe Glu Phe Ser Lys Thr Ala Pro
            100                 105                 110

Ser Asn Lys Asn Leu Tyr Met Tyr Leu Gln Tyr Thr Tyr Ile Arg Tyr
        115                 120                 125

Glu Ile Ile Lys Val Leu Gln His Glu Ile Ile Glu Arg Ala Val Leu
130                 135                 140

Tyr Val Pro Ser Leu Gly Tyr Val Lys Ser Ile Glu Phe Asn Pro Gly
145                 150                 155                 160

Glu Lys Ile Asn Lys Asp Phe Tyr Phe Leu Thr Asn Asp Lys Cys Ile
                165                 170                 175

Leu Asn Glu Gln Phe Leu Tyr Lys Lys Ile Leu Glu Thr Thr Lys Asn
            180                 185                 190

Ile Pro Thr Asn Asn Ile Phe Asn Ser Lys Val Ser Ser Thr Gln Arg
        195                 200                 205

Val Leu Pro Tyr Ser Asn Gly Leu Tyr Val Ile Asn Lys Gly Asp Gly
210                 215                 220

Tyr Ile Arg Thr Asn Asp Lys Asp Leu Ile Gly Thr Leu Leu Ile Glu
225                 230                 235                 240

Ala Gly Ser Ser Gly Ser Ile Ile Gln Pro Arg Leu Arg Asn Thr Thr
                245                 250                 255

Arg Pro Leu Phe Thr Thr Ser Asn Asp Thr Lys Phe Ser Gln Gln Tyr
            260                 265                 270

Thr Glu Glu Arg Leu Lys Asp Ala Phe Asn Val Gln Leu Phe Asn Thr
        275                 280                 285

Ser Thr Ser Leu Phe Lys Phe Val Glu Glu Ala Pro Ser Asp Lys Asn
```

```
                    290                 295                 300
Ile Cys Ile Lys Ala Tyr Asn Thr Tyr Glu Lys Tyr Glu Leu Ile Asp
305                 310                 315                 320

Tyr Gln Asn Gly Ser Ile Val Asn Lys Ala Glu Tyr Tyr Leu Pro Ser
                325                 330                 335

Leu Gly Tyr Cys Glu Val Thr Asn Ala Pro Ser Pro Glu Ser Glu Val
            340                 345                 350

Val Lys Met Gln Val Ala Glu Asp Gly Phe Ile Gln Asn Gly Pro Glu
        355                 360                 365

Glu Glu Ile Val Val Gly Val Ile Asp Pro Ser Glu Asn Ile Gln Glu
    370                 375                 380

Ile Asn Thr Ala Ile Ser Asp Asn Tyr Thr Tyr Asn Ile Pro Gly Ile
385                 390                 395                 400

Val Asn Asn Asn Pro Phe Tyr Ile Leu Phe Thr Val Asn Thr Thr Gly
                405                 410                 415

Ile Tyr Lys Ile Asn Ala Gln Asn Asn Leu Pro Ser Leu Lys Ile Tyr
            420                 425                 430

Glu Ala Ile Gly Ser Gly Asn Arg Asn Phe Gln Ser Gly Asn Leu Cys
        435                 440                 445

Asp Asp Asp Ile Lys Ala Ile Asn Tyr Ile Thr Gly Phe Asp Ser Pro
    450                 455                 460

Asn Ala Lys Ser Tyr Leu Val Val Leu Asn Lys Asp Lys Asn Tyr
465                 470                 475                 480

Tyr Ile Arg Val Pro Gln Thr Ser Ser Asn Ile Glu Asn Gln Ile Gln
                485                 490                 495

Phe Lys Arg Glu Glu Gly Asp Leu Arg Asn Leu Met Asn Ser Ser Val
            500                 505                 510

Asn Ile Ile Asp Asn Leu Asn Ser Thr Gly Ala His Tyr Tyr Thr Arg
        515                 520                 525

Gln Ser Pro Asp Val His Asp Tyr Ile Ser Tyr Glu Phe Thr Ile Pro
    530                 535                 540

Gly Asn Phe Asn Asn Lys Asp Thr Ser Asn Ile Arg Leu Tyr Thr Ser
545                 550                 555                 560

Tyr Asn Gln Gly Ile Gly Thr Leu Phe Arg Val Thr Glu Thr Ile Asp
                565                 570                 575

Gly Tyr Asn Leu Ile Asn Ile Gln Gln Asn Leu His Leu Leu Asn Asn
            580                 585                 590

Thr Asn Ser Ile Arg Leu Leu Asn Gly Ala Ile Tyr Ile Leu Lys Val
        595                 600                 605

Glu Val Thr Glu Leu Asn Asn Tyr Asn Ile Arg Leu His Ile Asp Ile
    610                 615                 620

Thr Asn
625

<210> SEQ ID NO 18
<211> LENGTH: 882
<212> TYPE: DNA
<213> ORGANISM: Clostridium botulinum
<220> FEATURE:
<221> NAME/KEY: CDS
<222> LOCATION: (1)..(882)

<400> SEQUENCE: 18 atg gaa cac tat tca gta atc caa aat tca tta aat gac aaa att gtt    48
Met Glu His Tyr Ser Val Ile Gln Asn Ser Leu Asn Asp Lys Ile Val
1               5                   10                  15
```

```
acc atc tcc tgt aag gcc gat act aat tta ttt ttt tat caa gtt gcc        96
Thr Ile Ser Cys Lys Ala Asp Thr Asn Leu Phe Phe Tyr Gln Val Ala
         20                  25                  30 ggt aac gtt agc tta ttt caa caa act aga aat tac ctt gaa aga tgg       144
Gly Asn Val Ser Leu Phe Gln Gln Thr Arg Asn Tyr Leu Glu Arg Trp
 35                  40                  45 aga ctt ata tat gat tct aat aaa gct gct tat aaa ata aaa agt atg       192
Arg Leu Ile Tyr Asp Ser Asn Lys Ala Ala Tyr Lys Ile Lys Ser Met
 50                  55                  60 gat atc cat aat act aat tta gtt tta aca tgg aat gca cca aca cat       240
Asp Ile His Asn Thr Asn Leu Val Leu Thr Trp Asn Ala Pro Thr His
65                  70                  75                  80 aat ata tca acg caa caa gat tca aat gca gat aat caa tat tgg tta       288
Asn Ile Ser Thr Gln Gln Asp Ser Asn Ala Asp Asn Gln Tyr Trp Leu
             85                  90                  95 tta tta aaa gac att ggt aac aat tca ttt att att gca agt tat aaa       336
Leu Leu Lys Asp Ile Gly Asn Asn Ser Phe Ile Ile Ala Ser Tyr Lys
            100                 105                 110 aac cct aac tta gta tta tat gct gat acc gta gct cgt aat ttg aag       384
Asn Pro Asn Leu Val Leu Tyr Ala Asp Thr Val Ala Arg Asn Leu Lys
        115                 120                 125 ctt agc aca ctt aat aat tca aat tat ata aaa ttt atc ata gaa gat       432
Leu Ser Thr Leu Asn Asn Ser Asn Tyr Ile Lys Phe Ile Ile Glu Asp
    130                 135                 140 tat ata ata tca gat ctt aac aat ttc aca tgt aaa ata agt cca ata       480
Tyr Ile Ile Ser Asp Leu Asn Asn Phe Thr Cys Lys Ile Ser Pro Ile
145                 150                 155                 160 tta gat ctt aat aaa gtt gta caa caa gtg gat gtg aca aat cta aat       528
Leu Asp Leu Asn Lys Val Val Gln Gln Val Asp Val Thr Asn Leu Asn
                165                 170                 175 gtt aat tta tat act tgg gac tat ggt cgc aat caa aaa tgg aca att       576
Val Asn Leu Tyr Thr Trp Asp Tyr Gly Arg Asn Gln Lys Trp Thr Ile
            180                 185                 190 aga tat aat gaa gaa aaa gca gca tac cag ttt ttt aat aca ata ctt       624
Arg Tyr Asn Glu Glu Lys Ala Ala Tyr Gln Phe Phe Asn Thr Ile Leu
        195                 200                 205 tca aac gga gtt cta aca tgg att ttt tca aat ggt aat act gta agg       672
Ser Asn Gly Val Leu Thr Trp Ile Phe Ser Asn Gly Asn Thr Val Arg
    210                 215                 220 gtt tct tct tct aat gat caa aat aat gac gcc caa tat tgg ctt ata       720
Val Ser Ser Ser Asn Asp Gln Asn Asn Asp Ala Gln Tyr Trp Leu Ile
225                 230                 235                 240 aat cct gtt tca gat act gat gaa aca tat aca att act aat cta cgc       768
Asn Pro Val Ser Asp Thr Asp Glu Thr Tyr Thr Ile Thr Asn Leu Arg
                245                 250                 255 gat aca act aaa gct cta gat tta tat ggc ggc caa aca gca aac gga       816
Asp Thr Thr Lys Ala Leu Asp Leu Tyr Gly Gly Gln Thr Ala Asn Gly
            260                 265                 270 act gct att caa gta ttt aat tat cat gga gat gat aat cag aaa tgg       864
Thr Ala Ile Gln Val Phe Asn Tyr His Gly Asp Asp Asn Gln Lys Trp
        275                 280                 285 aat att cgt aac cca taa                                                882
Asn Ile Arg Asn Pro
    290
```

<210> SEQ ID NO 19
<211> LENGTH: 441
<212> TYPE: DNA
<213> ORGANISM: Clostridium botulinum
<220> FEATURE:

```
<221> NAME/KEY: CDS
<222> LOCATION: (1)..(441)

<400> SEQUENCE: 19 atg tca gtt gaa aga act ttt cta cct aat ggt aat tac aat ata aaa      48
Met Ser Val Glu Arg Thr Phe Leu Pro Asn Gly Asn Tyr Asn Ile Lys
1               5                   10                  15 tct atc ttt tct ggt tct tta tat tta aat cct gta tcg aaa tca tta      96
Ser Ile Phe Ser Gly Ser Leu Tyr Leu Asn Pro Val Ser Lys Ser Leu
            20                  25                  30 aca ttt tca aat gaa tct tct gca aat aat caa aaa tgg aat gta gaa     144
Thr Phe Ser Asn Glu Ser Ser Ala Asn Asn Gln Lys Trp Asn Val Glu
        35                  40                  45 tat atg gct gaa aat aga tgc ttt aaa atc tct aat gta gca gaa cca     192
Tyr Met Ala Glu Asn Arg Cys Phe Lys Ile Ser Asn Val Ala Glu Pro
    50                  55                  60 aat aag tat tta agt tac gat aac ttt gga ttt att tct tta gat tca     240
Asn Lys Tyr Leu Ser Tyr Asp Asn Phe Gly Phe Ile Ser Leu Asp Ser
65                  70                  75                  80 tta tcc aat aga tgc tac tgg ttt cct att aaa att gct gta aat act     288
Leu Ser Asn Arg Cys Tyr Trp Phe Pro Ile Lys Ile Ala Val Asn Thr
                85                  90                  95 tat att atg tta agt tta aat aaa gtg aat gaa tta gat tat gcc tgg     336
Tyr Ile Met Leu Ser Leu Asn Lys Val Asn Glu Leu Asp Tyr Ala Trp
            100                 105                 110 gac att tat gat act aat gaa aat att tta agc caa cca cta ctc cta     384
Asp Ile Tyr Asp Thr Asn Glu Asn Ile Leu Ser Gln Pro Leu Leu Leu
        115                 120                 125 tta ccg aat ttt gat ata tac aat tca aat caa atg ttc aaa ctt gaa     432
Leu Pro Asn Phe Asp Ile Tyr Asn Ser Asn Gln Met Phe Lys Leu Glu
    130                 135                 140 aaa ata taa                                                          441
Lys Ile
145

<210> SEQ ID NO 20
<211> LENGTH: 1881
<212> TYPE: DNA
<213> ORGANISM: Clostridium botulinum
<220> FEATURE:
<221> NAME/KEY: CDS
<222> LOCATION: (1)..(1881)

<400> SEQUENCE: 20 atg aat tca tct ata aaa aaa att tat aat gat ata caa gaa aaa gtt      48
Met Asn Ser Ser Ile Lys Lys Ile Tyr Asn Asp Ile Gln Glu Lys Val
1               5                   10                  15 ata aac tat agt gat act att gat tta gct gat ggt aat tat gta gtt      96
Ile Asn Tyr Ser Asp Thr Ile Asp Leu Ala Asp Gly Asn Tyr Val Val
            20                  25                  30 aga aga ggg gat gga tgg ata tta tct aga caa aat caa ata tta ggt     144
Arg Arg Gly Asp Gly Trp Ile Leu Ser Arg Gln Asn Gln Ile Leu Gly
        35                  40                  45 gga agt gta att agt aat gga tca aca gga ata gtt ggg gac cta cgt     192
Gly Ser Val Ile Ser Asn Gly Ser Thr Gly Ile Val Gly Asp Leu Arg
    50                  55                  60 gta aat gat aat gcg ata cca tat tat tat cca aca cca tct ttc aat     240
Val Asn Asp Asn Ala Ile Pro Tyr Tyr Tyr Pro Thr Pro Ser Phe Asn
65                  70                  75                  80 gaa gaa tat ata aaa aat aat ata caa act gta ttt act aac ttt act     288
Glu Glu Tyr Ile Lys Asn Asn Ile Gln Thr Val Phe Thr Asn Phe Thr
                85                  90                  95
```

```
gaa gct aat caa att cca ata gga ttt gaa ttt agt aaa acc gct ccc    336
Glu Ala Asn Gln Ile Pro Ile Gly Phe Glu Phe Ser Lys Thr Ala Pro
            100                 105                 110 tca aat aaa aac tta tat atg tat tta caa tat acc tac att aga tat    384
Ser Asn Lys Asn Leu Tyr Met Tyr Leu Gln Tyr Thr Tyr Ile Arg Tyr
        115                 120                 125 gaa ata ata aaa gtc tta caa cat gaa att ata gaa aga gca gtt tta    432
Glu Ile Ile Lys Val Leu Gln His Glu Ile Ile Glu Arg Ala Val Leu
    130                 135                 140 tat gtt cca tct ctt gga tat gtt aag tct ata gaa ttt aat cca ggg    480
Tyr Val Pro Ser Leu Gly Tyr Val Lys Ser Ile Glu Phe Asn Pro Gly
145                 150                 155                 160 gaa aaa ata aat aaa gat ttt tac ttt cta act aat gat aag tgc att    528
Glu Lys Ile Asn Lys Asp Phe Tyr Phe Leu Thr Asn Asp Lys Cys Ile
                165                 170                 175 tta aat gaa caa ttc cta tat aaa aaa att tta gaa act act aaa aat    576
Leu Asn Glu Gln Phe Leu Tyr Lys Lys Ile Leu Glu Thr Thr Lys Asn
            180                 185                 190 ata cca act aac aat att ttt aat tct aaa gtt agt agc aca caa cga    624
Ile Pro Thr Asn Asn Ile Phe Asn Ser Lys Val Ser Ser Thr Gln Arg
        195                 200                 205 gta ttg cct tat agt aat ggg cta tat gtt att aat aag ggt gat gga    672
Val Leu Pro Tyr Ser Asn Gly Leu Tyr Val Ile Asn Lys Gly Asp Gly
    210                 215                 220 tat ata aga aca aat gat aaa gat ttg ata ggt aca tta tta atc gaa    720
Tyr Ile Arg Thr Asn Asp Lys Asp Leu Ile Gly Thr Leu Leu Ile Glu
225                 230                 235                 240 gca ggt tca tca gga agt att ata caa cct cga tta aga aat aca act    768
Ala Gly Ser Ser Gly Ser Ile Ile Gln Pro Arg Leu Arg Asn Thr Thr
                245                 250                 255 aga cca tta ttc acc aca agt aat gat aca aaa ttc tca caa caa tat    816
Arg Pro Leu Phe Thr Thr Ser Asn Asp Thr Lys Phe Ser Gln Gln Tyr
            260                 265                 270 act gaa gaa aga ctt aaa gac gct ttc aat gta caa tta ttt aat aca    864
Thr Glu Glu Arg Leu Lys Asp Ala Phe Asn Val Gln Leu Phe Asn Thr
        275                 280                 285 tca aca tcg tta ttt aaa ttt gta gaa gaa gct cct tca gat aaa aat    912
Ser Thr Ser Leu Phe Lys Phe Val Glu Glu Ala Pro Ser Asp Lys Asn
    290                 295                 300 ata tgc ata aag gct tat aat acc tat gaa aaa tat gaa tta ata gac    960
Ile Cys Ile Lys Ala Tyr Asn Thr Tyr Glu Lys Tyr Glu Leu Ile Asp
305                 310                 315                 320 tat caa aat gga agt att gtt aat aaa gct gag tat tat ctt cct tcc   1008
Tyr Gln Asn Gly Ser Ile Val Asn Lys Ala Glu Tyr Tyr Leu Pro Ser
                325                 330                 335 tta gga tat tgt gaa gta act aat gct cct tca cct gaa tct gaa gta   1056
Leu Gly Tyr Cys Glu Val Thr Asn Ala Pro Ser Pro Glu Ser Glu Val
            340                 345                 350 gtt aaa atg caa gtg gct gaa gat gga ttt ata caa aat ggt ccc gag   1104
Val Lys Met Gln Val Ala Glu Asp Gly Phe Ile Gln Asn Gly Pro Glu
        355                 360                 365 gaa gaa att gta gta ggt gtc ata gac cca tct gaa aat ata caa gaa   1152
Glu Glu Ile Val Val Gly Val Ile Asp Pro Ser Glu Asn Ile Gln Glu
    370                 375                 380 ata aat act gct att tca gat aat tac aca tat aac att cca ggt att   1200
Ile Asn Thr Ala Ile Ser Asp Asn Tyr Thr Tyr Asn Ile Pro Gly Ile
385                 390                 395                 400 gta aat aat aat cca ttt tat ata tta ttt aca gta aat act aca gga   1248
Val Asn Asn Asn Pro Phe Tyr Ile Leu Phe Thr Val Asn Thr Thr Gly
```

|   |   |   |   |   |   |   |   |   |   |   |   |   |   |   |   |   |
|---|---|---|---|---|---|---|---|---|---|---|---|---|---|---|---|---|
|   |   |   | 405 |   |   |   | 410 |   |   |   | 415 |   |   |   |   |   |
| att | tat | aaa | att | aat | gct | caa | aat | aat | cta | cca | tca | tta | aaa | ata | tat | 1296 |
| Ile | Tyr | Lys | Ile | Asn | Ala | Gln | Asn | Asn | Leu | Pro | Ser | Leu | Lys | Ile | Tyr |   |
|   |   |   | 420 |   |   |   | 425 |   |   |   | 430 |   |   |   |   |   |
| gaa | gcg | ata | ggt | tct | ggt | aat | aga | aat | ttc | caa | tct | ggg | aat | tta | tgt | 1344 |
| Glu | Ala | Ile | Gly | Ser | Gly | Asn | Arg | Asn | Phe | Gln | Ser | Gly | Asn | Leu | Cys |   |
|   |   |   | 435 |   |   |   | 440 |   |   |   | 445 |   |   |   |   |   |
| gat | gat | gat | att | aaa | gca | ata | aat | tat | att | act | ggg | ttt | gac | agt | cct | 1392 |
| Asp | Asp | Asp | Ile | Lys | Ala | Ile | Asn | Tyr | Ile | Thr | Gly | Phe | Asp | Ser | Pro |   |
|   |   | 450 |   |   |   | 455 |   |   |   | 460 |   |   |   |   |   |   |
| aat | gct | aaa | agt | tat | tta | gtt | gtt | ttg | ctt | aat | aag | gat | aaa | aat | tac | 1440 |
| Asn | Ala | Lys | Ser | Tyr | Leu | Val | Val | Leu | Leu | Asn | Lys | Asp | Lys | Asn | Tyr |   |
| 465 |   |   |   | 470 |   |   |   | 475 |   |   |   | 480 |   |   |   |   |
| tac | att | aga | gta | cca | caa | act | tct | tct | aat | ata | gaa | aat | caa | ata | caa | 1488 |
| Tyr | Ile | Arg | Val | Pro | Gln | Thr | Ser | Ser | Asn | Ile | Glu | Asn | Gln | Ile | Gln |   |
|   |   |   |   | 485 |   |   |   | 490 |   |   |   | 495 |   |   |   |   |
| ttc | aag | aga | gaa | gaa | ggg | gat | ctc | cga | aat | tta | atg | aat | tct | tca | gtt | 1536 |
| Phe | Lys | Arg | Glu | Glu | Gly | Asp | Leu | Arg | Asn | Leu | Met | Asn | Ser | Ser | Val |   |
|   |   |   | 500 |   |   |   | 505 |   |   |   | 510 |   |   |   |   |   |
| aat | ata | ata | gat | aat | ctt | aat | tca | aca | ggt | gca | cat | tac | tat | aca | aga | 1584 |
| Asn | Ile | Ile | Asp | Asn | Leu | Asn | Ser | Thr | Gly | Ala | His | Tyr | Tyr | Thr | Arg |   |
|   |   |   |   | 515 |   |   |   | 520 |   |   |   | 525 |   |   |   |   |
| caa | agc | cct | gat | gtc | cat | gac | tat | att | tca | tat | gaa | ttt | aca | ata | cct | 1632 |
| Gln | Ser | Pro | Asp | Val | His | Asp | Tyr | Ile | Ser | Tyr | Glu | Phe | Thr | Ile | Pro |   |
|   |   | 530 |   |   |   | 535 |   |   |   | 540 |   |   |   |   |   |   |
| ggt | aac | ttt | aat | aat | aaa | gat | aca | tct | aac | att | agg | ctt | tat | act | agt | 1680 |
| Gly | Asn | Phe | Asn | Asn | Lys | Asp | Thr | Ser | Asn | Ile | Arg | Leu | Tyr | Thr | Ser |   |
| 545 |   |   |   | 550 |   |   |   | 555 |   |   |   | 560 |   |   |   |   |
| tat | aac | caa | gga | ata | ggt | act | tta | ttt | aga | gtc | act | gaa | act | att | gac | 1728 |
| Tyr | Asn | Gln | Gly | Ile | Gly | Thr | Leu | Phe | Arg | Val | Thr | Glu | Thr | Ile | Asp |   |
|   |   |   |   | 565 |   |   |   | 570 |   |   |   | 575 |   |   |   |   |
| ggc | tat | aat | tta | att | aat | ata | caa | caa | aat | tta | cac | ctc | tta | aat | aat | 1776 |
| Gly | Tyr | Asn | Leu | Ile | Asn | Ile | Gln | Gln | Asn | Leu | His | Leu | Leu | Asn | Asn |   |
|   |   |   | 580 |   |   |   | 585 |   |   |   | 590 |   |   |   |   |   |
| acc | aat | tca | ata | cgt | tta | tta | aat | ggt | gca | att | tat | ata | tta | aaa | gta | 1824 |
| Thr | Asn | Ser | Ile | Arg | Leu | Leu | Asn | Gly | Ala | Ile | Tyr | Ile | Leu | Lys | Val |   |
|   |   | 595 |   |   |   | 600 |   |   |   | 605 |   |   |   |   |   |   |
| gaa | gtt | aca | gaa | tta | aat | aac | tat | aat | ata | aga | ttg | cat | ata | gat | att | 1872 |
| Glu | Val | Thr | Glu | Leu | Asn | Asn | Tyr | Asn | Ile | Arg | Leu | His | Ile | Asp | Ile |   |
|   |   | 610 |   |   |   | 615 |   |   |   | 620 |   |   |   |   |   |   |
| act | aat | taa |   |   |   |   |   |   |   |   |   |   |   |   |   | 1881 |
| Thr | Asn |   |   |   |   |   |   |   |   |   |   |   |   |   |   |   |
| 625 |   |   |   |   |   |   |   |   |   |   |   |   |   |   |   |   |

<210> SEQ ID NO 21
<211> LENGTH: 8
<212> TYPE: PRT
<213> ORGANISM: Artificial
<220> FEATURE:
<223> OTHER INFORMATION: synthetic peptide

<400> SEQUENCE: 21

Asp Tyr Lys Asp Asp Asp Asp Lys
1               5

<210> SEQ ID NO 22
<211> LENGTH: 22
<212> TYPE: PRT
<213> ORGANISM: Artificial
<220> FEATURE:
<223> OTHER INFORMATION: synthetic peptide -continued

<400> SEQUENCE: 22

Ala Ser Trp Ser His Pro Gln Phe Glu Lys Gly Ala Leu Glu Val Leu
1               5                   10                  15

Phe Gln Gly Pro Gly Tyr
            20

<210> SEQ ID NO 23
<211> LENGTH: 29
<212> TYPE: DNA
<213> ORGANISM: Artificial
<220> FEATURE:
<223> OTHER INFORMATION: primer

<400> SEQUENCE: 23
catgccatgg taatccaaaa ttcattaaa                                    29

<210> SEQ ID NO 24
<211> LENGTH: 57
<212> TYPE: DNA
<213> ORGANISM: Artificial
<220> FEATURE:
<223> OTHER INFORMATION: primer

<400> SEQUENCE: 24
cgggatcctt acttgtcatc gtcatccttg tagtctgggt tacgaatatt ccatttc     57

<210> SEQ ID NO 25
<211> LENGTH: 33
<212> TYPE: DNA
<213> ORGANISM: Artificial
<220> FEATURE:
<223> OTHER INFORMATION: primer

<400> SEQUENCE: 25
tgaataagct ttcagttgaa agaactttc tac                                33

<210> SEQ ID NO 26
<211> LENGTH: 32
<212> TYPE: DNA
<213> ORGANISM: Artificial
<220> FEATURE:
<223> OTHER INFORMATION: primer

<400> SEQUENCE: 26
ctttggtacc ttatattttt tcaagtttga ac                                32

<210> SEQ ID NO 27
<211> LENGTH: 34
<212> TYPE: DNA
<213> ORGANISM: Artificial
<220> FEATURE:
<223> OTHER INFORMATION: primer

<400> SEQUENCE: 27
aaagttaggt accctagtga tactattgat ttag                              34

<210> SEQ ID NO 28
<211> LENGTH: 31
<212> TYPE: DNA
<213> ORGANISM: Artificial
<220> FEATURE:
<223> OTHER INFORMATION: primer

<400> SEQUENCE: 28

```
cgtgtcgact taattagtaa tatctatatg c                                    31
```